(12) United States Patent
Donlon et al.

(10) Patent No.: US 6,651,671 B1
(45) Date of Patent: *Nov. 25, 2003

(54) LENS-INVASIVE DEVICES AND METHODS FOR CARDIAC VALVE SURGERY

(75) Inventors: Brian S. Donlon, Los Altos Hills, CA (US); William S. Peters, Elwood (AU); Michi E. Garrison, Half Moon Bay, CA (US); Daniel C. Rosenman, San Francisco, CA (US); John H. Stevens, London (GB)

(73) Assignee: Heartport, Inc., Redwood, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/416,492

(22) Filed: Oct. 12, 1999

Related U.S. Application Data

(63) Continuation of application No. 08/594,870, filed on Jan. 31, 1996, now Pat. No. 6,010,531, which is a continuation-in-part of application No. 08/485,600, filed on Jun. 7, 1995, now abandoned, which is a continuation-in-part of application No. 08/281,962, filed on Jul. 28, 1994, now abandoned, which is a continuation-in-part of application No. 08/163,241, filed on Dec. 6, 1993, now Pat. No. 5,571,215, which is a continuation-in-part of application No. 08/023,778, filed on Feb. 22, 1993, now Pat. No. 5,452,733, and a continuation-in-part of application No. 08/486,941, filed on Jun. 7, 1995, now Pat. No. 5,799,661.

(51) Int. Cl.$^7$ .............................................. A61B 19/00
(52) U.S. Cl. ..................................................... 128/898
(58) Field of Search ........................ 128/898; 623/2.11, 623/2.12, 66; 604/48, 96, 49, 174, 175, 264; 606/51, 52, 53, 170, 174; 601/201, 204

(56) References Cited

U.S. PATENT DOCUMENTS

| 3,409,013 A | 11/1968 | Berry |
| 3,587,115 A | 6/1971 | Shiley |
| 3,626,471 A | 12/1971 | Florin |
| 3,983,863 A | 10/1976 | Janke et al. |
| 4,049,000 A | 9/1977 | Williams |

(List continued on next page.)

FOREIGN PATENT DOCUMENTS

| CA | 2116534 | 3/1993 |
| CA | 2168369 | 2/1995 |

(List continued on next page.)

OTHER PUBLICATIONS

Jamieson, W.R.E., "Modern cardiac valve devices–bioprostheses and mechanical protheses", J Card Sug 8:89–98 (1983).

(List continued on next page.)

Primary Examiner—David J. Isabella

(57) ABSTRACT

Systems and methods are disclosed for performing less-invasive surgical procedures within the heart. A method for less-invasive repair or replacement of a cardiac valve comprises placing an instrument through an intercostal access port and through a penetration in a wall of a vessel in communication with the heart, advancing the instrument into the heart, and using the instrument to perform a surgical intervention on a cardiac valve in the heart under visualization through an intercostal access port. The surgeons hands are kept outside of the chest during each step. The surgical intervention may comprise replacing the cardiac valve with a prosthetic valve, wherein the native valve is removed using a tissue removal instrument, the native valve annulus is sized with a specialized sizing device, a prosthetic valve is introduced through an intercostal access port and through the penetration in the vessel, and the prosthetic valve is secured at the native valve position, all using instruments positioned through intercostal access ports without placing the hands inside the chest. Systems and devices for performing these procedures are also disclosed.

15 Claims, 37 Drawing Sheets

U.S. PATENT DOCUMENTS

| | | |
|---|---|---|
| 4,056,854 A | 11/1977 | Boretos et al. |
| 4,065,816 A | 1/1978 | Sawyer |
| 2,646,045 A | 7/1978 | Priestly |
| 4,111,209 A | 9/1978 | Wolvek et al. |
| 4,154,245 A | 5/1979 | Daily |
| 4,173,981 A | 11/1979 | Mortensen |
| 4,185,636 A | 1/1980 | Gabbay et al. |
| 4,259,961 A | 4/1981 | Hood, III |
| 4,416,281 A | 11/1983 | Cooper et al. |
| 4,423,730 A | 1/1984 | Gabbay |
| 4,553,543 A | 11/1985 | Amarasinghe |
| 4,562,832 A | 1/1986 | Wilder et al. |
| 4,585,453 A | 4/1986 | Martin et al. |
| 4,592,340 A | 6/1986 | Boyles |
| 4,602,911 A | 7/1986 | Ahmadi et al. |
| 4,605,006 A | 8/1986 | Jacques |
| 4,637,377 A | 1/1987 | Loop |
| 4,655,218 A | 4/1987 | Kulik et al. |
| 4,665,906 A | 5/1987 | Jervis |
| 4,679,556 A | 7/1987 | Lubock et al. |
| 4,781,682 A | 11/1988 | Patel |
| 4,803,984 A | 2/1989 | Narayanan et al. |
| 4,808,163 A | 2/1989 | Laub |
| 4,822,345 A | 4/1989 | Danforth |
| 4,877,016 A | 10/1989 | Kantor et al. |
| 4,943,277 A | 7/1990 | Bolling |
| 4,971,056 A | 11/1990 | Seacord |
| 4,973,300 A | 11/1990 | Wright |
| 5,002,528 A | 3/1991 | Palestrant |
| 5,011,469 A | 4/1991 | Buckberg et al. |
| 5,014,695 A | 5/1991 | Benak et al. |
| 5,032,128 A | 7/1991 | Alonso |
| 5,041,130 A | 8/1991 | Cosgrove et al. |
| 5,067,957 A | 11/1991 | Jervis |
| 5,104,393 A | 4/1992 | Isner et al. |
| 5,109,859 A | 5/1992 | Jenkins |
| 5,117,822 A | 6/1992 | Laghi |
| 5,150,706 A | 9/1992 | Cox et al. |
| 5,188,619 A | 2/1993 | Myers |
| 5,197,979 A | 3/1993 | Quintero et al. |
| 5,203,771 A | 4/1993 | Melker et al. |
| 5,203,776 A | 4/1993 | Melker et al. |
| 5,203,786 A | 4/1993 | Vernick |
| 5,209,747 A | 5/1993 | Knoepfler |
| 5,211,683 A | 5/1993 | Maginot |
| 5,213,093 A | 5/1993 | Swindle |
| 5,236,450 A | 8/1993 | Scott |
| 5,250,038 A | 10/1993 | Melker et al. |
| 5,271,385 A | 12/1993 | Bailey |
| 5,279,575 A | 1/1994 | Sugarbaker |
| 5,304,184 A | 4/1994 | Hathaway et al. |
| 5,304,220 A | 4/1994 | Maginot |
| 5,306,234 A | 4/1994 | Johnson |
| 5,308,320 A | 5/1994 | Safar et al. |
| 5,309,896 A | 5/1994 | Moll et al. |
| 5,312,344 A | 5/1994 | Grinfeld et al. |
| 5,318,012 A | 6/1994 | Wilk |
| 5,318,013 A | 6/1994 | Wilk |
| 5,325,848 A | 7/1994 | Adams et al. |
| 5,330,498 A | 7/1994 | Hill |
| 5,332,402 A | 7/1994 | Teitelbaum |
| 5,339,800 A | 8/1994 | Witta et al. |
| 5,339,803 A | 8/1994 | Mayzels et al. |
| 5,346,115 A | 9/1994 | Perouse et al. |
| 5,358,496 A | 10/1994 | Ortiz et al. |
| 5,361,752 A | 11/1994 | Moll et al. |
| 5,362,294 A | 11/1994 | Seitzinger |
| 5,370,109 A | 12/1994 | Cuny |
| 5,370,647 A | 12/1994 | Graber et al. |
| 5,370,685 A | 12/1994 | Stevens |
| 5,376,094 A | 12/1994 | Kline |
| 5,383,888 A | 1/1995 | Zvenyatsky et al. |
| 5,391,156 A | 2/1995 | Hildwein et al. |
| 5,392,787 A | 2/1995 | Yoon |
| 5,411,552 A | 5/1995 | Andersen et al. |
| 5,423,887 A | 6/1995 | Love et al. |
| 5,425,705 A | 6/1995 | Evard et al. |
| 5,433,700 A | 7/1995 | Peters |
| 5,441,494 A | 8/1995 | Ortiz |
| 5,443,446 A | 8/1995 | Shturman |
| 5,452,733 A | 9/1995 | Sterman et al. |
| 5,456,712 A | 10/1995 | Maginot |
| 5,458,574 A | 10/1995 | Machold et al. |
| 5,465,711 A | 11/1995 | Moll et al. |
| 5,474,571 A | 12/1995 | Lang |
| 5,478,309 A | 12/1995 | Sweezer et al. |
| 5,499,996 A | 3/1996 | Hill |
| 5,501,698 A * | 3/1996 | Roth et al. ................ 606/205 |
| 5,509,890 A | 4/1996 | Kazama |
| 5,522,834 A | 6/1996 | Fonger et al. |
| 5,522,838 A | 6/1996 | Hill |
| 5,536,251 A | 7/1996 | Everd et al. |
| 5,545,214 A | 8/1996 | Stevens |
| 5,556,412 A | 9/1996 | Hill |
| 5,558,620 A | 9/1996 | Heckele et al. |
| 5,558,644 A | 9/1996 | Boyd et al. |
| RE35,352 E | 10/1996 | Peters |
| 5,560,487 A | 10/1996 | Starr |
| 5,569,274 A | 10/1996 | Rapacki et al. |
| 5,571,119 A | 11/1996 | Atala |
| 5,571,215 A * | 11/1996 | Sterman et al. .............. 623/66 |
| 5,578,076 A | 11/1996 | Krueger et al. |
| 5,584,803 A | 12/1996 | Stevens et al. |
| 5,588,949 A | 12/1996 | Taylor et al. |
| 5,601,576 A | 2/1997 | Garrison |
| 5,613,937 A | 3/1997 | Garrison et al. |
| 5,626,607 A | 5/1997 | Malecki et al. |
| 5,682,906 A * | 11/1997 | Sterman .................... 128/898 |
| 5,702,368 A | 12/1997 | Stevens et al. |
| 5,799,661 A * | 9/1998 | Boyd et al. ................ 128/898 |
| 5,855,210 A * | 1/1999 | Sterman et al. ............ 128/898 |
| 6,010,531 A1 * | 1/2001 | Donlon et al. ............. 128/898 |
| 6,167,889 B1 * | 1/2001 | Benetti ..................... 128/898 |

FOREIGN PATENT DOCUMENTS

| | | |
|---|---|---|
| EP | 0218275 | 4/1987 |
| FR | 26841775 | 4/1993 |
| SU | 1690738 A | 11/1991 |
| WO | WO 87/05489 | 9/1987 |
| WO | WO 93/07926 | 4/1993 |
| WO | WO 93/20741 | 10/1993 |
| WO | WO 93/20742 | 10/1993 |
| WO | WO 94/03142 | 2/1994 |
| WO | WO 94/13211 | 6/1994 |
| WO | WO 94/16630 | 8/1994 |
| WO | WO 95/01757 | 1/1995 |

OTHER PUBLICATIONS

Landreneau et al., "Video–assisted thoracic surgery", Ann Thorac Sug 54:800–7 (1992).

Mack et al., "Present role of thoracoscopy in diagnosis and treatment of diseases of the chest", Ann Thorac Sug 54:403–9 (1992).

Magovern, G.J., "Sutureless aortic and mitral prosthetic valves", J Thoracic and Cardiovasc Sug., 48(3):346–361 (1964).

Ozuner et al., "Creation of a pericardial window using thoracoscopic techniques", Surg., Gynecoloy & Obstetrics, 175:69–71 (1992).

Wakabayashi, A., "Expanded applications of diagnostics and therapeutic thoracoscopy", J Thorac and Cardiovasc Surg 102:721–3 (1991).

Cohn et al., "Right thoracotomy, femorofemoral bypass, and deep hypothermia for re-replacement of the mitral valve", Ann Thorac Surg, 48:69–71 (1989).

Fundaro et al., "Towards an easier and safter reoperation of the atrioventricular valves", J Cardiovasc Surg 30:779–781 (1989).

Tribble et al., "Anterolateral thoracotomy as an alternative to repeat median sternotomy for replacement of the mitral valve", Ann Thorac Surg, 43:380–382 (1987).

Berreklouw et al., "Revival of right thoracotomy to approach atrioventricular valves in reoperations", Thorac Cardiovasc Surgeon 32:331–333 (1984).

Cosgrove, D.M., "Management of the calcified aorta: An alternative method of occlusion", Ann Thorac Surg 36:718–719.

Foster and Threlkel, "Proximal control of aorta with a balloon catheter", Surg, Gynecology & Obstetrics pp. 693–694 (1971).

Earth, Jr. and Stoney, Jr., "Balloon catheter occlusion of ascending aorta", Ann Thorac Surg, 35:560–561 (1983).

Sakaguchi et al., "Aortic valve replacement and coronary artery bypass", J. Japanese Assoc for Thoracic Surgery 41(6):1063–1068 (1993).

Duran, C., "Present Status of Reconstructive Surgery for Aortic Valve Disease", J Card Surg (1993), 8:443–452.

Meditech®, Instructions for Use, Occlusion Balloon Catheters rev. mar. 1991, pp. 1–7.

Kon et al., "Comparison of Implantation Techniques Using Freestyle Stentless Porcine Aortic Valve", Ann Thorac Surg, 59:857–62 (1995).

Hirose et al., "Another Approach for Aortic Valve Replacement Through Left Thoracotomy", Ann Thorac Surg, 58:884–886 (1994).

Rao and Kumar, "Aortic Valve Replacement through Right Thoracotomy", Texas Heart Institute Journal, 20(4):307–308 (1993).

Andrews, S.M. et al., "Laparoscopic Knot Substitutes, An Assessment of Techniques of Securign Sutures Through the Laparoscope", End. Sug., 2:62–65 (1994).

Hall, T.S., "A Strategy for Proximal Arterial Anastomosis", Ann. Thorac, Surg., 58:1500–1551 (1994).

Lirici, M.M. et al., "Tissue Approximation in minimal Invasive Surgery", End. Surg. 2:47–54 (1994).

Rossi, M., "Flexistrap® BC: A New Flexible Circular Stapler for Endoscopic Surgery", End. Sug. 2:69–70 (1994).

Szabo, Z. et al., "Analysis of Surgical Movements During Suturing in Laparoscopy", End. Surg. 2:55–61 (1994).

Asamura et al., "Computed Tornography–guided Coil Injection and Thoracoscopic Pulmonary Resection Under Roentgenographic Fluorocopy", Ann Thorac Surg., 58:1542–1544 (1994).

Barner and Vardhn, "Complete Myocardial Revascularization with Arterial Conduits", Advances in Cardiac Surgery, 5:27–45 (1994).

Barner et al., "Aorto–coronary Vein Graft and Internal Mammary–coronary Anastomosis", Arch Surg, 105:908–911 (1972).

Barner et al., "Use fo the Inferior Epigastric Artery as a Free Graft for Myocardial Revascularization", Ann Thorac Surg, 52:429–437 (1991).

Burke et al., "Video–assisted Cardioscopy in Congenital Heart Operation", Ann Thorac Surg. 58:864–868 (1994).

Calafiore et al., "Composite Arterial Conduits for a Wilder Arterial Myocardial Revascularization", Ann Thorac Surg., 58:185–190 (1994).

Canver and Dame, "Ultrasonic Assessment of Internal thoracic Artery Graft Flow in the Revascularized Heart", Ann Thorac Surg., 58:135–138 (1994).

Carpentier et al., "The Aorta–to–coronary Radial Artery Bypass Graft", Ann Thorac Surg., 16–111–121 (1973).

Dignan et al., "Reactivity of Gastroepiploic Artery and Internal Mammary Artery", J Thorac Cardiovasc Surg. 103:116–23 (1992).

Edwards et al., "Coronary Artery Bypass with Internal Mammary and Splenic Artery Grafts", Ann Thorac Surg., 15:35–40 (1973).

Engleman et al., "Fast–track Recovery fo the Coronary Bypass Patient", Ann thorac Surg., 58:1742–1746.

Fisk et al., "Experience with Radial Artery Graft for Coronary Artery Bypass", Ann Thorac Surg., 21:513–518 (1976).

Gavaghan et al., "Immediate Postoperative Aspirin Improves Vein Graft Patency Early Late After CABG Surgery", Circulation 83:1526–1534 (1991).

Grover et al., "The Veterans Affairs Continuous Improvement in Cardiac Surgery Study", Ann Thorac Study., 58:1845–1851 (1994).

Hamm et al., "A Randomized Study of Coranary Angioplasty Compared with Bypass Surgery in Patients with Symptomatic Multivessel Coronary Disease", NEJM, 331:1037–1043 (1994).

Hannan et al., "New York State's Cardiac Surgery Reporting System: Four years later", Ann Thorac Surg., 58:1852–1857 (1994).

Hattler et al., "Risk Stratification Using the Society of Thoracic Surgeons Program", Ann Thorac Surg., 58:1348–1352 (1994).

He et al., "Middle and Proximal Sections of the Human Internal Mammary Artery are not 'Passive Conduits'", J. Thorac Card Surg., pp. 741–746 (1994).

Isomura et al., "The RGEA and its Growth Potential", J Thorac Card Surg., 108:592–593 (1994).

Isomura et al., "Use of the Pedicled RGEA for CABG in the Presence of Calcified Ascendign Aorta", J Thorac Card Surg., 108:590–592 (1994).

Kaul et al., "Angioplasty Versus Coronary Artery Bypass in Octogenarians", Ann Thorac Surg., 58:1419–1426 (1994).

King et al., "A Randomized Trial comparing coronary Angioplasty with Coronary Bypass Surgery", NEJM 331:1044–1050 (1994).

Loop et al., "Influence of the IMA Graft on 10 Year Survival and other Cardiac Events", New England Journal of Medicine, 314:1–6 (1986).

Louagie et al., "Intraoperative Assessment of Coronary Artery Bypass Grafts using a Pulsed Doppler Flowmeter", Ann Thorac Surg., 58:742–749 (1994).

Lytle et al., "Long Term (5 to 12 years) Serial Studies of IMA and SV Coronary Bypass Grafts", J Thorac Cardiovasc Surg., 89:248–258 (1985).

McLaughlin, "Simple Internal Mammary Arter Retrator", Ann Thorac Surg., 58:1560–1570 (1994).

Milgalter and Laks, "A Technique to Harvest the IEAs for Coronary Bypass Procedures", J Card Surg., 6:306–310 (1991).

Morris et al., "Operation for Ventricular Tachyarrhythmias: Refining current techniques", Ann Thoras Surg., 58:1490–1498 (1994).

Nguyen et al., "Mammary Artery Versus Saphenous Vein: Assessment of basic fibroplast growth factor receptors", Ann Thorac Surg., 54:308–311 (1994).

Niimi et al., "Intraoperative Measurement of Saphenous Vein Bypass Graft Flow with TEE", J Cardio Vasc Anes., 7:294–299 (1993).

Nishida et al., "CABG with the Right Gastroepiploic Artery and Evaluation of Flow with Transcutaneous Doppler Echo", J Thorac Card Surg., 108:532–539 (1994).

Noyez et al., "Use of Internal Mammary Artery for Emergency Grafting After Failed Coronary Angioplasty", Ann Thorac Surg., 58:1784–1785 (1994).

Oei et al., "Color Doppler Imaging of the RGEA as an In Situ CABG", Eur Jour of Rad., 15:37–39 (1992).

Peigh et al., "Effect of Advancign Age on Cost and Outcome of Coronary Artery Bypass Grafting", Ann Thorac Surg., 58:1362–1367 (1994).

Peng et al., "Postoperative Pleural Changes After Coronary Revascularization", Ches, 101:327–330 (1992).

Piantadosi, "Biostatiatics and Clinical Trials for Thoracic Surgery", Ann Thorac Surg., 58:1556–1557 (1994).

Puig et al., "Inferior Epigastic Artery as a Free Graft for Myocardial Revascularization", J. Thorac Cardiovasc Surg., 99:251–255 (1990).

Pym et al., "Gastroepiploic Coronary Anastomosis", J Thorac Cardiovasc Surg, 94:256–259 (1987).

Ramstron et al., "Multiarterial CABG with Special Reference to Small Vessel Disease and Results in Women", Eur Soc Cardio 1 (1993).

Shapira et al., "Thoracotomy for Repair of Left Ventricular Aneurysm in a Patient with Coronary Bypass Grafts", Ann Thorac Surg, 58:1536–1538 (1994).

Stevens et al., "Closed–chest Coronary Artery Bypass with Carioplegic Arrest in Dog", Circulation, 90:1251 (1994).

Suma et al., "Bovine Internal Thoracic Artery", J Card Surg, 199:32:268–270.

Suzuki et al., "New Composite Graft Repair for Patients with and without Marfan's Syndrome", Ann Thorac Surg, 58:1457–1461 (1994).

Tadjkarimi et al., "Endothelial Function and Vasodilator Profile fo the Inferior Epigastric Artery", Ann Thorac Surg, 58:207–210 (1994).

Tousoulis et al., "Left Ventricular Function Coronary Artery Disease Progression Early After Coronary Bypass Grafting", Ann Thorac Surg, 58:857–863 (1994).

Turner et al., "Coronary Reoperation: Results of adding an internal mammary artery graft to a stenotic vein graft", Ann Thorac Surg, 58:1353–1355 (1994).

van Sterkenburg et al., "Triple Sequential Grafts Using IMA", J Thorac Cardivasc Surg, 104:60–65 (1992).

Wantanabe et al., "Third–time Coronary Artery Revascularization", Thorac Cardiovasc Surg, 41:163–166 (1993).

Wellens et al., "Theh Right Gastroepiploic Artery: An alternative conduit for myocardial revascularization", Acta Chir Belg, 91:54–58 (1991).

Witkop et al., "Gastric Perforation After Aorto–cornary Bypass Grafting with Right Gastroepiploic Artery", Ann Thorac Surg, 58:1170–1171 (1994).

Landreneau et al., "Video–Assisted Thoracic Surgery" Ann Thorac Surg, 54:800–807 (1992).

Meditech ®, Instructions for Use, "Occlusion Balloon Catheters", Rev. Mar. 1991, pp. 1–7.

Buckberg, G.D., "Strategies Logic of Cardioplegic Delivery to Prevent, Avoid, and Reverse Ischemic and Repofusion Damage", J Thorac Cardio Vasc Surg, 93:127–199 (1987).

Yamaguchi, A., "A Case fo a Reoperation Using a Balloon Catheter with Blocked Pars Ascendes Aortae", Kyobu Geka, 42(11):961–964 (1991).

Peters, W.A., "The Promiseof Cardioscopic Surgery", Austral As J. Cardiac Thorac Surg., 2(3):152–154 (1993).

Razi, D.M., "The Challenge of Calcific Aortitis", J Cardiac Thorac Surg, 8:102–107 (1993).

Ogawa, K., Aortic Arch Reconstruction without Aortic Cross–Clampign Using Separate Extracorporeal Circulation, J. Jpn. Assn Thorac Surg., pp. 2185–2190 1993).

Gundry et al., "A Comparison of Retrograde Cardioplegia Versus Antegrade Cardioplegia in the Presence of Coronary Artery Obstruction", Ann Thorac Surg. 38(2):124–127 (1984).

Lust et al., "Improved Protection of Chronically Inflow–Limited Myocardium with Retrograde Coronary Sinus Cardioplegia", Circulation III, 78(5):217–233 (1988).

Crooke et al., "Biventricular Distribution of Cold Blood Cardioplegic Solution Administered by Different Retrograde Techniques", J Cardiac Thorac Surg, 102(4):631–636 (1991).

Sabiston, D.C., Textbook of Surgery, $10^{th}$ Ed. pp. 2021–2023; 2114–2121 (1972).

Ishizaka, "Myocardial Protection by Retrograde Cardiac Perfusion with Cold Modified Krebs Solution through Coronary Sinus During Complete Ischemic Arrest for 120 min.", J. Jpn Assn Thorac Surg. 25(12):1592–1602 (1977).

Takahashi, M., "Retrograde Coronary Sinus Perfusion for Myocardial Protection in Aortic Valve Surgery", J Jpn Assn Thorac Surg 30(3):306–318 (1982).

Cosgrove, D.M., "Management of the Calcified Aorta: An Alternative Method fo Occlusion", Ann Thorac Surg. 36:718–719 (1983).

J.H. Foster and J.B. Threlkel, "Proximal Control of Aorta with a Balloon Catheter", Surg. Gynecology & Obstertrics, pp. 693–694 (1971).

H.G. Erath, Jr. and William S. Stoney, Jr., "Balloon Catheter Occlusion of the Ascending Aorta", Ann Thorac Surg., 35:560–561 (1983).

Coltharp et al., "Videothorascopy", Ann Thorac Surg, 53:776–9 (1992).

Mack et al.,"Present Role of Thoracoscopy in Diagnosis and Treatment Disease of the Chest", Ann Thorac Surg, 54:403–9 (1992).

Ozuner et al., "Creation of a Pericardial Window Using Thoracoscopic Techniques", Surg Gynecology & Obstetrics, 175:69–71 (1992).

Wakabayashi, A., "Expanded Applications of Diagnostic and Therapeutic Thoracoscopy", J. Thorac and Cardiovasc Surg, 102–721–3 (1991).

Berreklouw et al., "Does it Make Sense to Use Two Internal Thoracic Arteries?", Ann Thorac Surg, 59:1249–50 (1995).

Mack et al., "Video–Assisted Thoracic Surgery for the Anterior Approach to the Thoracic Spine", Ann Thorac Surg, 59:1100–6 (1995).

Rosenfeldt et al., "Topical Cardiac Cooling by Recirculation: Comparison of a Closed System Using a Cooling Pad with an Open System Using a Topical Spray", Ann Thorac Surg 34(2):138–145 (1982).

Dailey et al., "Clinical Comparisons of Methods of Myocardial Protection", J Thorac Cardiovasc Surg, 93(3):324–366 (1987).

Chocron et al., "The Y graft: Myocardial Revascularization with both Internal Thoracic Arteries", J Thorac Cardiovasc Surg, 108:736–740 (1994).

Green et al., "Five–Year Follow–Up of Microsurgical Multiple Internal Thoracic Artery Grafts", Ann Thorac Surg, 58:74–9 (1994).

Joyce et al., "Cardiac Reoperation in Patients with Bilateral Internal Thoracic Artery Grafts", Ann Thorac Surg, 58:80–5 (1994).

"Introducing the Vernick–Oetiker Hepatic Resection Clamp Patented: U.S. Pat. No. 5,203,786 (Model No. 69514)", 2 pps. by Mediflex, Division of Flexbar Machine Corp., Islands, New York 11722–2697.

Angelini, "A Simple, Inexpensive Method of Heart Retraction During Coronary Artery Bypass Surgery", Ann Thorac Surg, 46:246–247 (1988).

Galvin and Newman, "Circumflex Exposure Using a Cardiac Sling", Ann Thorac Surg., 49:833–834 (1990).

Janke, "Heart Support for Coronary Bypass Surgery Involving the Circumflex Artery System", J Thorac Card Surg, 883–884 (1974).

Kazama and Ishihara, "Fabric Heart Retractor for Coronary Artery Bypass Operations", Ann Thorac Surg, 55:1582–1583 (1993).

NDM EndoFlex Instruction Manual for 31–2000 and 31–3000 Series EndoFlex Snake Retractors, no date.

REMA Angled Thoracoscopy Instruments advertisements, no date.

Sakamoto et al., "New Cardiac Retractor for Epicardial Electrode Insertion Via Subxiphoid Approach", Ann Thorac Surg, 55:1025–1026 (1993).

Schurr et al., "Future Advances in Endoscopic Surgery", Part V, Chapter 47, pp. 342,347, 348.

Ueyama et al., "In Situ Right Internal Thoracic Artery Graft Via Transverse Sinus for Revascularization of Posterolateral Wall: Early Results in 116 Cases", J Thorac Card Surg., 112(3):731–736 (1996).

* cited by examiner

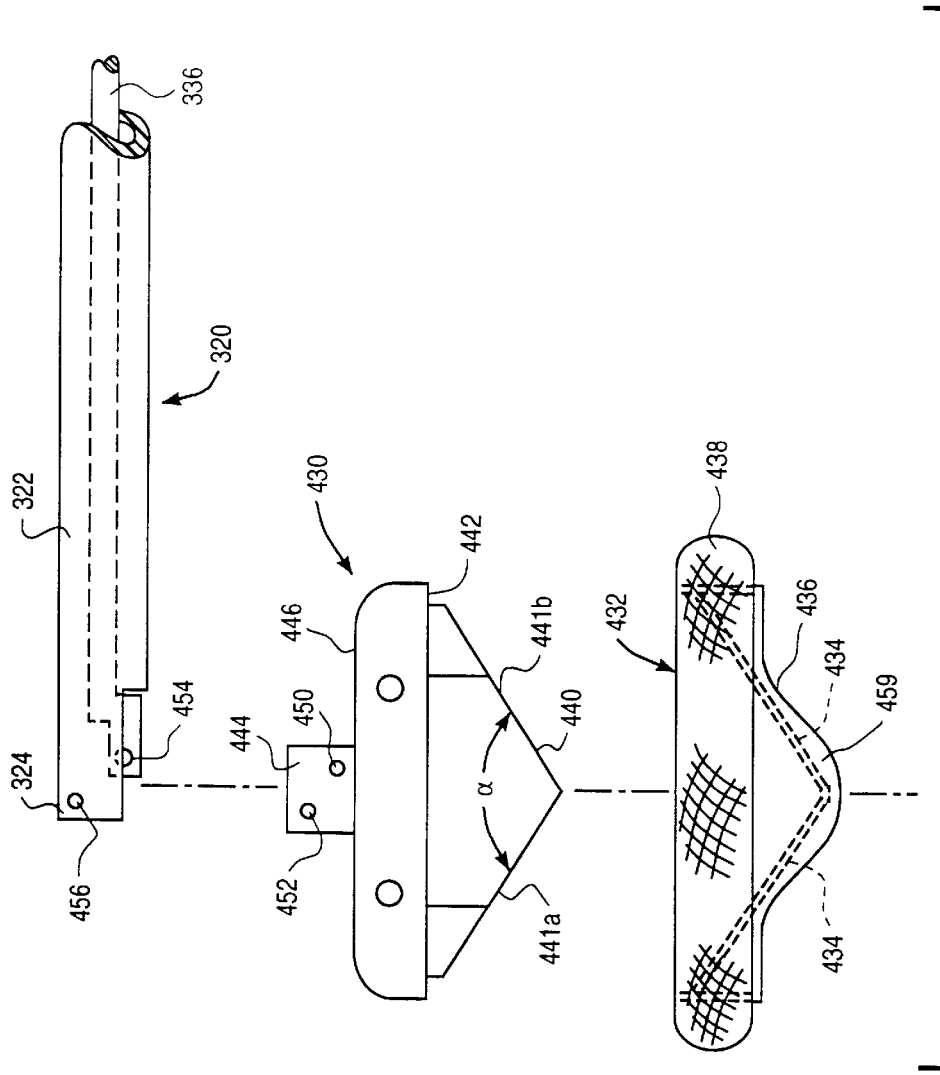
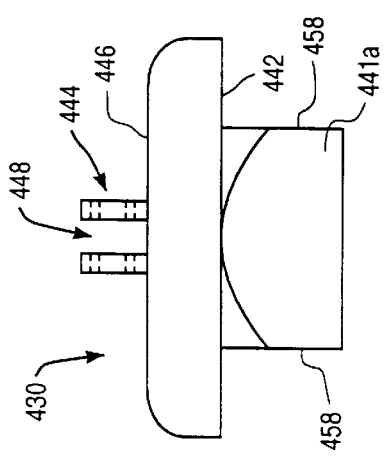
FIG. 33A
FIG. 33B

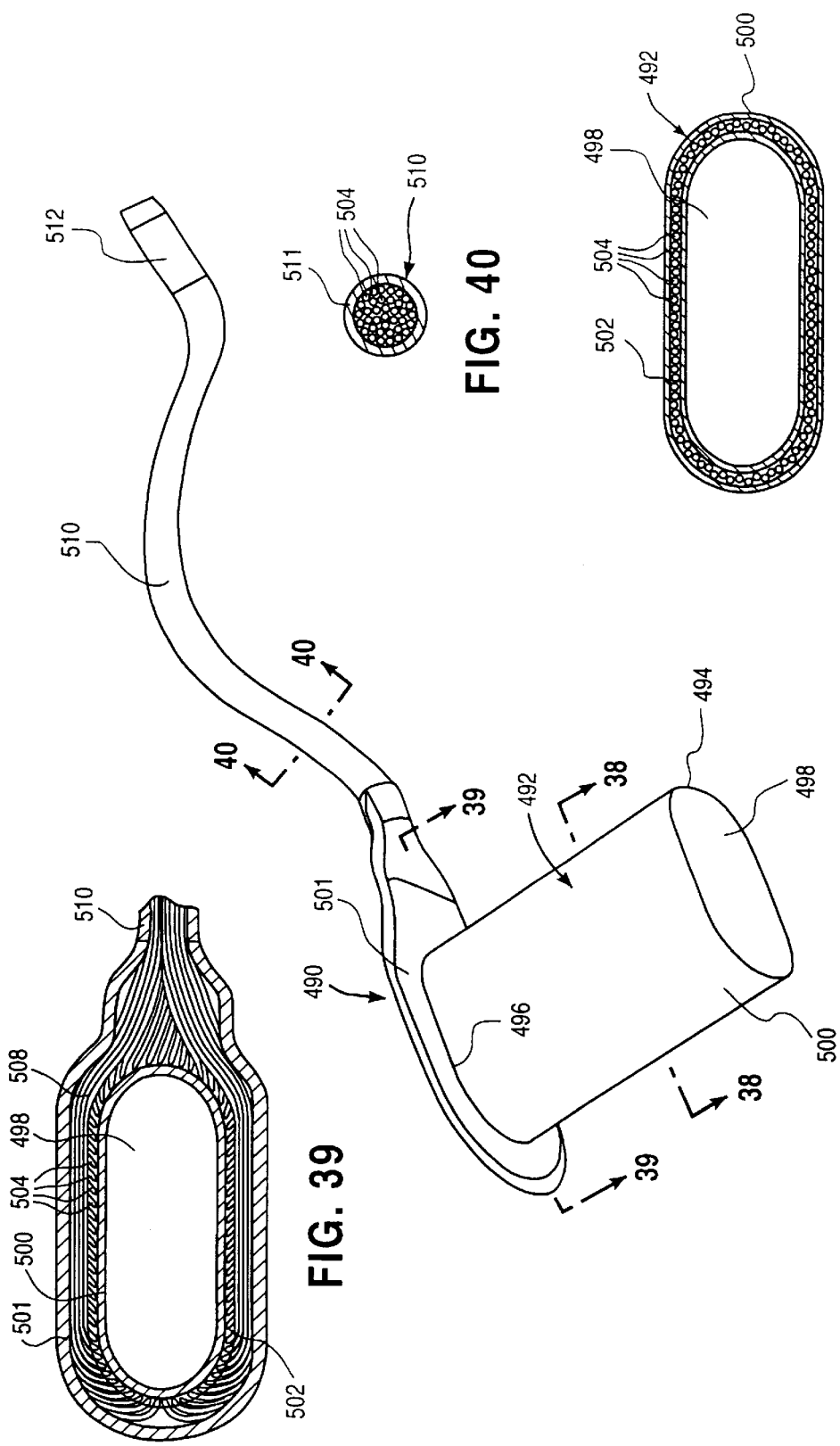

LENS-INVASIVE DEVICES AND METHODS FOR CARDIAC VALVE SURGERY

CROSS-REFERENCE TO RELATED APPLICATIONS

This application is a continuation of application Ser. No. 08/594,870, filed Jan. 31,1996, now U.S. Pat. No. 6,010,531, which is a continuation-in-part of Ser. No. 08/485,600, filed Jun. 7, 1995 now abandoned, which is a continuation-in-part of Ser. No. 08/281,962, filled Jul. 28, 1994 now abandoned, which is a continuation-in-part of Ser. No. 08/163,241, filed Dec. 6,1993 now U.S. Pat. No. 5,571,215, which is a continuation-in-part of Ser. No. 08/023,778, filed Feb. 22, 1993 now U.S. Pat. No. 5,452,733. This application is also a continuation-in-part of Ser. No. 08/486,941, filed Jun. 7, 1995 now U.S. Pat. No. 5,799,661. The complete disclosure of each of the above-referenced applications is incorporated herein by reference for all purposes.

FIELD OF THE INVENTION

The present invention relates generally to surgical instruments, and more specifically, to surgical instruments for less-invasive surgery of the heart and great vessels, especially instruments for repair and replacement of heart valves.

BACKGROUND OF THE INVENTION

The present invention is directed to devices and techniques for the surgical treatment of heart valve disease, and particularly aortic valve disease. The aortic valve separates the left ventricle of the heart from the aorta, which carries oxygenated blood to the arterial system. Normally, when the left ventricle contracts during systole, the aortic valve opens to allow blood to flow into the aorta. During diastole, when the left ventricle returns to its uncontracted state, the aortic valve closes to prevent blood from flowing from the aorta back into the heart.

In aortic valve disease, the aortic valve is compromised due to calcification of the valve leaflets, congenital deformation of the valve, or other conditions such that the valve does not completely open or close normally. As a result, the valve restricts blood flow out of the heart during systole, or the valve allows blood flow back into the heart during diastole. If the condition becomes sufficiently severe, surgical treatment is frequently required.

Various surgical techniques have been used to repair aortic valves. In conventional "open-chest" approaches, a large opening is formed in the chest—known as a sternotomy or thoracotomy—the patient's heart is arrested while circulation is supported by a cardiopulmonary bypass system, an incision is formed in the aorta, and instruments are then used to decalcify the valve, to separate valve leaflets which are fused together, or to constrict the annulus of an enlarged valve. Less-invasive approaches to valve repair have also been proposed. Balloon valvuloplasty, for example, involves the use of a balloon catheter threaded from a peripheral artery into the aorta, and expansion of a balloon within the calcified aortic valve to separate the valve leaflets while the heart remains beating. Unfortunately, aortic valve repair techniques have not had long-lasting success in preventing recurrence of the disease, and eventual replacement of the valve is frequently required.

The most widely-accepted surgical technique for the treatment of severe aortic valve disease is aortic valve replacement. In aortic valve replacement surgery, the diseased aortic valve is replaced with a prosthetic valve, homograft, allograft, or other type of replacement valve. Conventional aortic valve replacement techniques require a sternotomy or thoracotomy to be formed so as to provide access into and visualization of the chest cavity. The patient is placed on cardiopulmonary bypass, and the heart is stopped using an aortic cross-clamp to block blood flow through the aorta while a cardioplegic fluid is injected into the aorta upstream of the cross-xclamp or into the coronary sinus on the venous side of the heart. An incision is then made in the ascending aorta near the aortic valve, and the native valve leaflets are removed using surgical scissors inserted through the aortic incision. Specialized instruments may also be used to debride the valve annulus. A replacement valve is then sutured in place at the native valve position.

While aortic valve replacement is frequently effective in treating aortic valve disease and can add ten or more years to the life of a patient having the disease, the procedure also suffers from significant drawbacks surrounding the invasiveness and trauma of the surgery. The large thoracotomy required by the procedure is highly invasive, produces a great deal of pain, heightens the risk of infection and other complications, increases costs, and lengthens hospital stay considerably.

What is needed, therefore, are devices and techniques for the surgical treatment of aortic valve disease, especially for performing aortic valve replacement, which do not suffer from the drawbacks of conventional open-chest aortic valve surgery. Most desirably, the devices and techniques should obviate the need for a sternotomy and minimize the size of any necessary thoracic incisions to eliminate the pain, trauma, risks, costs, and lengthy recovery time associated with conventional aortic valve surgery. At the same time, the devices and techniques should facilitate replacement of a diseased aortic valve with the same types of replacement valves which currently enjoy wide acceptance for aortic valve replacement, including mechanical valves, bioprosthetic valves, homografts, allografts, and others.

SUMMARY OF THE INVENTION

The invention provides devices and methods for performing heart valve surgery which eliminate the need for a median sternotomy or other type of thoracotomy. The devices and methods are particularly advantageous in that they facilitate surgical repair or replacement of a heart valve in a manner analogous to the widely-accepted surgical techniques used in open-chest valve repair or replacement, yet without the invasiveness, pain, risks, and recovery time of conventional techniques. Advantageously, the devices and methods facilitate replacement of a diseased heart valve using various types of commercially-available replacement valves with proven safety and effectiveness. The devices and methods of the invention are perhaps most useful for the repair and replacement of the aortic valve, but may be used for the surgical treatment of any of the valves of the heart, as well as in other surgical procedures within the heart and great vessels of the thorax.

In one aspect of the invention, a method is provided for accessing an internal chamber of a patient's heart through a vessel in fluid communication with the chamber. The method includes visualizing the vessel through a percutaneous access port between two adjacent ribs. An instrument is positioned into an inner lumen of the vessel through a penetration in a wall of the vessel. The proximal end of the instrument extends out of the patient's chest through a percutaneous access port between the ribs, and the proximal end of the instrument is then manipulated to position the distal end of the instrument through the vessel and into the internal chamber of the heart. With the instrument within the internal chamber, various types of inspection, diagnostic and interventional procedures may then be performed. All manipulations of the instrument are performed with the surgeon's hands outside of the patient's chest, and none of the ribs or the sternum are cut or removed during each step. Preferably, in fact, none of the ribs or the sternum are significantly retracted from their natural undeflected positions during the procedure. Visualization is accomplished either by looking directly into the chest through an access port between the ribs, by introducing a thoracoscope through such an access port and viewing a video image of the vessel and heart on a monitor, or by using other available less-invasive visualization devices.

In a preferred embodiment, the vessel is the aorta, the chamber is the left ventricle of the heart, and the distal end of the instrument is positioned into the aorta, through the aortic valve, and into the left ventricle. The instrument may then be used to perform a procedure in the heart or on the aortic valve itself. For example, the instrument could be used for repairing a diseased aortic valve, and may comprise a debridement device for removing calcium from the valve annulus or leaflets, a scissors for incising the leaflet commissures to separate the leaflets, a cutting device for resecting the valve leaflets, or a needle driver for applying a suture to the valve annulus to reduce the diameter of the valve.

In a particularly preferred embodiment, the instrument is used in the replacement of a diseased aortic valve. The instrument may be a scissors, rongeur, knife or other cutting instrument for removing the native valve leaflets, or a needle driver or other device for applying sutures to the native valve annulus which are used to secure a replacement valve at the aortic valve position. The instrument could alternatively comprise a valve sizing device for measuring the size of the native valve annulus, or a valve delivery instrument for positioning a replacement valve at the aortic valve position. In any case, the instrument extends from the left ventricle out of the chest through a percutaneous access port between two ribs, and is manipulated entirely from outside of the chest.

As another alternative, the instrument may comprise any of a variety of devices for performing diagnostic or interventional procedures within the heart, such as an angioscope or other endoscopic visualization device, an electrophysiological mapping or ablation device, or a laser for transmyocardial revascularization. Additionally, the instrument could be used to repair or replace other valves of the heart. For example, the mitral valve could be repaired or replaced by positioning the instrument through the aorta and left ventricle to the mitral position (and through the mitral valve into the left atrium if necessary). Or, an instrument could be positioned through the superior vena cava or the inferior vena cava into the right atrium to perform a procedure on the right side of the heart, including repair or replacement of the tricuspid valve between the right atrium and right ventricle, or repair or replacement of the pulmonary valve between the right ventricle and the pulmonary artery. Various other procedures may also be performed according to the method of the invention, including pulmonary thrombectomy, the Cox "maze" procedure for treatment of atrial fibrillation, and repair of congenital defects such as atrial and ventricular septal defects or patent ductus arteriosus.

In many of the procedures which may be performed using the methods of the invention, the patient is placed on cardiopulmonary bypass and the heart is arrested. First, general anesthesia is administered. To establish cardiopulmonary bypass, an arterial cannula is placed into a peripheral artery, usually a femoral artery, and a venous cannula is placed in a peripheral vein, usually a femoral vein. The arterial and venous cannulae are connected to a cardiopulmonary bypass pump and oxygenator, allowing deoxygenated blood to be withdrawn from the venous system through the venous cannula, oxygenated, and then pumped back into the patient's arterial system through the arterial cannula.

The heart may then be arrested in any of several ways. In an endovascular technique, an aortic catheter is introduced into a peripheral artery selected from among the femoral, brachial or subclavian arteries. The aortic catheter is advanced transluminally into the ascending aorta, and an expandable member such as a balloon is expanded in the ascending aorta to block blood flow through the aorta. A cardioplegic fluid is then delivered into-the ascending aorta upstream of the expandable member so as to perfuse the myocardium via the coronary arteries. Alternatively, a thoracoscopic aortic occlusion device may be used to arrest the heart. The thoracoscopic aortic occlusion device may be an external clamp positionable through a percutaneous access port between two ribs and around the exterior of the aorta, the clamp being movable between an open position and a closed position in which it clamps the aorta to occlude the aortic lumen. A cardioplegic fluid is then delivered into the aorta upstream of the clamp, either through a cannula penetrating the aortic wall and extending out of the chest through an intercostal access port, or through an endovascular catheter extending into the ascending aorta from a peripheral artery. The thoracoscopic aortic occlusion device may alternatively comprise a shaft having an expandable member such as a balloon mounted to its distal end which is configured to be introduced into the aorta through a small incision or puncture in the aortic wall. The expandable member may be expanded within the aorta to occlude the aortic lumen, and a cardioplegic fluid then delivered upstream of the clamp through either a thoracoscopic cannula or endovascular catheter.

In many cases, in order to maintain cardioplegic arrest, it will be desirable to deliver cardioplegic fluid to the myocardium in a retrograde manner via the coronary sinus instead of or in addition to antegrade delivery from the ascending aorta. In these cases, an endovascular catheter is introduced transluminally into the coronary sinus, which drains into the right atrium of the heart, from a peripheral vein such as the femoral, subclavian or internal jugular vein. The endovascular catheter preferably has a balloon or other occluding member on its distal end for occluding the coronary sinus during delivery of cardioplegic fluid. Usually, the occluding member is expanded while cardioplegic fluid is delivered, then contracted to allow fluid to drain into the right side of the heart from the capillary beds feeding the myocardium.

With the heart arrested and circulation of blood supported by cardiopulmonary bypass, the patient is prepared for a surgical procedure conducted in accordance with the principles of the invention. One such procedure is replacement of the aortic valve.

In a method of aortic valve replacement according to the invention, a valve prosthesis is positioned through a percutaneous access port between two adjacent ribs and through an incision in a wall of the aorta using a first instrument. The valve prosthesis is then attached at the aortic valve position between the left ventricle and the aorta using at least a second instrument. All instruments used in the procedure are manipulated only from outside of the chest, and neither the ribs nor the sternum are cut or removed during the procedure. Visualization of the vessel and heart is accomplished, as described above, by direct vision through an access port, or using a thoracoscope or other minimally-invasive visualization device.

In a preferred embodiment, the first instrument comprises a delivery handle which is coupled to the valve prosthesis, or to a holder on which the valve prosthesis is mounted. The delivery handle is configured to allow the valve prosthesis to be introduced into the chest through the percutaneous access port and has a length selected to reach the aortic valve position from outside of the chest. Usually, the valve prosthesis is introduced from the first, second, third, or fourth intercostal space on the anterior side of the chest, and the delivery handle is at least about 20 cm in length. In a specific embodiment, the valve prosthesis is movably coupled to the delivery handle such that it may be positioned through the access port between the ribs in a first orientation, then re-oriented within the chest relative to the delivery handle into a second orientation suitable for attachment at the aortic valve position. Preferably, the delivery handle has an actuator on its proximal end to allow the valve prosthesis to be reoriented by moving the actuator outside of the patient's chest.

The valve prosthesis is preferably coupled to the delivery handle in such a way that it may be positioned through an intercostal space without removing or retracting the ribs significantly. In a preferred embodiment, the valve prosthesis is mounted such that an axis extending axially through the middle of the sewing ring of the valve prosthesis is approximately perpendicular to the longitudinal axis of the delivery handle. In this way, the profile of the valve prosthesis and delivery handle in a plane perpendicular to the longitudinal axis of the delivery handle is minimized. For some types of replacement valves, however, even in this orientation, the profile of the valve and handle will be large enough that some minor retraction of the adjacent ribs may be required to allow the valve to be introduced into the chest without risking damage to the valve.

The percutaneous access port through which the valve prosthesis is positioned may comprise a puncture or incision through the chest wall between the ribs which does not involve cutting or removing the ribs or the sternum adjacent to the incision. Preferably, no significant retraction or displacement of the ribs or sternum will be necessary. In most cases, the tissue adjacent to the access port will need to be retracted or separated to provide an opening into the chest which will not interfere with introduction of the valve prosthesis and through which the surgeon may view the chest cavity. For this purpose, the invention provides a retraction device particularly well-suited for aortic valve replacement. In a preferred embodiment, the retraction device comprises a cannula having a distal end suitable for placement between the ribs into the chest, a proximal end, and a passage therebetween configured to allow the valve prosthesis to be easily passed through it. In a preferred configuration, the passage in the cannula has a cross-sectional height which is substantially greater than its cross-sectional width, preferably at least about 1.5 times the cross-sectional width. In this way, the cross-sectional height may be large enough to accommodate the outer diameter of the valve prosthesis in the passage, while the cross-sectional width is small enough to fit between the ribs without significant retraction (yet being large enough to accommodate the height of the valve prosthesis when mounted to the delivery handle).

If a replacement valve having a larger profile is to be used requiring some minor retraction of ribs, the retraction device of the invention may be adjustable in width to provide a slightly larger passage into the chest while the valve is introduced, deflecting the ribs adjacent to the access port as needed. Once the replacement valve is within the chest cavity, the retraction device may be returned to a smaller width in which the ribs are in their natural, undeflected positions for the remainder of the procedure.

The retraction device of the invention may further include a suture organizer mounted to it for arranging the sutures used to secure the valve prosthesis in the aortic valve position. In a preferred embodiment, the suture organizer is mounted to the proximal end of the cannula through which the valve prosthesis is positioned, whereby a plurality of sutures may be drawn out of the chest cavity through the passage in the cannula and placed in spaced-apart locations on the suture organizer. The suture organizer may comprise, for example, a ring having a plurality of radial slots arranged about its perimeter each of which is configured to receive and retain a suture thread.

Usually, the native valve leaflets are excised from the native annulus and any calcium or other debris on the annulus is removed before a replacement valve is implanted. To remove the valve leaflets, thoracoscopic scissors and forceps may be introduced through a percutaneous access port and used to cut the leaflets from the annulus. Specialized thoracoscopic debridement devices, such as rongeurs having an inner lumen through which suction may be applied, are then used to cut away calcific deposits and other undesirable matter from the surface of the valve annulus. During this process a filter or trap may be placed through the aortic valve into the left ventricle to catch any debris which may be released.

In most cases, the native valve annulus must be measured to ascertain the appropriate size of the valve prosthesis to be used. This is accomplished by utilizing a specialized valve sizing device which may be introduced through a percutaneous access port and positioned adjacent to or advanced through the native annulus. The sizing device preferably includes an elongated handle with a sizing disk of a known size at its distal end which may be compared to or positioned within the native annulus. The sizing disk may be adjustable in diameter to measure a range of sizes, may include markings for visual identification of the size of the annulus, or may be interchangeable with larger and smaller sizing disks to allow multiple sizes to be tried until the proper one is found. The sizing disk is mounted to the distal end of the handle in such a way as to be positionable into the chest without retracting or removing ribs, and is preferably pivotably attached to the handle so as to be movable into a low profile orientation for introduction, or is collapsible for introduction and then expandable for sizing the valve annulus.

A variety of different replacement valves may be implanted using the devices and methods of the invention, including mechanical prostheses, bioprostheses, homografts and allografts. Advantageously, the invention facilitates the use of many of the clinically-proven replacement valves currently used in open-chest valve replacement without modification of these valves and without the need for removal or significant retraction of the ribs.

The replacement valve may be secured at the native valve position in various ways, but is preferably secured using sutures. The sutures are applied to the aortic valve annulus using elongated thoracoscopic needle drivers or other known types of thoracoscopic suture placement devices positioned through a percutaneous access port. Usually, a plurality of sutures are applied to the annulus, drawn out of the chest cavity, and then applied to the sewing ring of the valve prosthesis outside of the chest. The valve prosthesis is then slid along the sutures through the access port and placed against the native valve annulus using the delivery handle or other appropriate thoracoscopic instrument. A knot is formed in each suture outside of the chest, and the knot is pushed along the suture through the access port and against the sewing ring of the valve prosthesis using a thoracoscopic knot pusher. The free ends of the suture are then trimmed using thoracoscopic scissors.

For securing bioprosthetic valves and other types of replacement valves, it may be desirable to use a single suture to form a running stitch between the sewing ring and the native valve annulus. In these cases, with the valve held in place at or near the aortic position using the delivery handle, thoracoscopic needle drivers may be positioned through an access port and used to drive a needle alternately between the native annulus and the sewing ring of the replacement valve. The suture is then tied off and trimmed using thoracoscopic instruments.

Once the replacement valve has been secured at the aortic valve position, the aortic incision must be closed. Thoracoscopic needle drivers are introduced through a percutaneous access port and used to drive a suture back and forth across the incision from end to end in a running stitch. The suture is then tied off and trimmed.

With the aortic incision closed, the patient's heart is restarted by removing the aortic occlusion device, whether an external clamp, endovascular aortic occlusion catheter, or other means, from the ascending aorta. If placed through a puncture in a wall of the aorta, the puncture is closed with a purse-string suture or running stitch using thoracoscopic needle drivers. Warm oxygenated blood delivered to the arterial system by the arterial cannula is thereby allowed to flow into the ascending aorta and to perfuse the myocardium via the coronary arteries. Normal heartbeat will ordinarily resume spontaneously. If not, electrical defibrillation may be administered. Once normal heartbeat has resumed, any retractors, trocars, or other devices in the percutaneous access ports are removed, and chest incisions are closed with sutures or adhesive strips. The patient is gradually weaned from cardiopulmonary bypass, all arterial and venous cannulae are removed, and arterial and venous punctures are closed. The patient is then recovered from anesthesia.

A further understanding of the nature and advantages of the invention will become apparent from the following detailed description taken in conjunction with the drawings.

BRIEF DESCRIPTION OF THE DRAWINGS

FIG. 33A is a side assembly view of a distal portion of the delivery handle and valve holder of FIG. 32.

FIG. 33B is an end view of the valve holder of FIG. 32.

FIG. 37 is a perspective view of an access port and illumination device constructed in accordance with the principles of the invention.

FIGS. 38–40 are cross-sections taken along the lines 38—38, 39—39 and 40—40, respectively, of FIG. 37.

DETAILED DESCRIPTION OF SPECIFIC EMBODIMENTS

Specific embodiments of the devices and methods of the invention will now be described in connection with aortic valve replacement procedures. However, it will be understood to those of ordinary skill in the art that a wide variety of procedures may be performed on a variety of body structures without departing from the scope of the invention. These include, in addition to surgery of the aortic valve via the aorta, interventions in the coronary arteries, left ventricle, mitral valve, left atrium, or pulmonary vein via the aorta, interventions in the right atrium, tricuspid valve, right ventricle, pulmonary valve or pulmonary artery via the superior vena cava or inferior vena cava, as well as interventions in various other organs via vessels in communication with those organs. The types of interventions which can be performed include not only aortic valve repair and replacement, but catheter interventions in the coronaries such as angioplasty, atherectomy, stent placement or endoarterectomy, electrophysiological interventions within the heart such as mapping and ablation, transmyocardial revascularization using a laser placed within the heart, repair of septal defects and patent ductus arteriosus using patch placement or other defect closure devices placed in the right or left chambers of the heart, repair or replacement of the mitral, tricuspid or pulmonary valve including placement of annuloplasty rings and prosthetic valves, reattachment of chordae tendonae, commissurotomy, and quadrangular resection, incision of the atrial or ventricular wall for the performance of a Cox maze procedure in the treatment of atrial fibrillation, and other procedures. The principles of the invention will apply to the performance of these procedures in much the same way as to the performance of aortic valve replacement, which is now described with reference to FIGS. 1–36.

Figure 1:
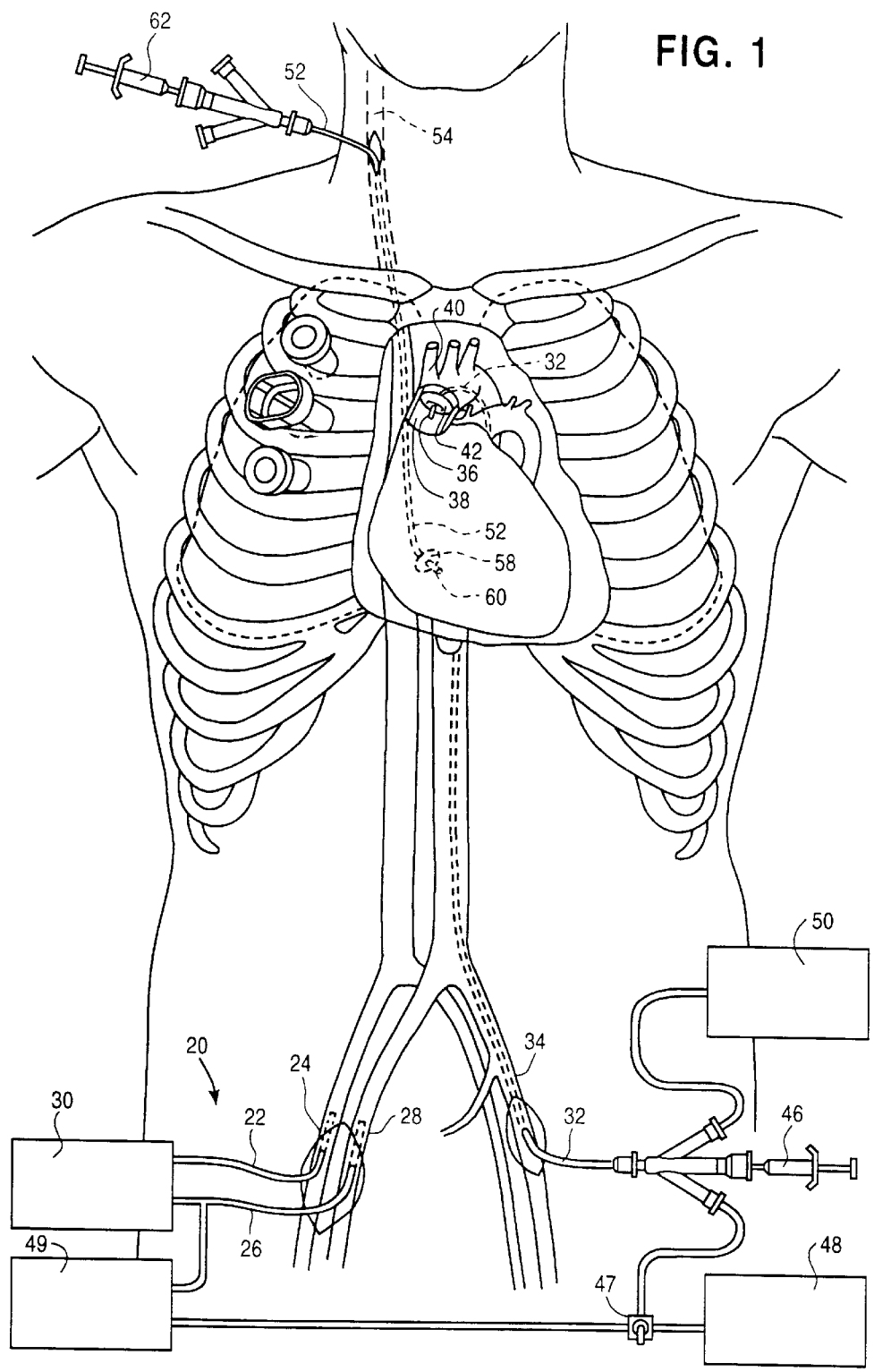
FIG. 1 is an anterior view of a patient's chest schematically illustrating an endovascular system for inducing cardioplegic arrest and establishing cardiopulmonary bypass according to the invention.

The patient is first prepared for aortic valve surgery by putting the patient under general anesthesia, establishing cardiopulmonary bypass (CPB) and inducing cardioplegic arrest. General anesthesia is induced in a conventional manner. A preferred technique for accomplishing CPB and cardioplegic arrest which does not require a sternotomy, thoracotomy, or other opening in the patient's chest is illustrated in FIG. 1. Additional aspects of the systems and methods for inducing cardioplegic arrest described here may be found in patent application Ser. Nos. 08/282,192, filed Jul. 28, 1994, now U.S. Pat. No. 5,584,803 and 08/486,216, filed Jun. 7, 1995, now U.S. Pat. No. 5,766,151, the complete disclosures of which are hereby incorporated herein by reference.

A cardiopulmonary bypass system 20 includes a venous cannula 22 which is placed in a femoral vein 24 in the groin area or in another peripheral vein such as an internal jugular vein or subclavian vein, located in the neck. While illustrated in a shorter configuration, the venous cannula may be long enough to extend from the femoral vein into the inferior vena cava, into the right atrium of the heart or through the right atrium into the superior vena cava. The system also includes an arterial return cannula 26 placed in a femoral artery 28 or in another peripheral artery such as the subclavian or brachial artery in the neck or armpit. The arterial return cannula 26 is generally long enough so that it extends sufficiently into the femoral artery to avoid backing out of the artery but as short as possible to reduce damage to blood delivered through the arterial return cannula. Both venous cannula 22 and arterial return cannula 26 are configured to be placed into the femoral vein and femoral artery, respectively, either by surgical cut-down, or by a percutaneous technique such as the Seldinger technique.

Venous cannula 22 and arterial return cannula 26 are connected to a CPB pump and oxygenator 30 of well-known construction. CPB pump and oxygenator 30 oxygenates the deoxygenated blood withdrawn from the patient's venous system through venous cannula 22, and pumps the oxygenated blood back into the patient's arterial system via arterial return cannula 26. In this way, circulation and re-oxygenation of the patient's blood may be maintained while the heart is temporarily arrested.

Figure 2:
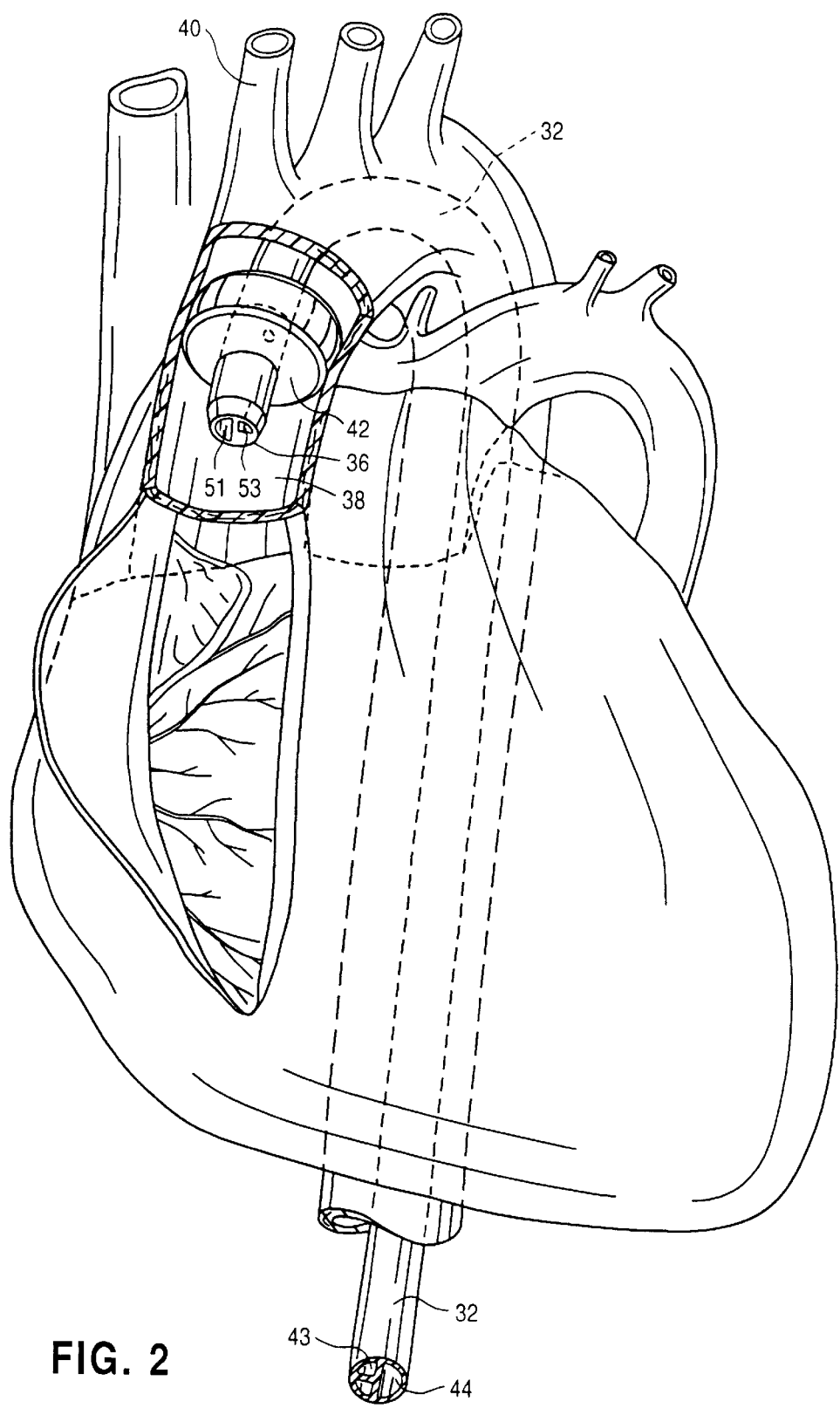
FIG. 2 is a close-up view of a patient's heart and aorta showing the placement of an endoaortic catheter in the system of FIG. 1.

Cardioplegic arrest may be induced using any of several techniques. One preferred technique is illustrated in FIGS. 1 and 2. In this technique, an endoaortic catheter 32 is introduced by surgical cut-down or by a percutaneous technique into a peripheral artery, which may be the femoral artery 34 as illustrated, or a brachial or subclavian artery. Endoaortic catheter 32 is configured to be advanced transluminally, usually over a guidewire (not shown), from femoral artery 34 into the aorta until its distal end 36 is positioned in the ascending aorta 38 between the coronary ostia (not shown) just downstream of the aortic valve and the brachiocephalic artery 40. Endoaortic catheter 32 has an expandable member 42 mounted near its distal end 36 which, as shown in FIG. 2, is configured to expand into sealing engagement with the inner wall of the ascending aorta 38 to block blood flow through the aorta without occluding either brachiocephalic artery 40 or the coronary ostia. In a preferred embodiment, expandable member 42 is an elastomeric balloon in communication with an inflation lumen 43 extending through endoaortic catheter 32 to a delivery device such as syringe 46 for delivering an inflation fluid such as saline or radio-opaque contrast solution to expand expandable member 42 until completely occluding the aorta. The elastomeric balloon preferably is short in the axial direction, being disc-shaped (a short cylinder), donut-shaped (toroidal), ellipsoidal, or other shortened shape to minimize the amount of the ascending aorta which is occupied by the balloon so that the surgeon has the maximum room to work upstream of the balloon. In one embodiment, expandable member 42 has an axial length between its proximal and distal ends of about 1–40 mm, preferably about 1–20 mm, and an expanded outer diameter in the radial direction of about 10 to 60 mm, preferably about 30–40 mm.

In a particularly preferred embodiment, arterial return cannula 26 includes an additional hemostatic port (not shown) at its proximal end that allows endoaortic catheter 32 to be slidably positioned through the blood return lumen of the arterial return cannula. Arterial return cannulae having such a configuration are disclosed in copending application Ser. No. 08/282,192, filed Jul. 28, 1994, now U.S. Pat. No. 5,584,803, which is incorporated herein by reference.

With expandable member 42 occluding the ascending aorta 38, a cardioplegic fluid is delivered from a cardioplegic fluid supply 48 through a delivery lumen 44 in endoaortic catheter 32 and a port 51 at its distal end 36 into the ascending aorta distal to expandable member 42 so that the cardioplegic fluid flows into the coronary arteries to perfuse the myocardium. The cardioplegic fluid preferably includes a cardioplegic agent such as potassium chloride mixed with blood and cooled to a low temperature, e.g. 5–20° C. Upon perfusion of the myocardium with cardioplegic fluid, heart contractions will quickly cease. Circulation of oxygenated blood to organs and tissues other than the heart is maintained by cardiopulmonary bypass system 20. Expandable member 42 prevents the oxygenated blood delivered by arterial return cannula 26 from reaching the coronary arteries, which would allow the blood to perfuse the myocardium and revive the heart.

Periodically, it may be necessary to remove fluids from the ascending aorta 38 during the procedure. Such fluids may be withdrawn through delivery lumen 44 of endoaortic catheter 32 and diverted through a valve 47 to a filter and recovery system 49, which removes impurities from the blood and directs the blood to cardiopulmonary bypass system 20 where it is delivered back into the arterial system. Alternatively, a separate cardiotomy suction probe may be introduced through an access port and through the aortic wall to remove such fluids. Endoaortic catheter 32 preferably also includes a pressure port 53 near its distal end 36 in communication with a pressure lumen extending to the proximal end of the catheter where it may be connected to a pressure measurement device 50, allowing pressures in the ascending aorta distal to expandable member 42 to be monitored during the procedure.

In addition to delivery of cardioplegic fluid in the "antegrade" manner via endoaortic catheter 32 as just described, it is usually desirable to deliver cardioplegic fluid in a "retrograde" manner through the coronary sinus during the aortic valve replacement procedure. For this purpose, a coronary sinus catheter 52 is placed into a peripheral vein 54, preferably the internal jugular vein or subclavian vein in the neck, and advanced through the superior vena cava into the right atrium, where it is maneuvered into the coronary sinus (not illustrated). Coronary sinus catheter 52 has a balloon or other expandable member 58 near its distal end 60 which may be expanded by means of a syringe 62 to occlude the coronary sinus during fluid delivery. A delivery lumen (not pictured) extends through the coronary sinus catheter 52 to a port at its distal end 60 to allow delivery of a cardioplegic fluid, which will usually be similar to that described above used in antegrade delivery. Coronary sinus catheter 52 may also include a pressure port near distal end 60 and a pressure lumen extending to its proximal end for monitoring pressure distal to expandable member 58. Other aspects of coronary sinus catheters and retrograde cardioplegia techniques useful in connection with the present invention are disclosed in copending application Ser. No. 08/372,741, filed Jan. 12, 1995, now U.S. Pat. No. 5,558,644, which is hereby incorporated herein by reference.

In a preferred technique, after an initial infusion of cardioplegic fluid through endoaortic catheter 32 to induce cardioplegic arrest, most subsequent infusions are performed retrograde through coronary sinus catheter 52. To maintain cardioplegic arrest, cardioplegic fluid is preferably delivered in periodic infusions at, for example, 600 ml volumes delivered in about 120 to 180 seconds at 15 minute intervals. Between infusions, expandable member 58 of coronary sinus catheter 52 is preferably deflated to allow fluid to drain from the coronary sinus.

In an alternative technique for inducing cardioplegic arrest, devices are introduced thoracoscopically through access ports between the ribs to occlude the ascending aorta and, optionally, to deliver cardioplegic fluid into the ascending aorta upstream of the occluded area. In these thoracoscopic techniques, the pericardium is first opened to expose the ascending aorta. As illustrated in FIG. 3A, several access ports 71, such as trocar sleeves or other tubular cannulae, are placed in intercostal spaces I between ribs R. A thoracoscope 73 of conventional construction and having a video camera 75 mounted to its proximal end may be placed through one of access ports 71 for visualizing the procedure, or the surgeon may look directly into the chest through one of access ports 71. Thoracoscopic scissors 77 and graspers 79 are introduced through access ports 71 and used to create an incision 81 approximately 4–10 cm in length in the anterior side of the pericardium 83 overlying the aorta 85 so that the ascending aorta 87 and upper anterior side of the heart 89 are exposed. Thoracoscopic scissors 77 and graspers 79 may have any of various well-known constructions, including those described in copending application Ser. No. 08/194, 946, filed Feb. 14, 1994, now U.S. Pat. No. 5,501,698, which is hereby incorporated herein by reference.

Figure 3:
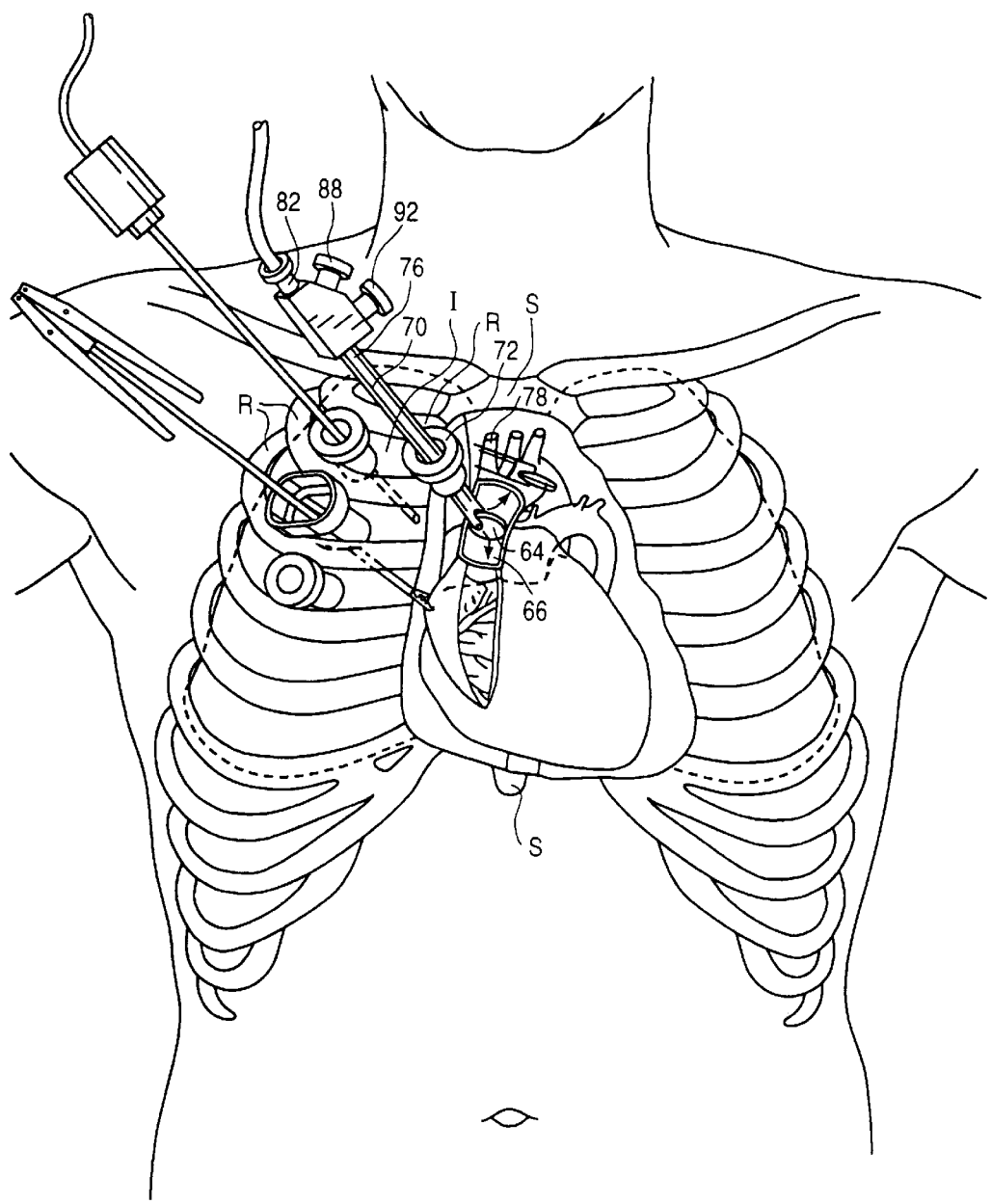
FIG. 3 is an anterior view of a patient's chest schematically illustrating a first embodiment of a thoracoscopic system for inducing cardioplegic arrest and establishing cardiopulmonary bypass according to the invention.
Figure 3A:
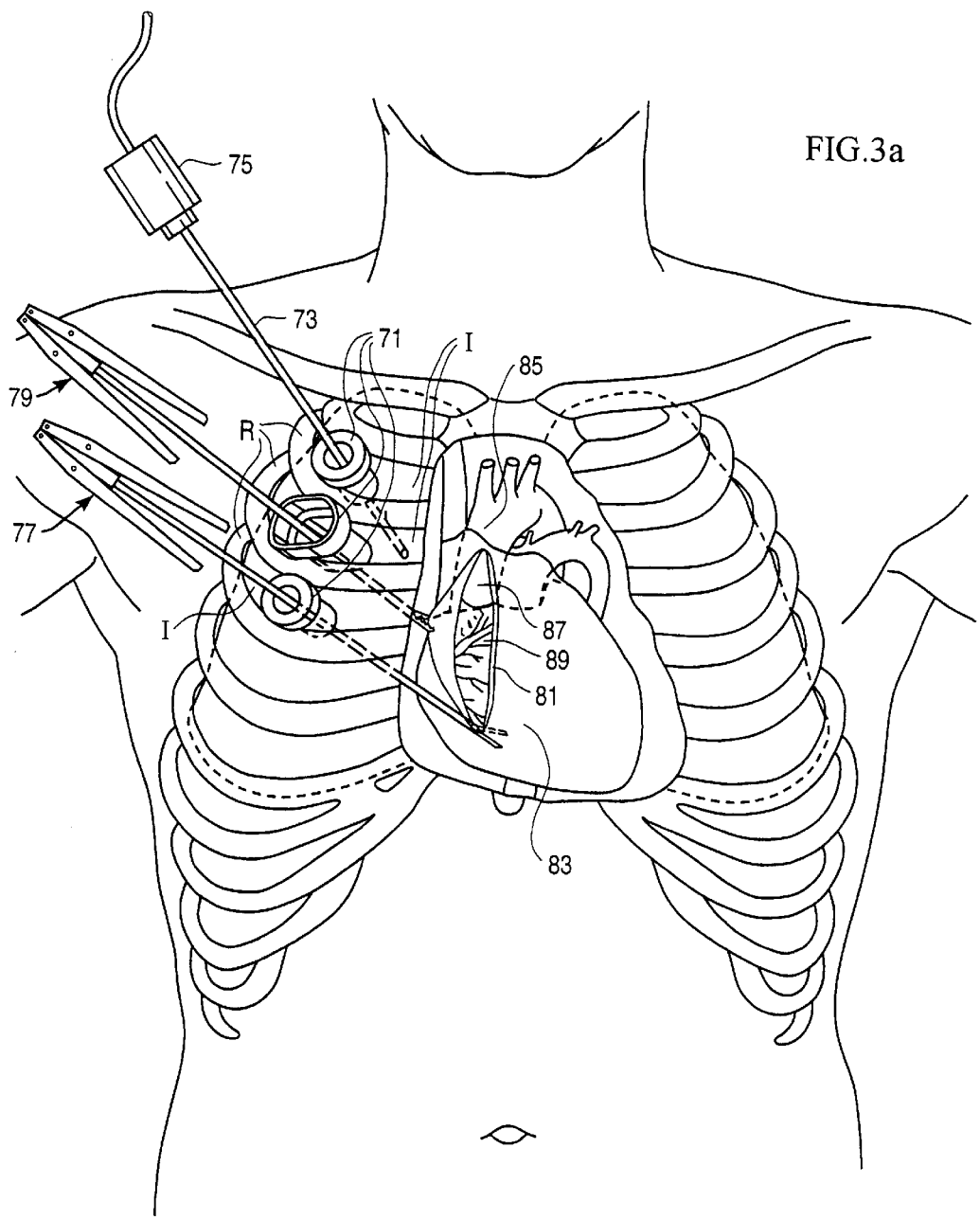
FIG. 3A is an anterior view of a patient's chest schematically illustrating a technique of gaining access to the aorta according to the invention.
Figure 4:
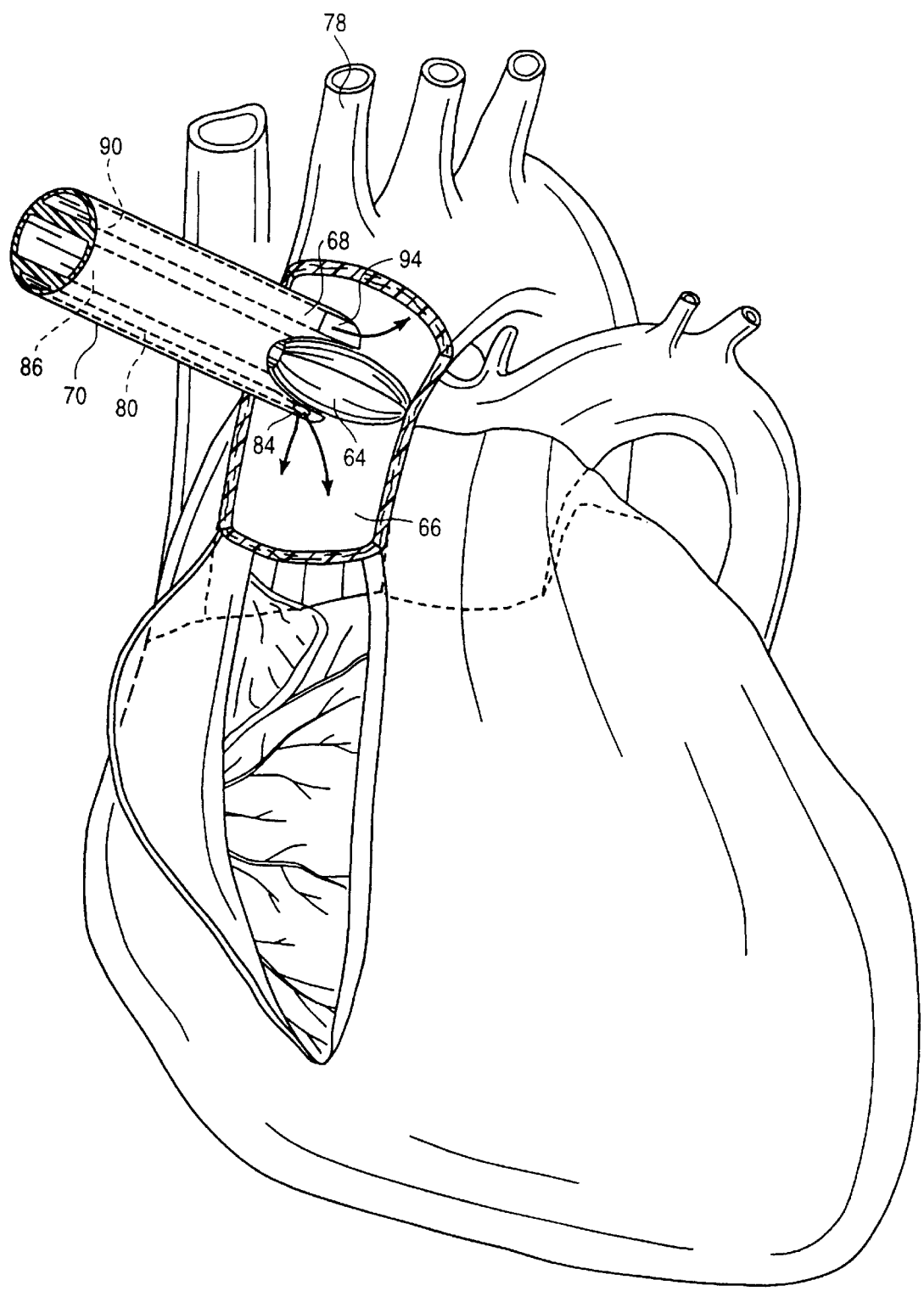
FIG. 4 is a close-up view of a patient's heart and aorta illustrating the placement of a thoracoscopic balloon cannula in the system of FIG. 3.

In a first embodiment of a thoracoscopic technique for arresting the heart, illustrated in FIGS. 3–4, an expandable member 64 such as an elastomeric balloon is positioned in the ascending aorta 66 through a penetration in a wall of the aorta. Expandable member 64 will be shaped and dimensioned to allow complete occlusion of ascending aorta 66 without blocking blood flow into the brachiocephalic artery 78 or the coronary ostia. Additionally, expandable member 64 will be as short as possible in the axial direction (along the central axis of the aortic lumen) to minimize its space requirements in the ascending aorta, preferably having a short cylindrical, discoid, ellipsoid, donut or toroidal shape with an axial length of about 1–40 mm, preferably about 1–20 mm. Expandable member 64 is attached to a distal end 68 of a shaft 70, which may be a rigid or flexible biocompatible metal or polymer. Shaft 70 extends through the penetration in the aortic wall and out of the chest through an access port 72 between the ribs R. Shaft 72 is at least about 6 cm, preferably about 10–20 cm, in length so that its proximal end 76 is outside of the chest when expandable member 64 is in the ascending aorta 66 between the brachiocephalic artery 78 and the coronary ostia (not shown).

Access port 72, as with other access ports referred to in this application, is illustrated as a tubular cannula or trocar sleeve, but may alternatively comprise a wound retractor with rigid blades or flexible adhesive strips for retracting tissue to create a small opening between the ribs. Instruments may alternatively be positioned directly through a puncture or incision between the ribs without a retractor, cannula or trocar, but usually some means of retracting tissue is desirable to prevent tissue damage and to facilitate introduction and manipulation of instruments. In some cases, it may be necessary to cut or remove one or more of the costal cartilages that connect the ribs to the sternum, to allow a slightly greater degree of rib retraction. However, in most cases, the access ports will be configured to facilitate introduction of surgical instruments, visualization devices, valve prostheses, and other devices used in the various procedures of the invention without removing the ribs R or sternum S, and preferably without retracting or cutting the ribs R significantly. Thus, the access ports will have a transverse profile suitable for positioning within an intercostal space I between two adjacent ribs R, which typically has a width (the distance between adjacent ribs R) of about 10–25 mm in normal adult patients, without cutting or removing the ribs, and without retracting the ribs more than about 1–2 cm from their natural, undeflected positions. In many cases, the access ports may be circular in cross-section with an outer diameter of less than about 12 mm so as to be easily positionable within an intercostal space I. In other cases the access ports may have a cross-sectional shape other than circular and may have a slightly larger transverse dimension to accommodate specialized instruments or prostheses, as described below.

As shown in FIG. 4, shaft 70 includes a delivery lumen 80 extending from a first connector 82 at proximal end 76 to a delivery port 84 at distal end 68, through which cardioplegic fluid may be delivered into ascending aorta 66. If expandable member 64 is a balloon, shaft 70 also has an inflation lumen 86 extending from a second connector 88 to the interior of expandable member 64, through which an inflation fluid such as saline or contrast solution may be delivered into the balloon. In addition, shaft 70 may optionally include an arterial return lumen 90 extending from a third connector 92 at proximal end 76 to an arterial return port 94 at distal end 68, through which oxygenated blood may be delivered into the aorta downstream of expandable member 64. Third connector 92 may be connected with tubing to the outlet of cardiopulmonary bypass system 20, allowing arterial return lumen 90 to be used in place of or as a supplement to the use of separate arterial return cannula 26 of FIG. 1. Shaft 70 may also include a pressure lumen (not shown) extending from proximal end 76 to a pressure port (not shown) at distal end 68 to allow pressure monitoring in ascending aorta 66 upstream of expandable member 64.

Shaft 70 is dimensioned so as to pass easily through access port 72 between ribs R, while having sufficient cross-section that lumens 80, 86 and 90 are large enough to perform their respective functions. Usually shaft 70 will have an outer diameter of less than about 12 mm, preferably less than about 10 mm. Delivery lumen 80 must be large enough in cross-section to allow cardioplegic fluid to be delivered at a sufficient flow rate to induce and maintain cardioplegic arrest, preferably allowing cooled cardioplegic fluid containing blood, usually having a viscosity of about 1–4 centipoise, to be delivered at a flow rate of at least about 200 ml/min at a pressure no more than about 300 mmHg. Thus, delivery lumen 80 has a cross-sectional area of about 0.5–8 mm$^2$, preferably about 0.5–2.0 mm$^2$. Arterial return lumen 90 is preferably large enough to allow blood to be delivered at flow rates adequate to maintain full cardiopulmonary bypass with the heart arrested (preferably without the use a separate arterial return cannula), having a cross-sectional area of about 12–75 mm$^2$, and preferably about 25–50 mm$^2$. In addition, inflation lumen 86 must be large enough to allow saline or other inflation fluid to be delivered at flow rates sufficient to inflate expandable member 64 in less than about 30 seconds, preferably less than about 10 seconds, having a cross-sectional area of about 0.1–5 mm$^2$, preferably about 1–3 mm$^2$.

Figure 5:
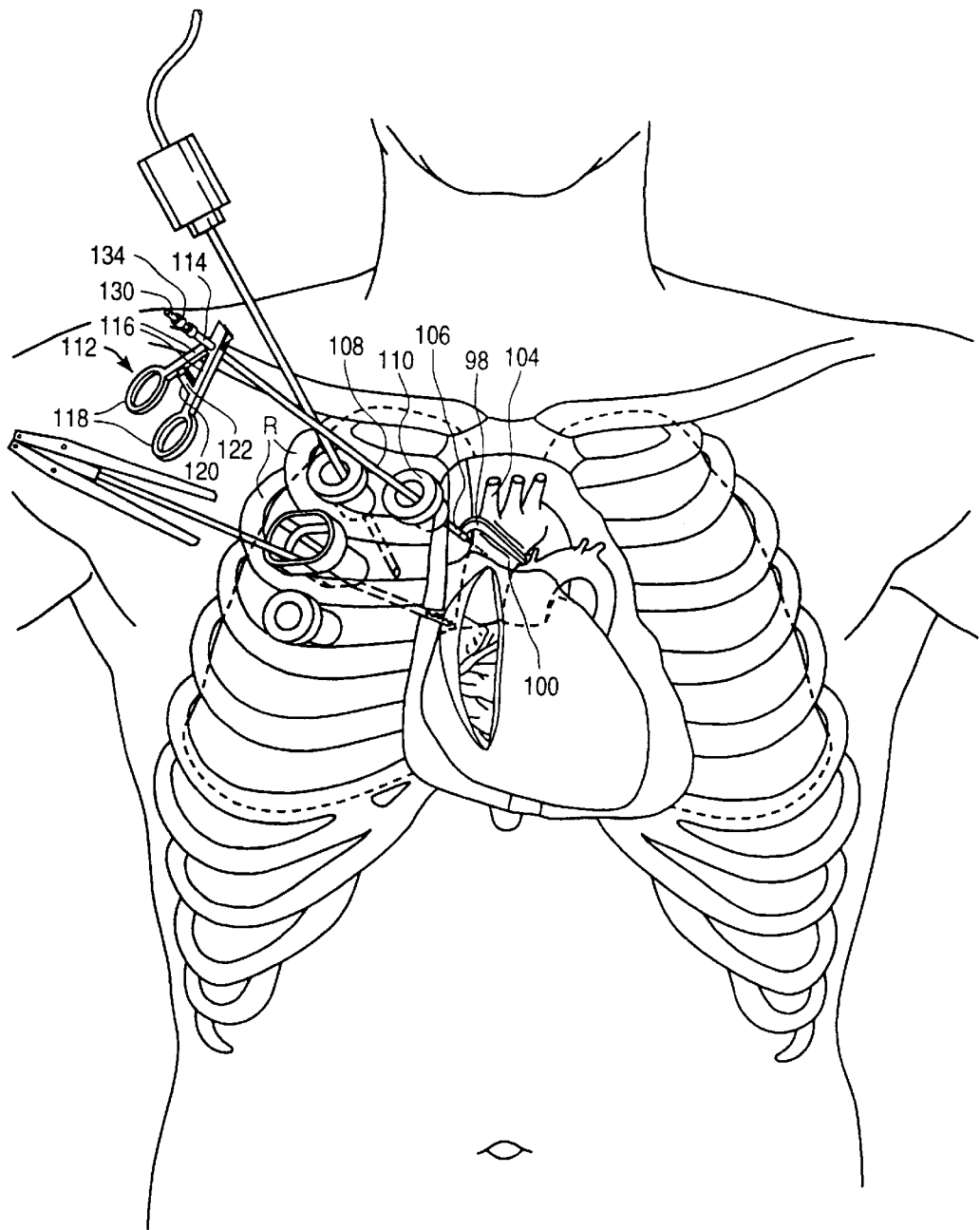
FIG. 5 is an anterior view of a patient's chest schematically illustrating a second embodiment of a thoracoscopic system for inducing cardioplegic arrest and establishing cardiopulmonary bypass according to the invention.
Figure 6:
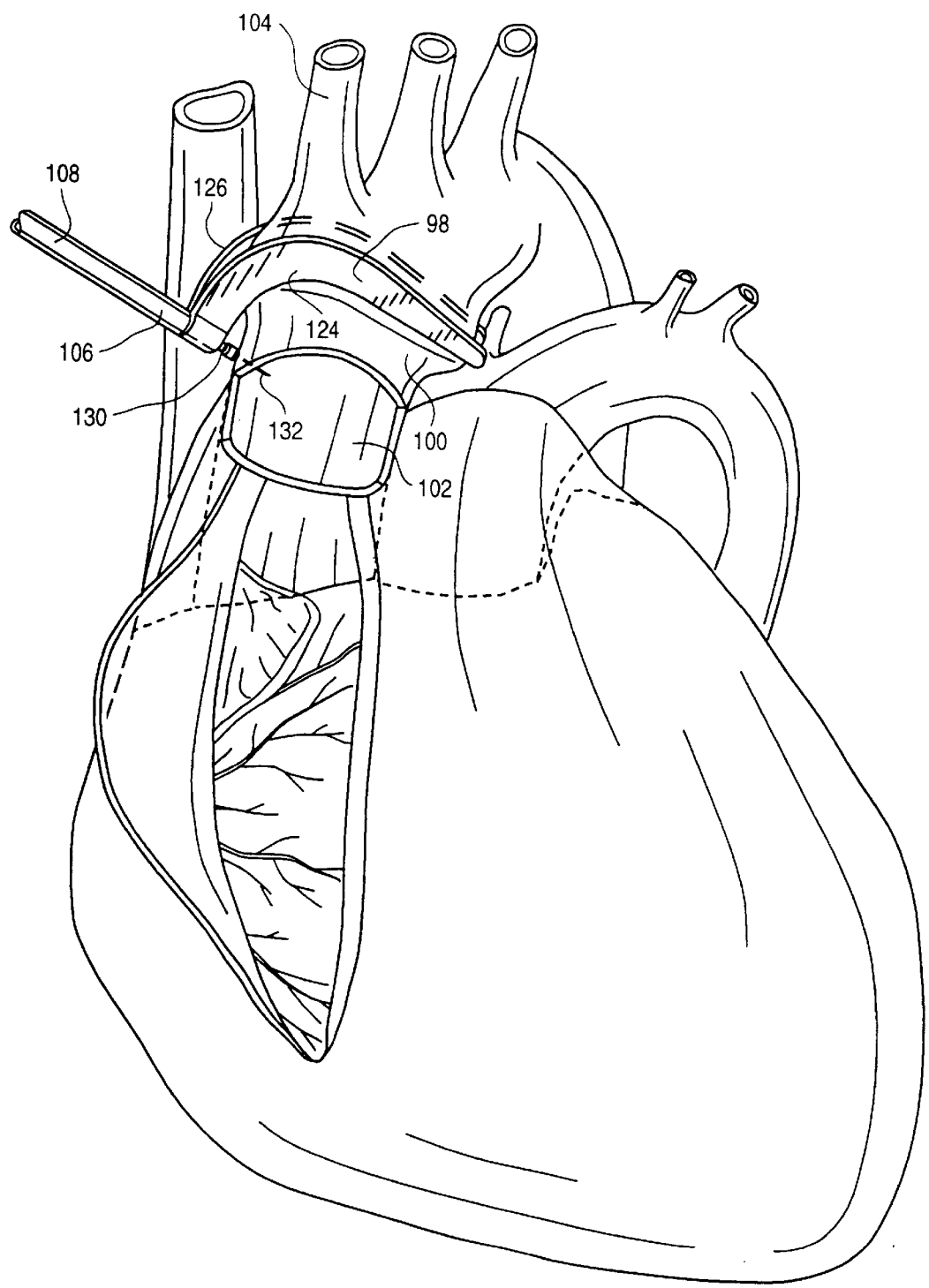
FIG. 6 is a close-up view of a patient's heart and aorta illustrating the placement of a thoracoscopic clamp in the system of FIG. 5.

A second embodiment of a thoracoscopic technique for inducing cardioplegic arrest is illustrated in FIGS. 5–6. In this technique, an external clamp 98 is placed around the ascending aorta 100 to occlude the aortic lumen 102 just upstream of the brachiocephalic artery 104. Clamp 98 is attached to a distal end 106 of a shaft 108 which is long enough to extend out of the chest through an access port 110 between ribs R, having a length of at least about 10 cm, preferably 20–30 cm. An actuator 112 is attached to proximal end 114 of shaft 108 to allow clamp 98 to be opened and closed from outside of the chest. Actuator 112 includes a pair of movable handles 116 with finger loops 118, and a locking mechanism 120 which may comprise a pair of overlapping fingers 122 with transverse teeth (not shown) which interlock with one another. Clamp 98 includes a first jaw 124 fixed to shaft 108, and a second jaw 126 fixed to an inner shaft (not shown) extending through the interior of shaft 108 and rotatable relative to shaft 108. One of handles 116 is fixed to the proximal end of shaft 108, while a second of handles 116 is fixed to a proximal end of the inner shaft, so that by pivoting handles 116 relative to one another, the inner shaft rotates relative to shaft 108, opening or closing jaws 124, 126. Other aspects of thoracoscopic clamping devices suitable for use in the method of the invention are described in U.S. Pat. No. 5,425,705, which is incorporated herein by reference.

In order to deliver cardioplegic fluid into the ascending aorta, several alternative techniques may be used. In one technique, illustrated in FIGS. 5–6, a delivery cannula 130 may be positioned through an inner lumen of shaft 108 so that a needle 132 at the distal end of the delivery cannula extends distally of distal end 106 of shaft 108, generally parallel to and spaced apart from jaws 124. Jaws 124 may be curved or angled away from shaft 108 so that the portions of the jaws that extend around the aorta are offset from needle 132 to allow needle 132 to be placed through shaft 108 and penetrate the aortic wall upstream from jaws 124. Delivery cannula 130 has an inner lumen extending from its distal end to its proximal end which may be connected to a cardioplegic fluid source. In one embodiment, a connector 134 is provided near the proximal end of delivery cannula 130 which connects to a connector on the proximal end of shaft 108 to fix the delivery cannula in position relative to clamp 98. In this way, after clamp 98 has been closed on ascending aorta 100 to occlude the aortic lumen 102, delivery cannula 130 may be positioned through shaft 108 to penetrate the aortic wall with needle 132, allowing cardioplegic fluid to be delivered upstream of clamp 98. The inner lumen of delivery cannula 130 will be configured to facilitate delivering cardioplegic fluid containing blood at a rate of at least about 200 ml/min and a pressure of no more than about 300 mmHg, having a cross-sectional area of at least about 0.5 mm$^2$, and preferably 0.5–2.0 mm$^2$. Delivery cannula 130 may alternatively be independent of clamp 98 and shaft 108, and placed through a separate access port rather than being placed through shaft 108.

Alternative techniques of delivering cardioplegic fluid are described in U.S. Pat. No. 5,425,705, which has been incorporated herein by reference. In one such technique, not illustrated here, an endovascular delivery catheter may be placed through a peripheral artery such as a femoral artery until its distal end is in the ascending aortic lumen 102 upstream of the brachiocephalic artery 104. Clamp 98 may then be actuated to close on the aorta around the endovascular delivery catheter, which may be reinforced in its distal extremity to prevent collapsing. In this way, cardioplegic fluid may be delivered upstream of the external clamp 98 without requiring a puncture through the aortic wall. Such an endovascular delivery catheter may also include a pressure port and pressure lumen for monitoring pressure in the ascending aorta during the procedure.

Figure 7:
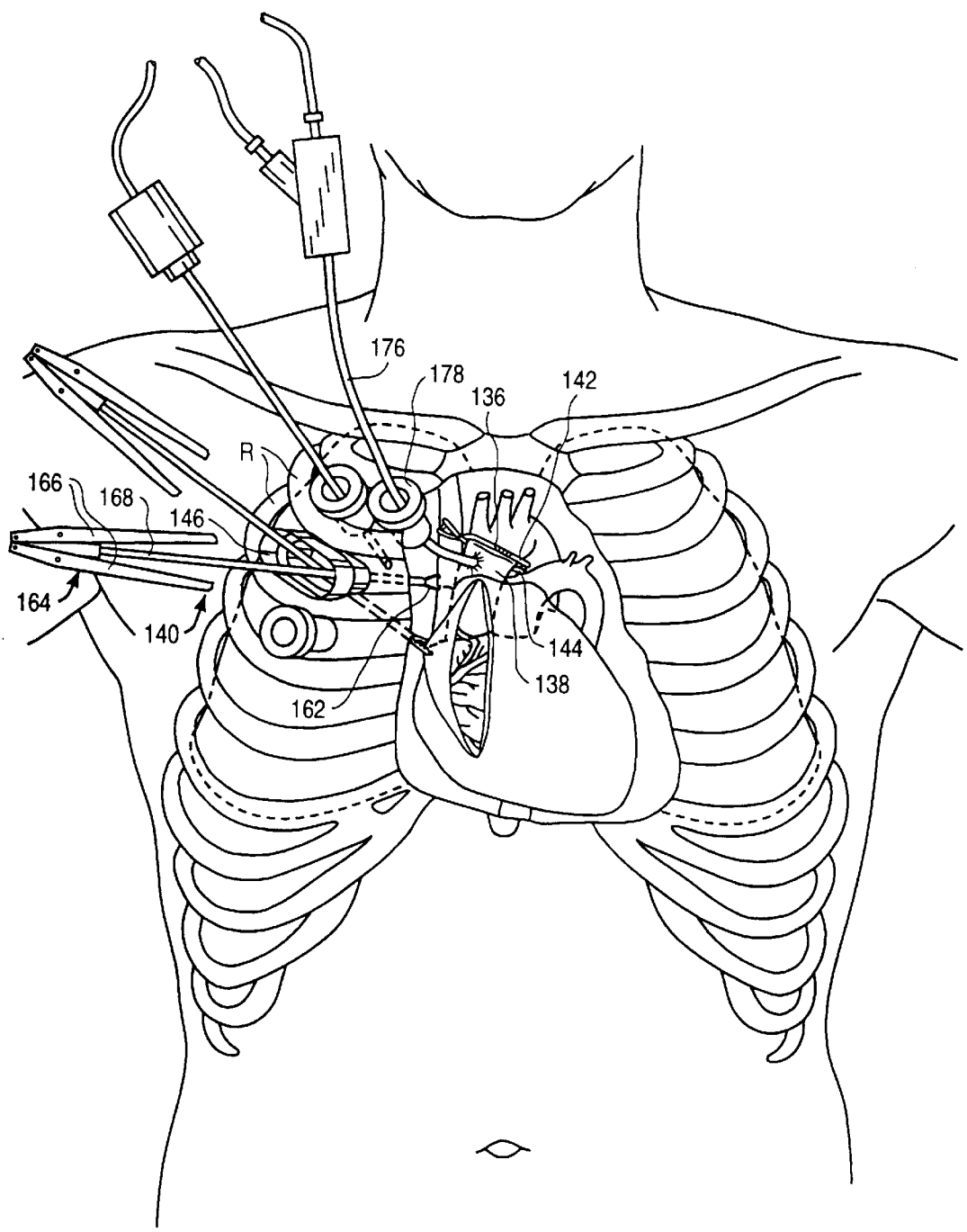
FIG. 7 is an anterior view of a patient's chest schematically illustrating a third embodiment of a thoracoscopic system for inducing cardioplegic arrest and establishing cardiopulmonary bypass according to the invention.
Figure 8:
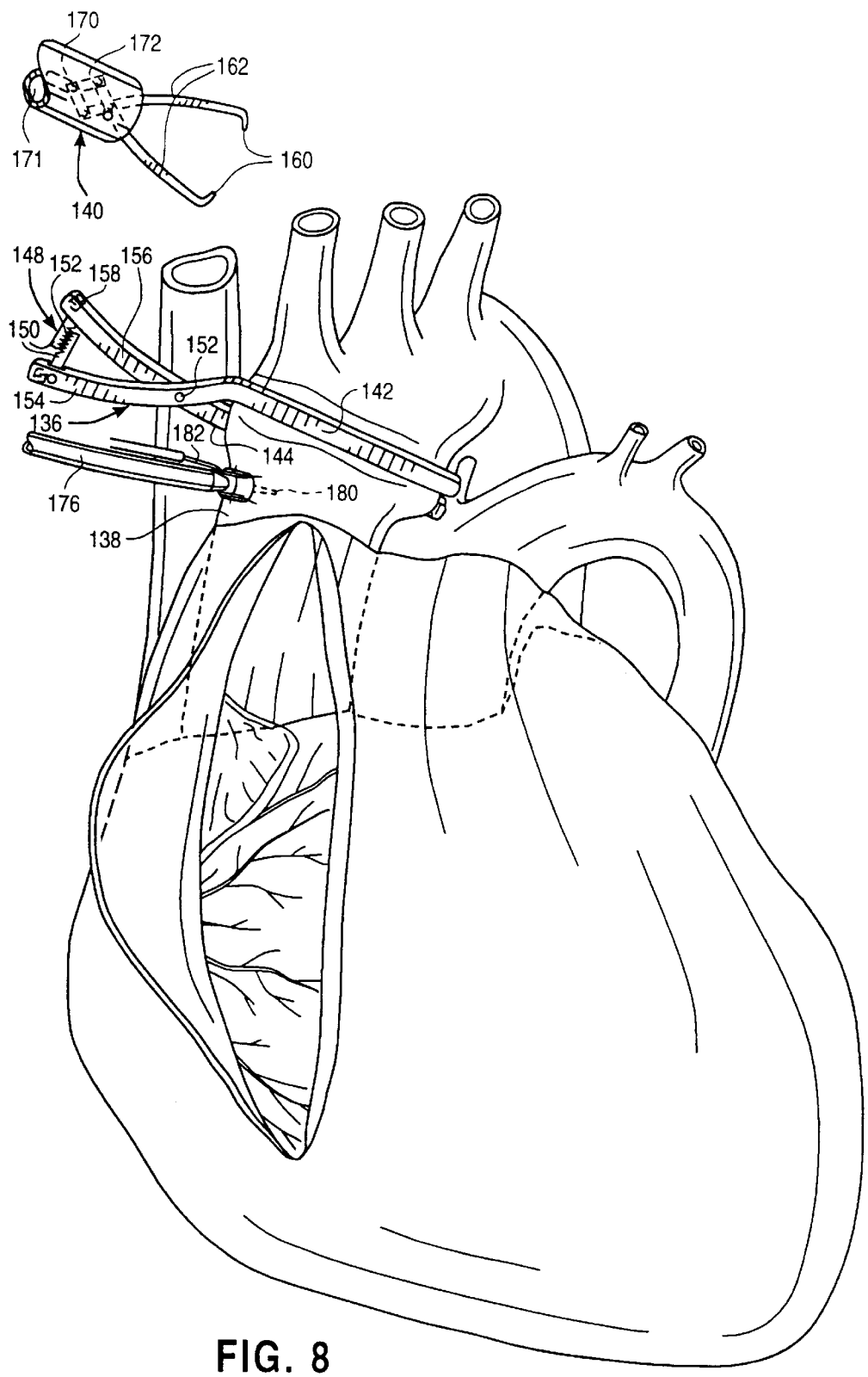
FIG. 8 is a close-up view of a patient's heart and aorta illustrating the placement of a detachable thoracoscopic clamp and applicator in the system of FIG. 7.

In a further embodiment of a thoracoscopic aortic occlusion technique, illustrated in FIGS. 7–8, an external clamp 136 is placed around the ascending aorta 138 by a thoracoscopic clamp applier 140, closed on aorta 138 to block blood flow through the aortic lumen, then released from clamp applier 140, which may then be removed from the chest. Clamp 136 comprises a pair of movable jaws 142, 144 pivotably connected to each other by a pin 152. Jaws 142, 144 have proximal extremities 154, 156 proximal to pin 152 to which a locking mechanism 148 is mounted, which may comprise a pair of deflectable overlapping fingers 150 having transverse teeth 152 which interlock with one another to maintain clamp 136 in a closed position. A pair of detents 158 are disposed at the proximal ends of jaws 142, 144 and are adapted to receive the distal tips 160 of clamp applier jaws 162. Clamp 136 is configured to be positionable through an access port 146 or incision between ribs R. Access port 146 has a transverse cross-sectional width to fit between the ribs without requiring significant deflection or removal of the ribs, but may have a longer transverse cross-sectional dimension parallel to the ribs to allow clamp 136 to be positioned through the access port when held by clamp applier 140.

Clamp applier 140 has, as shown in FIG. 7, an actuator 164 at its proximal end which comprises one or more movable leaves 166 pivotably mounted to a shaft 168. Leaves 166 are linked to clamp applier jaws 162 by a linkage 170, best seen in FIG. 8, which may be a rod or wire slidably disposed in a lumen 171 within shaft 168, linked to a scissors mechanism 172 coupled to jaws 162. In this way, moving leaves 166 toward shaft 168 causes jaws 162 to move between an open position for releasing clamp 136 to a closed position for grasping and closing clamp 136. Clamp 136 is preferably biased into an open configuration by a torsion spring (not shown) around pin 152 or a compression spring (not shown) between proximal extremities 154, 156 of jaws 142, 144. In this way, once locking mechanism 148 is released by deflecting fingers 150 away from each other, clamp 136 will be urged open as clamp applier jaws 162 are opened. Other aspects and alternative configurations of clamp 136 and clamp applier 140 are disclosed in commonly-assigned copending application Ser. No. 08/567,996, filed Dec. 4, 1995, now U.S. Pat. No. 5,618,307, which is hereby incorporated herein by reference.

With clamp 136 closed on the aorta to occlude blood flow through the aortic lumen, cardioplegic fluid may be delivered into the ascending aorta by means of a delivery cannula 176 placed into the chest through an access port 178 and having a needle 180 at its distal end for penetrating the aortic wall. Usually, a purse-string suture 182 will be placed in the aortic wall surrounding needle 180 using thoracoscopic needle drivers positioned through an intercostal access port. The purse-string suture 182 is cinched up around delivery cannula 176 to maintain hemostasis around the cannula. Alternatively, as discussed above, an endovascular delivery catheter (not illustrated) may be used which extends into the ascending aortic lumen transluminally from a peripheral artery such as the femoral, brachial, or subclavian artery. Clamp 136 is clamped around the aorta after the endovascular delivery catheter has been positioned so that the inner wall of the aorta seals against the outer wall of the delivery catheter. The delivery catheter may be reinforced in its distal extremity to resist collapsing under the force of clamp 136. The delivery catheter may alternatively have an expandable member such as a balloon near its distal end which may be expended in the ascending aorta like endoaortic catheter 32 of FIGS. 1–2. Clamp 136 may then be applied to the ascending aorta directly around the expandable member to achieve complete occlusion without excessive crushing or collapsing of the aorta. Clamp 136 may also be placed distally or proximally of the expandable member, or a clamp may be placed in either side, to prevent migration of the expandable member as well as blocking blood flow.

In addition, retrograde delivery of cardioplegic fluid via the coronary sinus by means of an endovascular catheter introduced through a peripheral vein (described above) may be used instead of or in combination with antegrade delivery through a thoracoscopic or endovascular delivery catheter placed in the aorta.

It should be noted that, in some cases, it may be appropriate not to induce cardioplegic arrest, but instead to place the heart in a state of fibrillation. While this is usually not desirable because it is generally thought to provide inadequate protection of the myocardium, it may be induced using the devices and methods of the present invention. The patient is placed on cardiopulmonary bypass as described above (without occluding the ascending aorta so as to arrest the heart), and the oxygenated blood returned to the arterial system is cooled to a sufficiently low temperature to induce fibrillation. An endovascular or thoracoscopic catheter may be placed in the ascending aorta as described above, and, without occluding the ascending aorta, drugs or blood may be delivered to the coronary arteries, and fluids may be removed to vent the heart and aorta. Alternatively, one of the above-described aortic occlusion devices may be used to periodically induce fibrillation during the procedure by occluding the aorta temporarily without delivering the cardioplegic fluids that induce cardioplegic arrest, with intermittent periods of no occlusion so as to avoid ischemia.

While the remainder of the aortic valve replacement procedure is described with reference to the use of clamp 136 and delivery cannula 176 for inducing cardioplegic arrest, it should be understood that any of the devices and techniques described above, as well as various other techniques not specifically described here, may be used for inducing cardioplegic arrest without departing from the scope of the invention.

Figure 9:
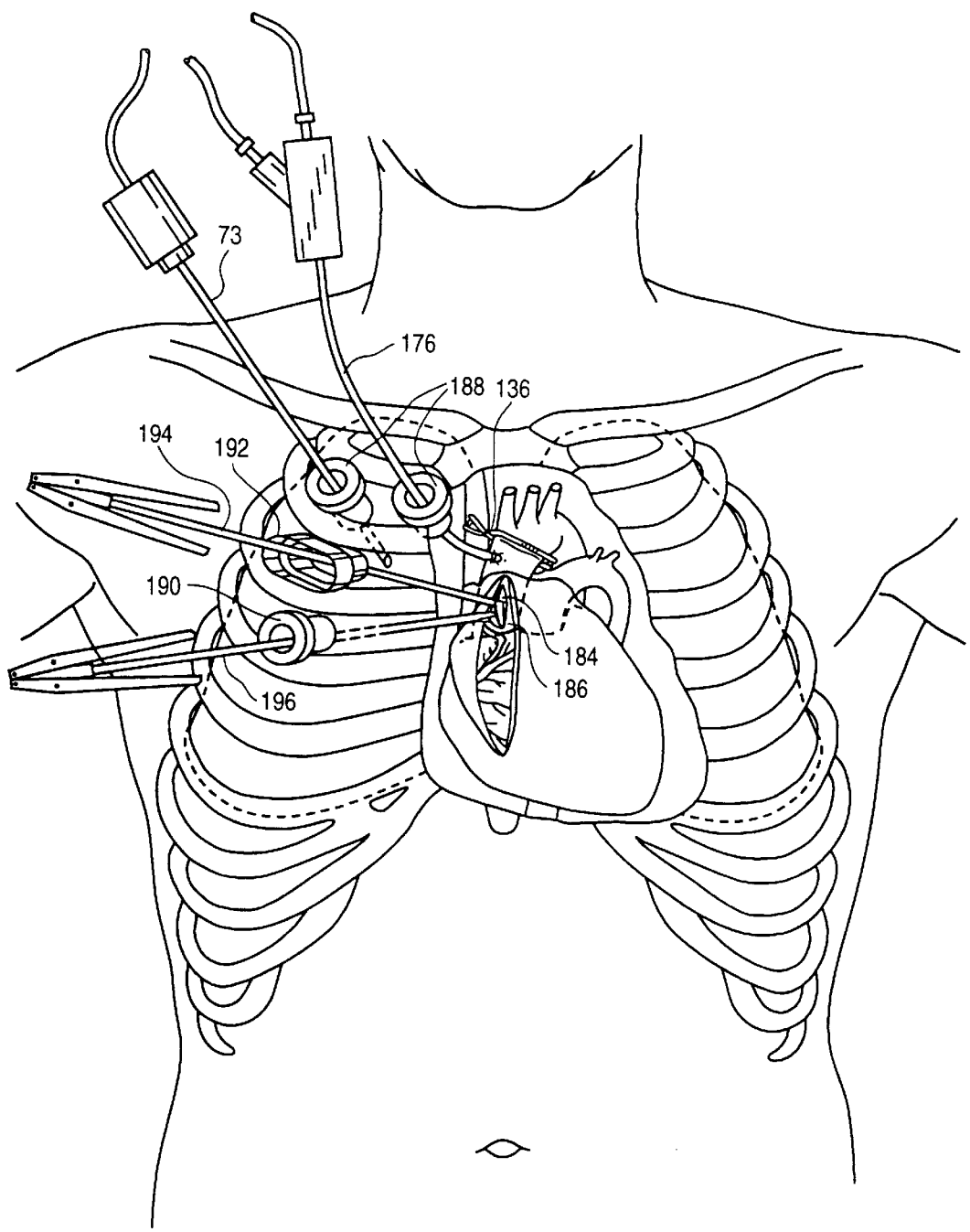
FIG. 9 is an anterior view of a patient's chest schematically illustrating the formation of an aortotomy in the ascending aorta according to the invention.
Figure 10:
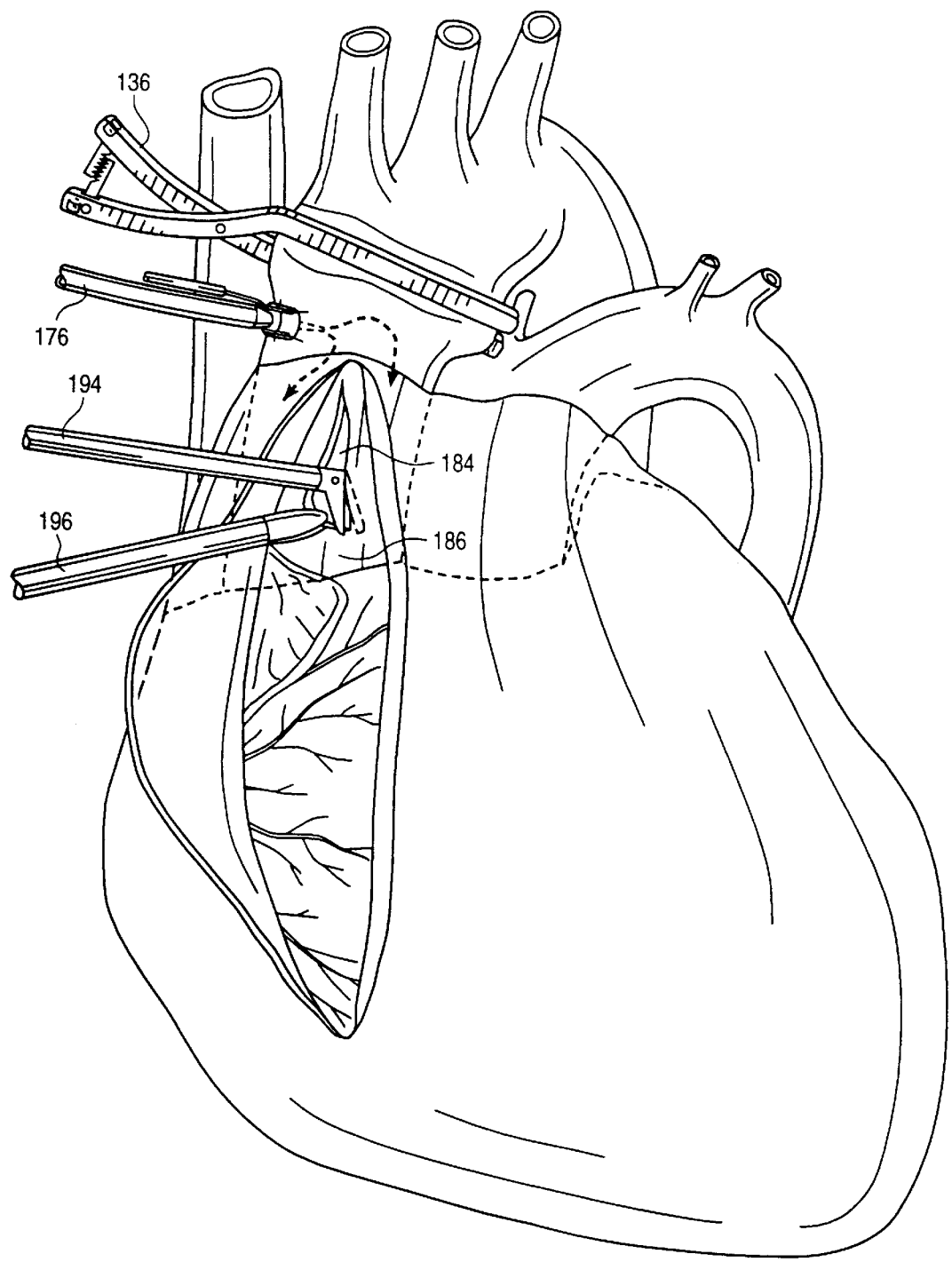
FIG. 10 is a close-up view of a patient's heart and aorta illustrating the formation of an aortotomy in the ascending aorta according to the invention.

Once cardioplegic arrest is induced, the patient is supported on cardiopulmonary bypass, and the pericardium has been opened as described above, an incision, or aortotomy, 184 is formed in the wall of ascending aorta 186 as shown in FIGS. 9–10. At this point, at least one, and usually at least three, access ports should be placed in intercostal spaces I between ribs R on the right anterior side of the chest. One or two access ports 188 with outer diameter less than about 12 mm are placed in the first, second, or third intercostal space through which delivery cannula 176 and thoracoscope 73 (if utilized) are positioned. Another access port 190 with outer diameter less than about 12 mm is placed in the third, fourth or fifth intercostal space through which various instruments used in the procedure may be positioned. An additional access port 192, which is specially-configured for positioning a replacement valve through its central lumen as described more fully below, is placed in the first, second, third or fourth intercostal space, depending upon patient size and anatomy. As described above, access ports 188, 190, 192 may comprise trocar sleeves or other tubular cannulae, or simply incisions in which tissue is retracted apart to create a small opening using any of a variety of tissue retraction devices. Preferably, however, access ports 188, 190, 192 will not require cutting or removal of ribs or the sternum, and will not require significant retraction of the ribs, preferably requiring less than about 2 cm of retraction from the ribs' natural, undeflected positions.

It should be noted that, in the absence of a large thoracic incision for access into the chest, some means of illuminating the chest cavity is usually necessary. A thoracoscopic light wand or a commercially-available thoracoscope or endoscope having a fiber-optic channel which emits light from the distal end of the device may be placed through an access port for illumination. Alternatively, one or more access ports may have an illumination device mounted to it, as described below in connection with FIGS. 37–40.

Aortotomy 184 is created using thoracoscopic angled scissors 194 or a knife (not shown) positioned through access port 192, assisted by means of thoracoscopic forceps 196 positioned through access port 190. Angled scissors 194 and forceps 196 may be commercially-available thoracoscopic instruments or may be constructed as described in copending applications Ser. No. 08/194,946, now U.S. Pat. No. 5,501,698, and Ser. No. 08/281,962, now abandoned, which have been incorporated herein by reference. Aortotomy 184 is approximately 6–8 cm in length, extending distally and slightly posteriorly along the anterior side of the aorta from a point at least about 10 mm, and preferably about 15 mm, downstream of the right coronary ostium.

Figure 11:
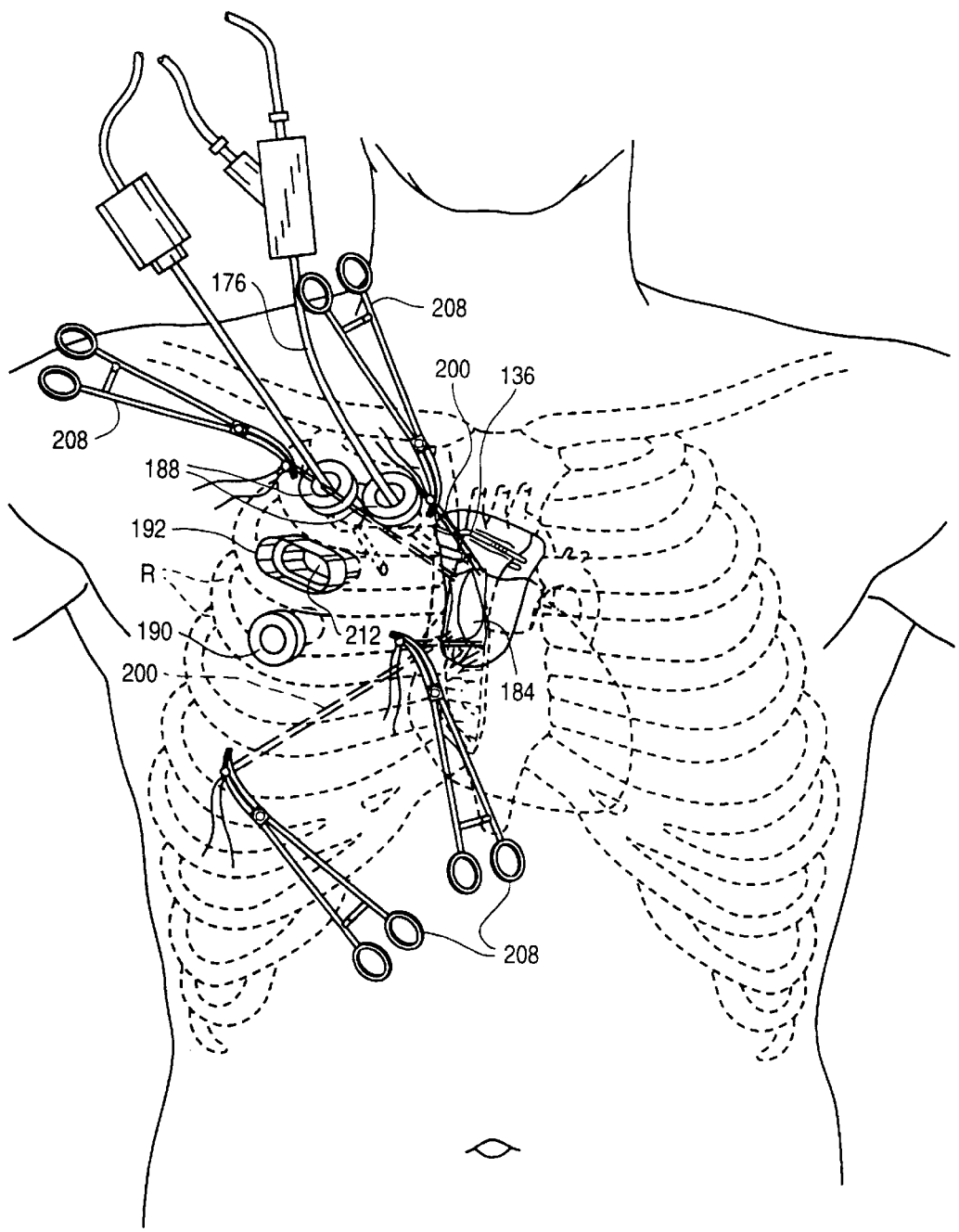
FIG. 11 is an anterior view of a patient's chest schematically illustrating retraction of the aortotomy according to the invention.
Figure 12:
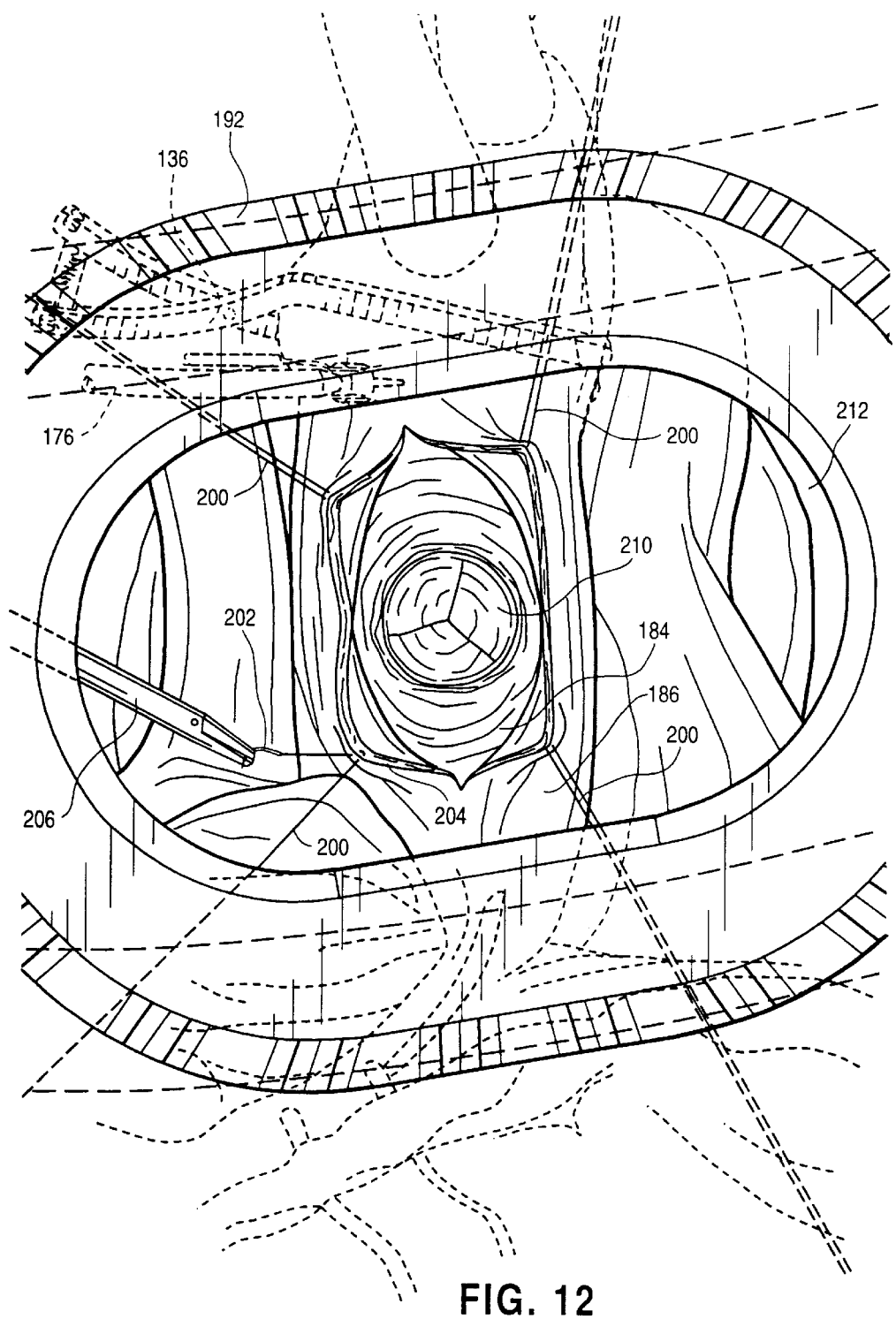
FIG. 12 is a view of the aortotomy and the aortic valve through an oval-shaped access port placed in an intercostal space in the patient's chest, illustrating the placement of sutures for retraction of the aortotomy according to the invention.
Figure 13:
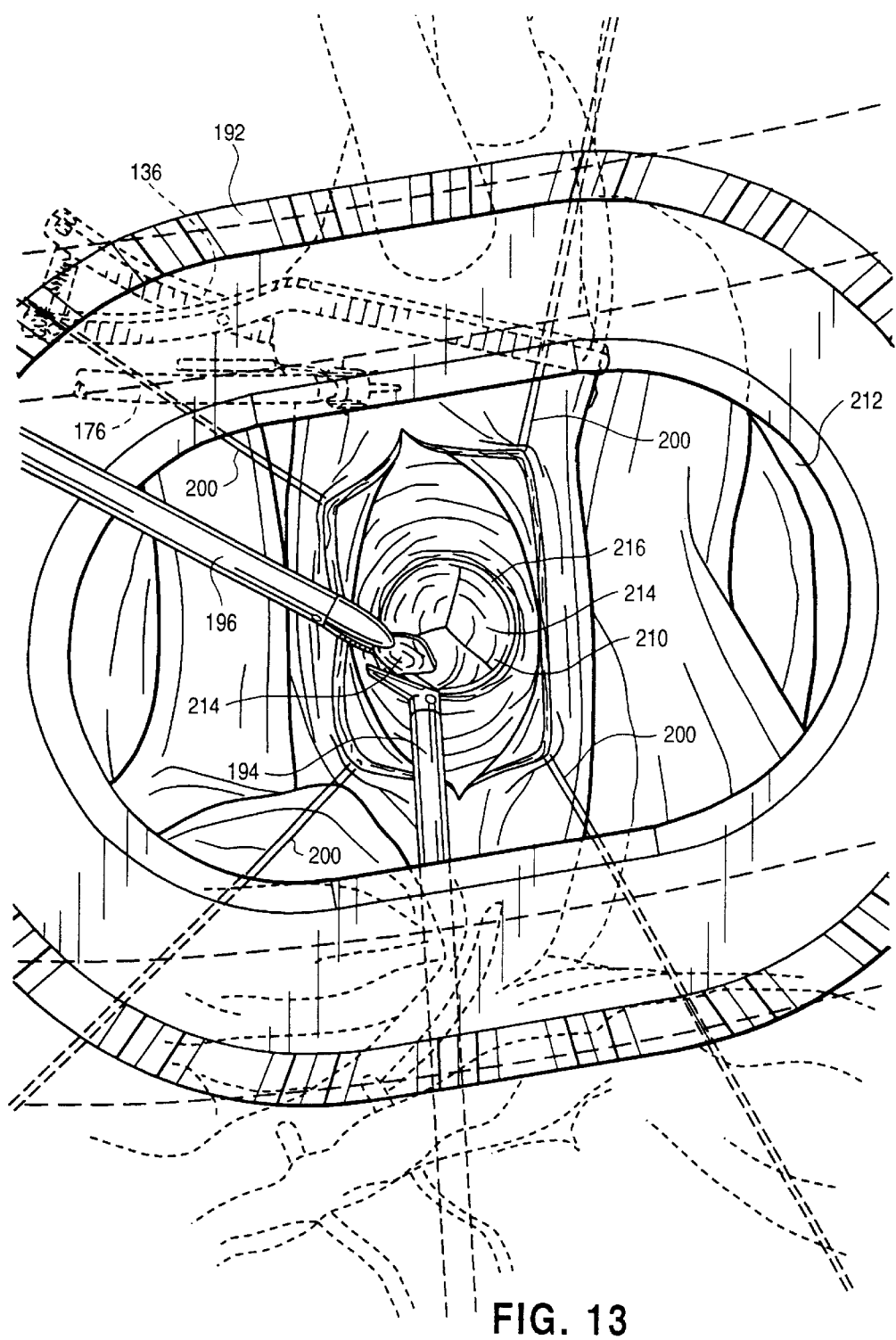
FIG. 13 is a view of the aortotomy and the aortic valve through an oval-shaped access port placed in an intercostal space in the patient's chest, illustrating the removal of the aortic valve leaflets according to the invention.

Aortotomy 184 is then retracted open as illustrated in FIGS. 11–12. In an exemplary embodiment, sutures 200 are placed in the aortic wall along the edges of aortotomy 184, preferably with a suture near each end of aortotomy 184 on each side of the incision. Each of sutures 200 has a needle 202 attached to an end thereof which is driven through aortic wall 204 using thoracoscopic needle drivers 206 introduced through either access port 190 or access port 192. Needle drivers 206 may be commercially-available thoracoscopic instruments or may be constructed as described in the aforementioned patent applications, Ser. Nos. 08/194,946, or 08/281,962, now abandoned. Sutures 200 preferably have a length of at least about 20 cm so that they may be withdrawn from the chest cavity by passing needles 202 through the chest wall between ribs R or by snaring the sutures with a hook introduced through an intercostal space. Sutures 200 are tensioned in opposing directions to retract aortotomy 184 open and are then secured outside the chest with hemostats 208 or other suitable clamping device of conventional construction. Alternatively, sutures 200 may be secured to tissue within the chest cavity by passing needles 202 through such tissue and tying the sutures off, or by attaching the suture ends to a clip, clamp, hook or staple which can be fastened to tissue in the chest. With aortotomy 184 retracted open, the aortic valve 210 is fully exposed and visible through the inner lumen 212 of access port 192, as illustrated in FIG. 12.

The leaflets 214 of the native aortic valve 210 are then removed using thoracoscopic curved or angled scissors 194 or knife (not illustrated), and forceps 196 positioned through access ports 190, 192, respectively. Leaflets 214 are grasped by forceps 196, retracted away from the valve annulus 216, and cut closely to the inner edge of valve annulus 216 without cutting into the valve annulus or the aortic wall.

Figure 14:
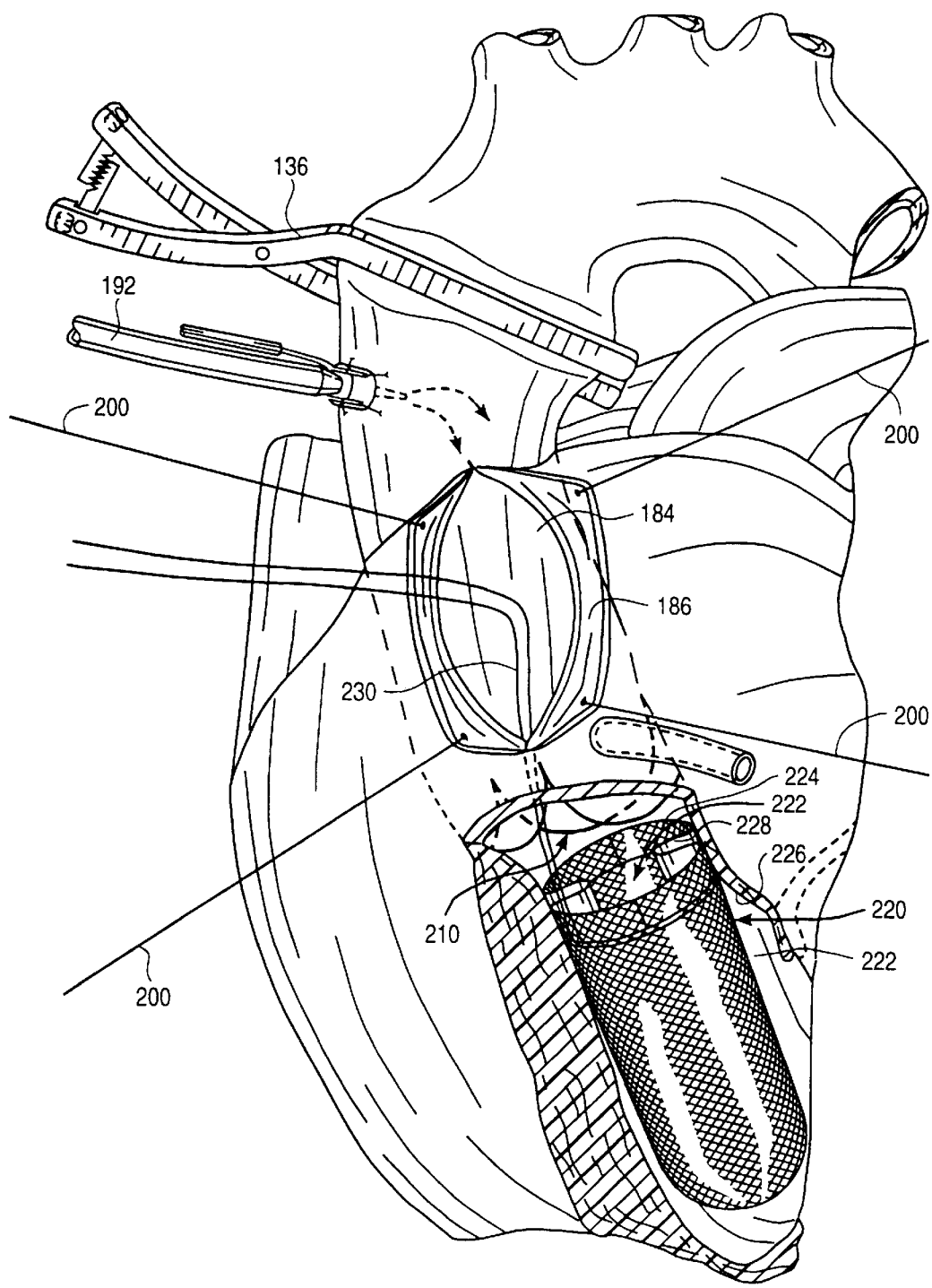
FIG. 14 is a close-up partial cross-section of the left ventricle of the heart and the aorta showing a catcher placed in the left ventricle to catch pieces of valve leaflet and debris removed from the native valve annulus according to the invention.
Figure 15:
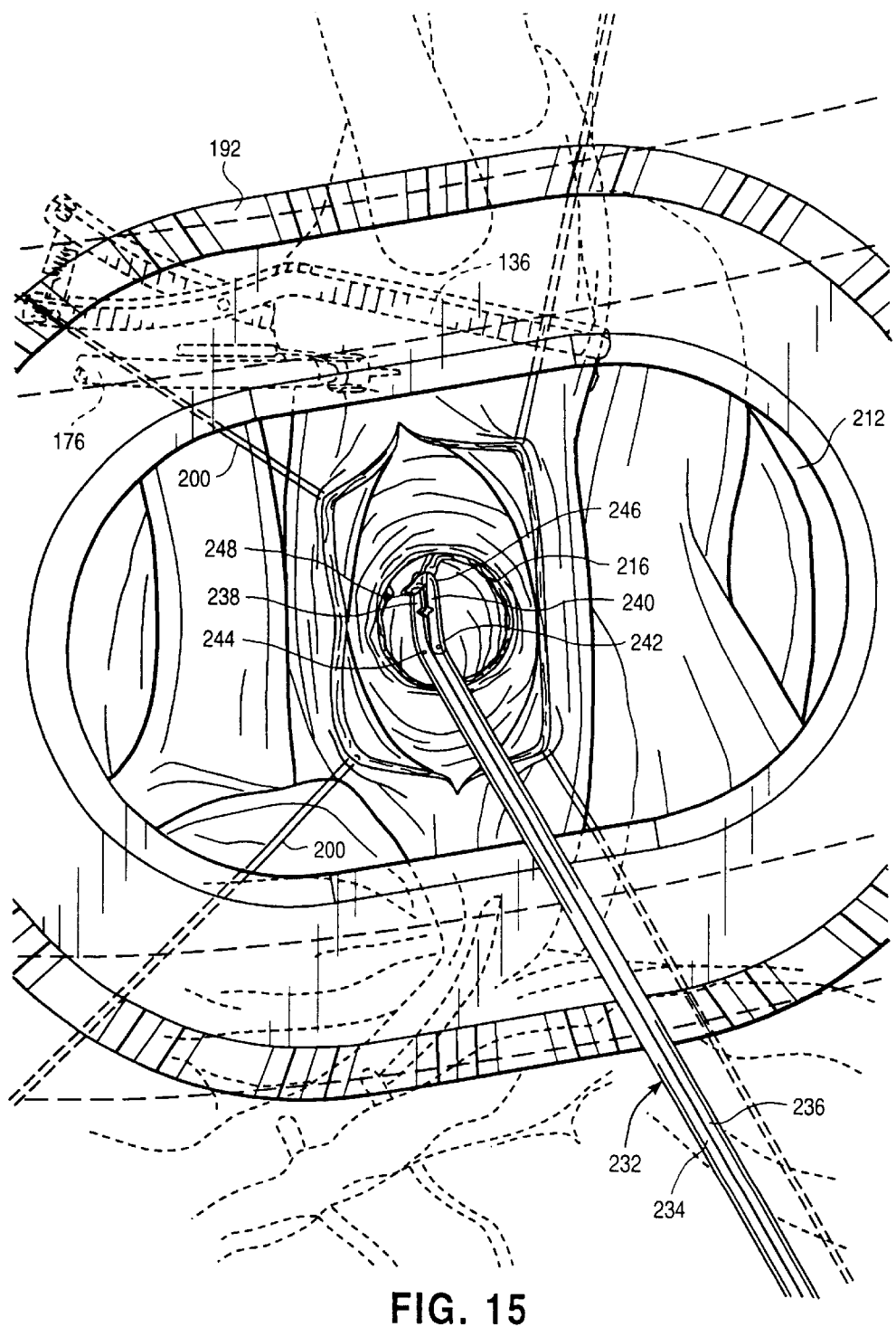
FIG. 15 is a view of the aortotomy and the aortic valve through an oval-shaped access port placed in an intercostal space in the patient's chest, illustrating the removal of calcific and fibrous material from the native valve annulus according to the invention.

During this process, it may be advantageous to provide a mechanism for catching any bits of valve leaflet, calcium or other debris that may fall into the left ventricle as the leaflets are excised. As illustrated in FIG. 14, a catcher 220 may be placed through aortic valve 210 into the left ventricle 222 and positioned so as to catch any debris released in the leaflet removal or debridement process. Catcher 220 may comprise a flexible, porous mesh, foam, gauze, or screen constructed as a bag or pouch with an opening 222 on a top end 224 thereof. Top end 224 is configured to be positioned in the left ventricle just below the aortic valve, with the sides of catcher 220 engaging the ventricular wall 226. Preferably catcher 220 is collapsible into a smaller shape suitable for positioning through access port 190 or access port 192, through aortotomy 184, and through aortic valve 210, and at least top end 224 is resiliently biased to return to an expanded configuration in which the outer sides of top end 224 engage ventricular wall 226. A flexible and resilient metal or elastomeric ring 228 may be mounted to catcher 220 around opening 222 which may be radially collapsed during positioning, then released to allow the ring to expand outwardly to engage the ventricular wall. To facilitate positioning, catcher 220 may be collapsed and placed in a tubular sleeve or catheter (not shown) during positioning through the aortic valve, then ejected from the sleeve within the left ventricle. Alternatively, thoracoscopic forceps or graspers positionable through an intercostal access port may be used to grasp and collapse catcher 220 and position it into the left ventricle. A suture or other flexible tether 230 is preferably attached to catcher 220 and extends out of the chest through an access port to allow catcher 220 to be retrieved after use. The aforementioned tubular sleeve may be guided over tether 230 back into the left ventricle and catcher 220 then collapsed and retracted into the sleeve to facilitate removing the device from the chest.

Following removal of the aortic valve leaflets, any calcific deposits and any remaining leaflet tissue around the inner surface of valve annulus 216 are removed using thoracoscopic rongeurs 232. Rongeurs 232 have a split-shaft construction, wherein two independent shaft members 234, 236 are longitudinally slidable relative to one another. A fixed jaw 238 is disposed at the end of shaft member 234, and a movable jaw 240 is pivotably mounted to the distal end of shaft member 236 by a first pin 242 and pivotably attached to shaft member 234 by a second pin 244. In this way, longitudinal translation of shaft member 236 relative to shaft member 234 by means of an actuator (not shown) at the proximal end of the device pivots movable jaw 240 relative to fixed jaw 238. Fixed jaw 238 and movable jaw 240 have hollow or concave inner sides facing each other, and cutting edges 246, 248 along the periphery of their inner sides. This construction allows cutting edges 246, 248 to be positioned close to or against the inner surface of valve annulus 216 to excise any remaining leaflet material or calcific deposits along the valve annulus. Any material removed is collected within the concave inner sides of jaws 238, 240. In a preferred embodiment, rongeurs 232 include a suction lumen through which a vacuum may be applied from the proximal end of the device to evacuate tissue and debris as it is cut from valve annulus 216. In the split shaft design of FIG. 15, for example, at least one of shaft members 234, 236 may be provided with an inner lumen in communication with the inner sides of jaws 238, 240 through which a vacuum may be applied to evacuate material cut by cutting edges 246, 248.

In addition, an irrigation lumen may be provided in one of shaft members 234, 236 to allow an irrigation fluid such as saline to be delivered to the inner surfaces of jaws 238, 240 to keep the jaws clean and free of debris. In one embodiment, a suction lumen is provided in one shaft member 234 and an irrigation lumen is provided in the other shaft member 236 to provide both irrigation and suction in the space between jaws 238, 240.

As an alternative to the use of thoracoscopic rongeurs 232, various other devices may be used for removal of calcific and fibrous material at the native valve position, including high-speed rotating cutters or grinders like those used in atherectomy and arthroscopy devices, lasers, and ultrasonic scalpels, any of which may be equipped with irrigation or suction lumens.

Figure 16:
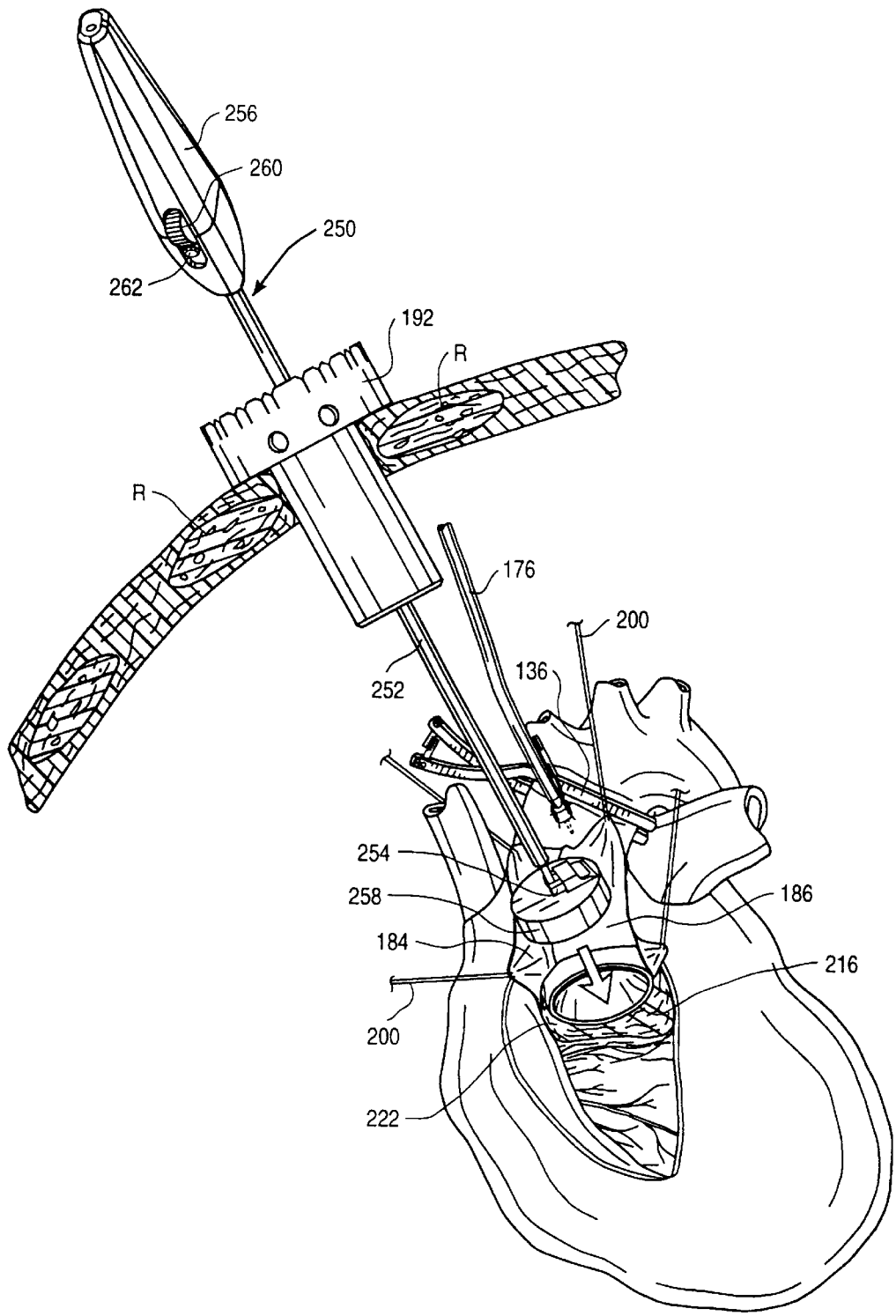
FIG. 16 is a transverse cross-sectional view of a portion of the patient's chest and heart illustrating the use of a valve sizing device for sizing the native valve annulus according to the invention.

The valve annulus is then sized to determine the appropriate size for a replacement valve. As illustrated in FIG. 16, a valve sizing device 250 is introduced through access port 192 into the ascending aorta 186 through aortotomy 184. Sizing device 250 includes a shaft 252 having a pivoting tongue 254 at its distal end and a handle 256 at its proximal end. A sizing disk 258 is releasably attached to tongue 254. An actuator button 260 is slidably mounted to handle 256 and is connected to tongue 254 by a linkage (not shown) such as a slidable rod extending through a passage in shaft 252. In this way, sliding actuator button 260 along handle 256 pivots tongue 254 from a first orientation in which the tongue is generally parallel to shaft 252 to a second orientation in which the tongue is perpendicular to shaft 252. Thus, for a generally cylindrical sizing disk having a central axis, sizing disk 258 is positionable in an orientation in which the central axis is perpendicular to the longitudinal axis of shaft 252, providing a minimum profile to allow the sizing disk to be introduced through lumen 212 of access port 192. Once inside the chest, sizing disk 258 may be re-oriented using actuator button 260 so that the sizing disk is in an appropriate orientation for sizing valve annulus 216, usually with its axis about parallel to the longitudinal axis of shaft 252 as shown in FIG. 16. A button lock 262 may also be provided on actuator button 260 to allow sizing disk 258 to be releasably locked in a suitable orientation for sizing valve annulus 216. Other aspects of valve sizing devices suitable for use in the method of the invention are described in copending applications Ser. No. 08/485,600 and Ser. No. 08/281,962, which have been incorporated herein by reference.

Once positioned inside ascending aorta 186 through aortotomy 184 and oriented in an orientation suitable for sizing valve annulus 216, sizing disk 258 is positioned within valve annulus 216 to allow a comparison of the outer diameter of sizing disk 258 to the inner diameter of valve annulus 216. To see the sizing procedure, the surgeon may look directly at valve annulus 216 through lumen 212 of access port 192 or a thoracoscope may be used for video imaging of the valve annulus. If the sizing disk is either larger or smaller than the valve annulus, sizing device 250 is removed from the chest and sizing disk 258 is removed from tongue 254 and replaced with another sizing disk of a different diameter. The process is repeated until the surgeon has identified the appropriate size of replacement valve to be implanted. It should be understood that other techniques may be used for determining the annulus size, including endoscopic video imaging, transesophageal echocardiography, or thoracoscopic ultrasonic imaging, as well as using an adjustable valve sizer that may be placed within the valve annulus and adjusted in diameter until the appropriate size is determined.

When the size of the valve annulus has been determined, the appropriate replacement valve is then identified. A variety of replacement valves may be used in the method of the invention, including many of the more widely-accepted valves used in conventional open-chest aortic valve replacement procedures. These include mechanical valves such as the St. Jude Medical Mechanical Heart Valve (St. Jude Medical, Inc., St. Paul, Minn.), the Carbomedics Prosthetic Heart Valve (Carbomedics, Inc., Austin, Tex.), and the Sorin Monostrut Heart Valve or Sorin Bicarbon Valve (Sorin Biomedical, Inc., Irvine, Calif.), as well as bioprosthetic or tissue valves, such as the Carpentier-Edwards Pericardial Bioprosthesis or Carpentier-Edwards Model 2625 Porcine Bioprosthesis (Baxter, Inc., Edwards CVS Division, Irvine, Calif.)., or Medtronic Hancock MO Bioprosthesis or Medtronic Hall valve (Medtronic, Anaheim, Calif.). In addition, the method of the invention may be used to replace a diseased aortic valve with an autologous graft such as the pulmonary valve from the same patient, which may be removed thoracoscopically from the patient's pulmonary artery using thoracoscopic instruments and visualization devices positioned through access ports between the ribs. Allografts, such as an aortic valve removed from another donor patient's heart, may also be implanted using the methods of the invention. While the aortic valve replacement procedure of the invention will be described with reference to a mechanical bileaflet valve such as the St. Jude Medical Mechanical Valve, it should be understood that the methods described are equally applicable to other types of mechanical valves, as well as to bioprosthetic valves, autografts and allografts.

Figure 17:
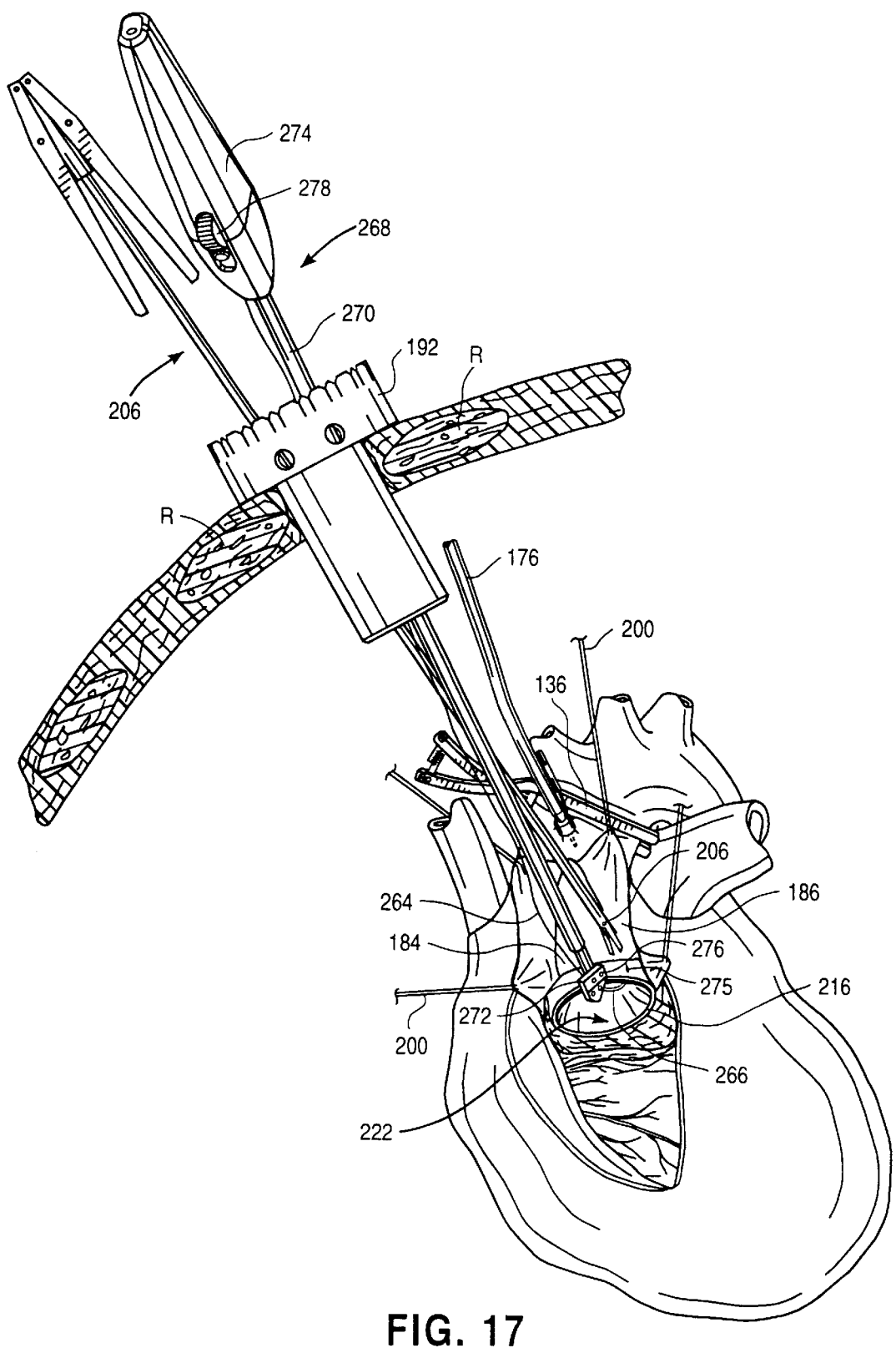
FIG. 17 is a transverse cross-sectional view of a portion of the patient's chest and heart illustrating the placement of sutures in the native valve annulus according to the invention.
Figure 18:
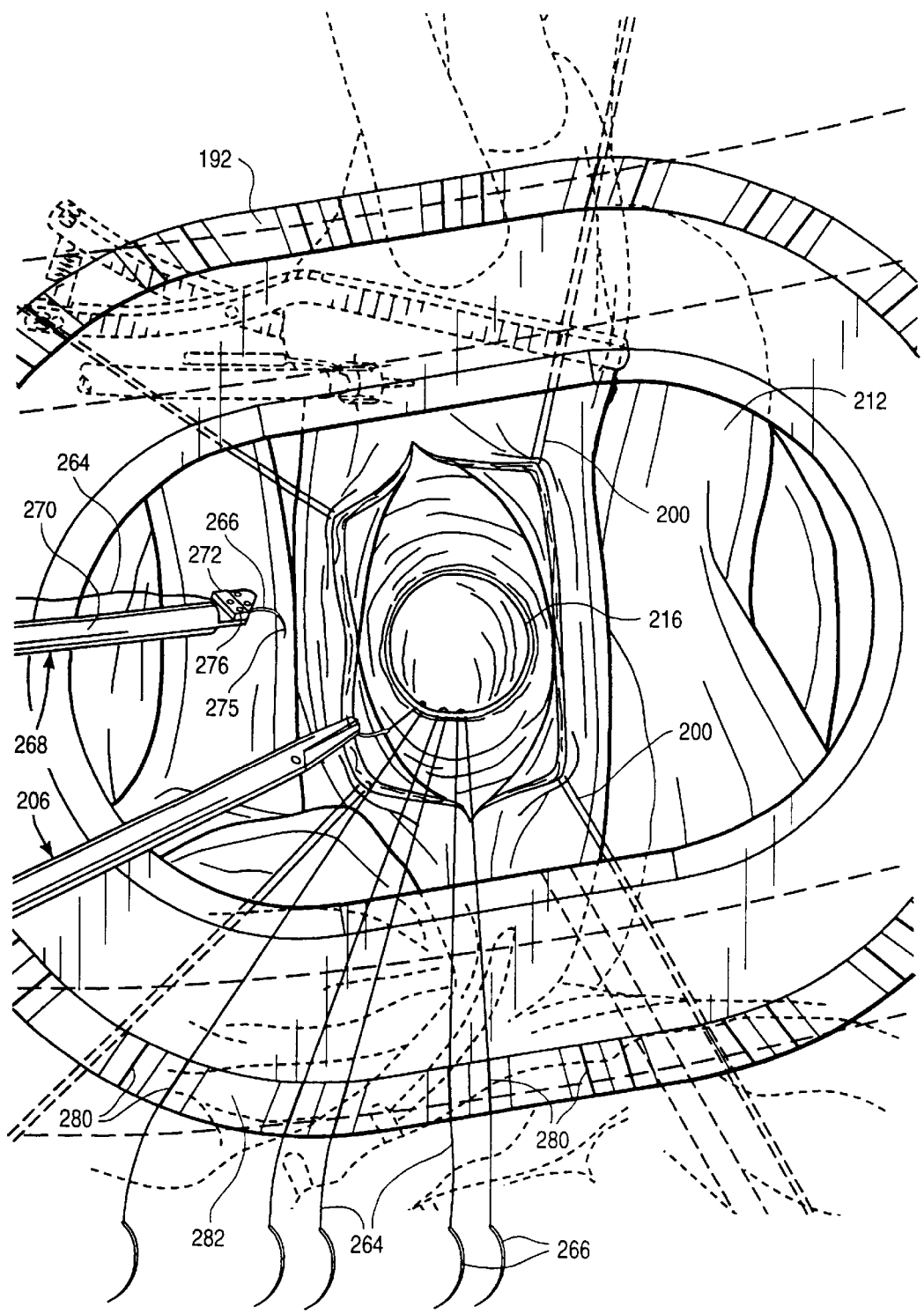
FIG. 18 is a view of the aortotomy and the aortic valve through an oval-shaped access port placed in an intercostal space in the patient's chest, illustrating the placement of sutures in the native valve annulus according to the invention.
Figure 19:
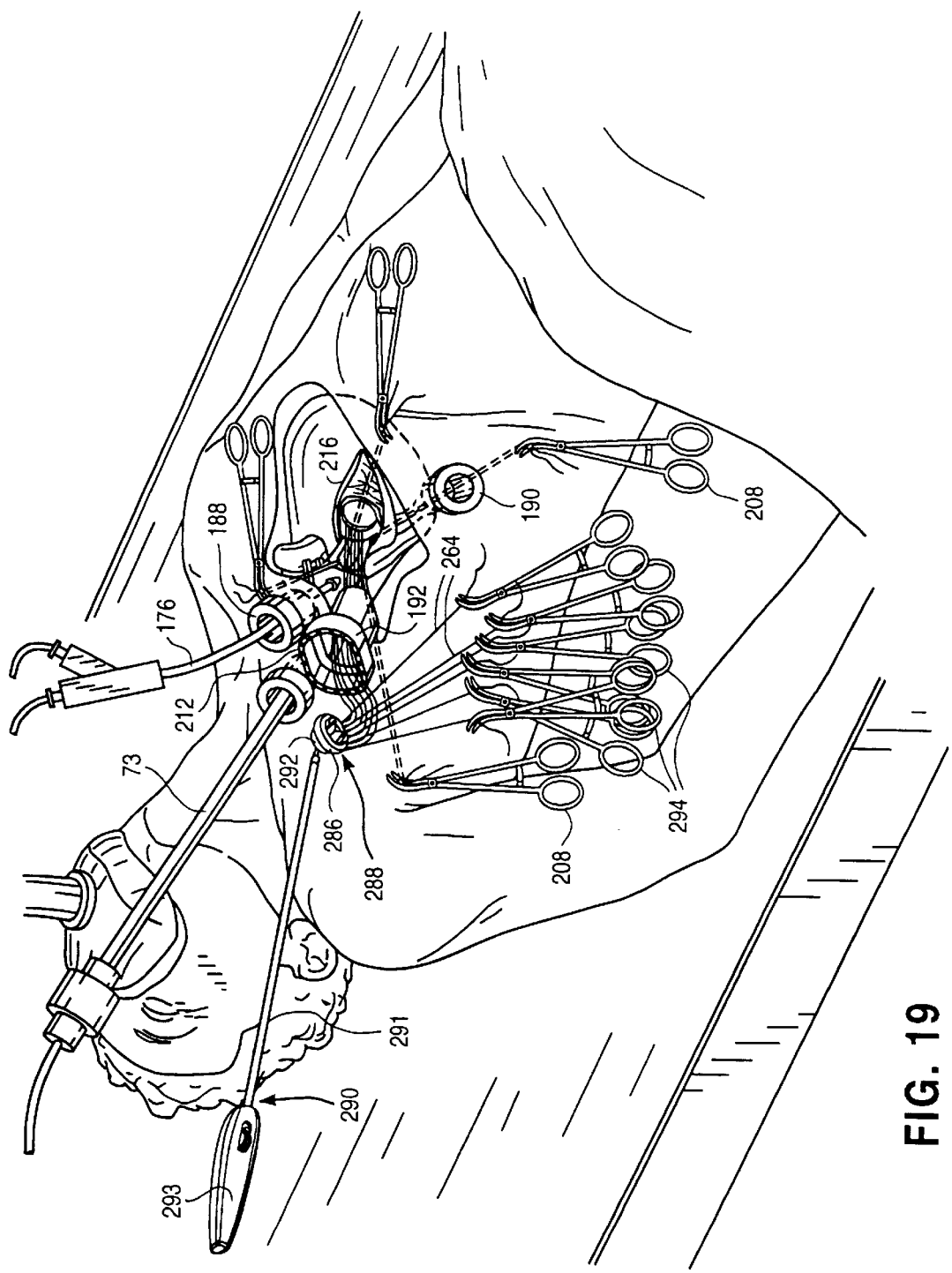
FIG. 19 right lateral elevational view of the patient's chest illustrating the placement of sutures through a prosthetic valve according to the invention.

In order to implant most mechanical valve prostheses, a plurality of sutures 264 are placed in the native valve annulus to form mattress stitches or inverted mattress stitches. As shown in FIGS. 17–18, sutures 264 are double-armed with arcuate needles 266 on both ends, and are placed in valve annulus 216 using a specialized rotational needle driver 268, described in detail in copending application Ser.

No. 08/594,869, entitled "Endoscopic Suturing Devices and Methods", which is hereby incorporated herein by reference. Rotational needle driver 268 has a shaft 270 with a rotatable carriage 272 at its distal end a handle 274 at its proximal end. One of needles 266 is releasably held in carriage 272 such that the needle's sharp point 274 is exposed outside of the carriage. Carriage 272 is rotatable about a pin 276 in shaft 270. An actuator button 278 is slidably mounted to handle 274 and is coupled to carriage 272 by a linkage (not shown) such as a slidable rod within a passage in shaft 270. In this way, sliding actuator button along handle 274 rotates carriage 272 about pin 276. Carriage 272 may be configured to drive sharp point 275 of needle 266 in either a distal or proximal direction, depending upon whether it is desired to drive the needle from the ventricle toward the aorta, or from the aorta toward the ventricle. In the embodiment illustrated, rotational needle driver 268 is set up to drive needle 266 from the left ventricle 222 toward aorta 186. Carriage 272 holding needle 266 is positioned through access port 192, through aortotomy 184 and through valve annulus 216. Sharp point 275 of needle 266 is then positioned so as to penetrate the valve annulus a distance of about 1–5 mm from the inner edge of the annulus, as visualized by looking through access port 192 or under thoracoscopic visualization. When the needle is properly positioned, actuator button 278 is moved along handle 274 to translate needle 266 through valve annulus 216. Once sharp point 275 emerges from the annulus within the aorta, the needle may be picked up with thoracoscopic needle drivers 206 positioned through access port 192 (or through a separate access port). In an alternative embodiment, a needle pick-up mechanism (not shown) is provided on needle driver 268 to allow needle 266 to be picked up without the use of a separate instrument, as described in the above-mentioned patent application Ser. No. 08/594,869, entitled "Endoscopic Suturing Devices and Methods". When needle 266 is picked up, it is drawn through valve annulus 216 and withdrawn from the chest through lumen 212 of access port 192. A total of 10–20 sutures are placed in valve annulus 216 in this way.

Because of the large number of sutures that are placed in valve annulus 216, a suture organizing device is provided outside the chest to keep the sutures orderly and free of tangles. In a preferred embodiment, a suture organizer 279 is disposed on the proximal end of access port 192 itself, the suture organizer including a plurality of radial slits 280, usually 12–24 pairs, arranged around the circumference of a rim 282 on access port 192. Slits 280 are configured to frictionally engage sutures 264 placed into the slits, allowing each suture 264 to be placed in valve annulus 216, drawn out of the chest and placed in one of slits 280 until all of the sutures have been placed. Other aspects of suture organizer 279 are described in copending application Ser. No. 08/485, 600, which has been incorporated herein by reference.

In the case of certain bioprosthetic valves and other types of replacement valves, techniques may be used for securing the valve to the heart which do not require a plurality of sutures to be placed in valve annulus 216. For example, some tissue valves are secured using a single continuous length of suture to make a running stitch around the sewing ring of the replacement valve. In other cases, staples, clips or other fastening devices may be used to secure the replacement valve to the native annulus or adjacent tissue. In such cases, it may be unnecessary to place sutures or other fasteners in valve annulus 216 until after the replacement valve has been introduced into the chest and positioned at the aortic valve position.

With all of sutures 264 placed in valve annulus 216 and the ends of sutures 264 organized outside of the chest, each suture is placed through sewing ring 286 of prosthetic valve 288, which is held by a delivery handle 290. Delivery handle 290 has an elongated shaft 291 and a handle 293 at its proximal end, and may be the same handle used in valve sizing device 250 described above in reference to FIG. 16, with sizing disk 258 removed from tongue 254. Prosthetic valve 288 is releasably held on a holder 292 which includes a slot or aperture (not shown) configured to receive a tongue on delivery handle 290 similar to tongue 254 on valve sizing device 250. Various other details concerning the construction of delivery handle 290, prosthetic valve 288, and holder 292 are described in copending application Ser. No. 08/281, 962 and application Ser. No. 08/485,600, which have been incorporated herein by reference. A needle driver of conventional construction is used to grasp each of needles 266 and drive it through sewing ring 286. After each needle is driven through the sewing ring, it is secured by means of a hemostat 294 or by placement in a suture organizer positioned on or near the patient's chest.

Delivery handle 290 is configured to allow prosthetic valve 288, mounted to holder 292, to be delivered through an intercostal access port with minimal retraction of the ribs. If the annular sewing ring 286 has a central axis extending through it (generally defining the direction of blood flow through the valve), delivery handle 290 preferably holds prosthetic valve 288 in an orientation in which the central axis of sewing ring 286 is generally perpendicular to the longitudinal axis of shaft 291, wherein the prosthetic valve, holder, and delivery handle have a minimum profile in a direction perpendicular to the longitudinal axis of shaft 291. This will allow prosthetic valve 288 to be delivered through an intercostal space without removing or cutting the ribs or the sternum, and, in most patients, without retracting the ribs. Certain types of prosthetic valves, particularly tissue valves, may have a larger profile due to the height of the valve commissures. However, even for these prosthetic valves, delivery handle 290 is adapted to hold the prosthetic valve in an orientation of minimum profile, allowing the prosthetic valve to be positioned into the chest with minimal retraction of the ribs, usually with less than about 10 mm of retraction of each rib from its natural, undeflected position, and preferably less than about 5 mm from the rib's natural, undeflected position.

Figure 20:
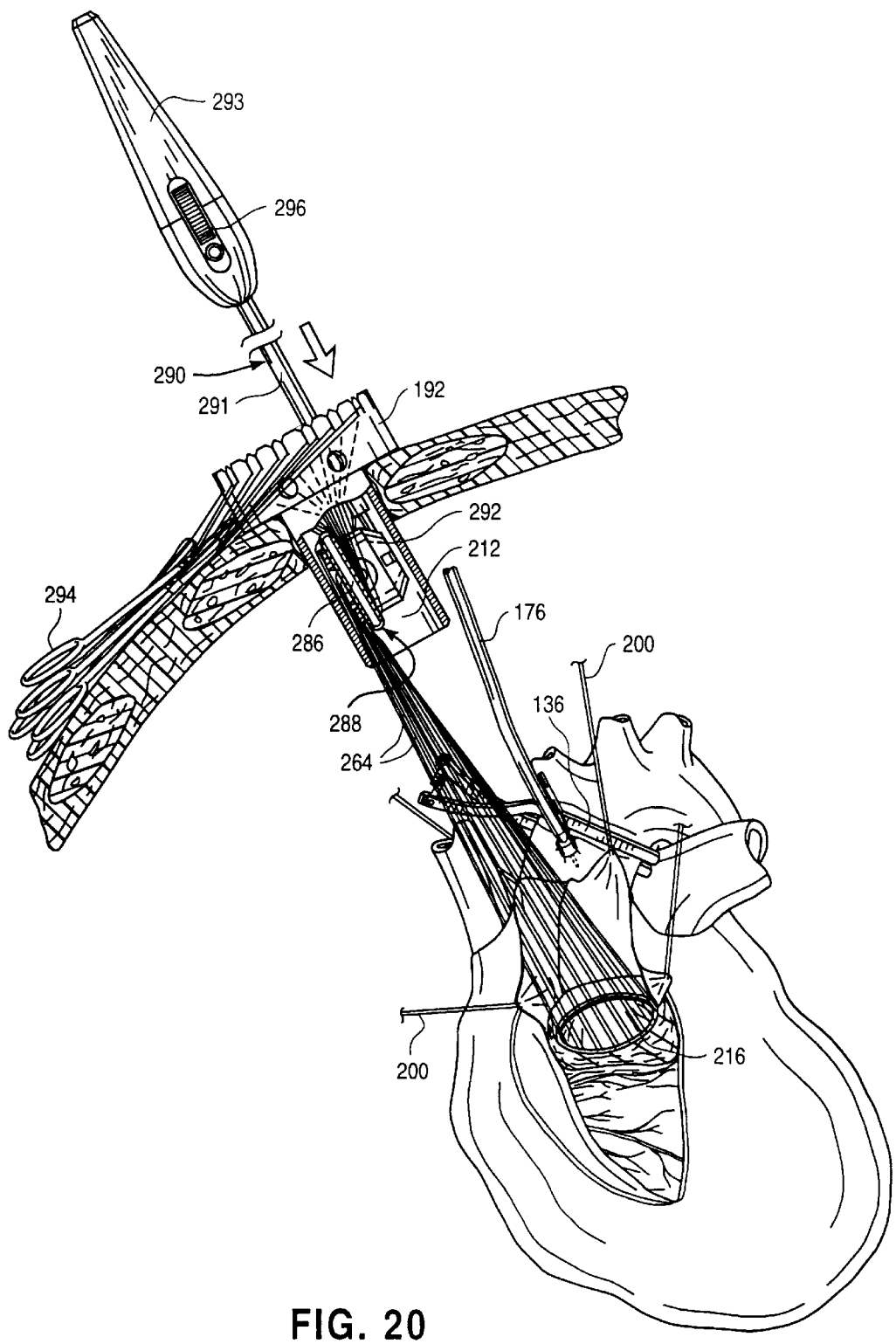
FIG. 20 is a transverse cross-sectional view of a portion of the patient's chest and heart illustrating the positioning of a prosthetic valve into the chest through an access port according to the invention.

To facilitate positioning prosthetic valve 288 through an intercostal space without interference with the ribs or tissue of the chest wall, the prosthetic valve is placed through inner lumen 212 of access port 192, as illustrated in FIG. 20. Inner lumen 212 is specially adapted to allow prosthetic valve 288 to pass through it in an edge-first orientation. Preferably, the prosthetic valve is positioned through lumen 212 such that the central axis of sewing ring 286 is generally perpendicular to the longitudinal axis of inner lumen 212. At the same time, the overall profile of access port 192 is minimized so as to require an incision in the chest wall of minimum size. In a preferred embodiment, the cross-section of inner lumen 212 in a direction perpendicular to its longitudinal axis has a cross-sectional length which is substantially greater than its cross-sectional width, with an oval, rectangular, racetrack, elliptical, or other shape suitable for passage of prosthetic valve 288 in the edge-first orientation illustrated. The cross-sectional length will be just larger than the outer diameter of sewing ring 286, usually 17–35 mm, and the cross-sectional width will be just larger than the height of the valve parallel to the central axis of sewing ring 286, ranging from about 5–25 mm for mechanical valves, to about 15–30 mm for tissue valves.

Of course, a variety of other devices may be used to retract the chest wall tissue to allow prosthetic valve 288 to be introduced into the chest, including a soft tissue retractor designed to atraumatically retract tissue adjacent to an intercostal incision to create an opening in the chest without retracting the ribs. Alternatively, a conventional retractor with a pair of movable parallel rigid blades may be positioned in an intercostal incision parallel to the ribs, the distance between the blades being adjustable to create an opening in the intercostal space of a desired width. Such an adjustable retractor may be desirable where the height and outer diameter of the prosthetic valve are both larger than the distance between the ribs in the intercostal space through which the prosthetic valve is to be positioned, as may be the case with certain types of tissue valves. In this way, the ribs may be slightly retracted temporarily to allow the prosthetic valve to be positioned into the chest, and the retractor then re-adjusted to allow the ribs to return to their natural, undeflected positions for the remainder of the procedure, thus minimizing the trauma associated with such retraction.

As prosthetic valve 288 is advanced into the chest, tension is maintained on sutures 264 by means of hemostats 294 or an assistant's hands so that sewing ring 286 slides along sutures 264 toward aortic valve annulus 216. Delivery handle 290 has a length sufficient to allow prosthetic valve 288 to be positioned at the native aortic valve position in the heart with handle 293 remaining outside the chest, shaft 291 preferably having a length of at least about 15 cm. Once inside the chest, prosthetic valve 288 may be reoriented into an orientation suitable for securing the valve to valve annulus 216, i.e., an orientation in which sewing ring 286 may be positioned parallel to and axially-aligned with valve annulus 216 (illustrated in FIG. 21). Such reorientation may be accomplished by simply removing prosthetic valve 288 from delivery handle 290, but is preferably accomplished by pivoting prosthetic valve 288 relative to shaft 291 by sliding an actuator button 296 on handle 293. This pivots a tongue at the distal end of shaft 291 to which holder 292 and prosthetic valve 288 are attached, in a manner like that described above with reference to valve sizing device 250 of FIG. 16 (and described in copending application Ser. No. 08/485,600, which has been incorporated herein by reference). Usually, prosthetic valve 288 is reoriented such that the central axis of sewing ring 286 is generally parallel to the longitudinal axis of shaft 291 plus or minus about 30°, although the exact angular orientation may vary according to the location of access port 192 and patient anatomy.

Figure 21:
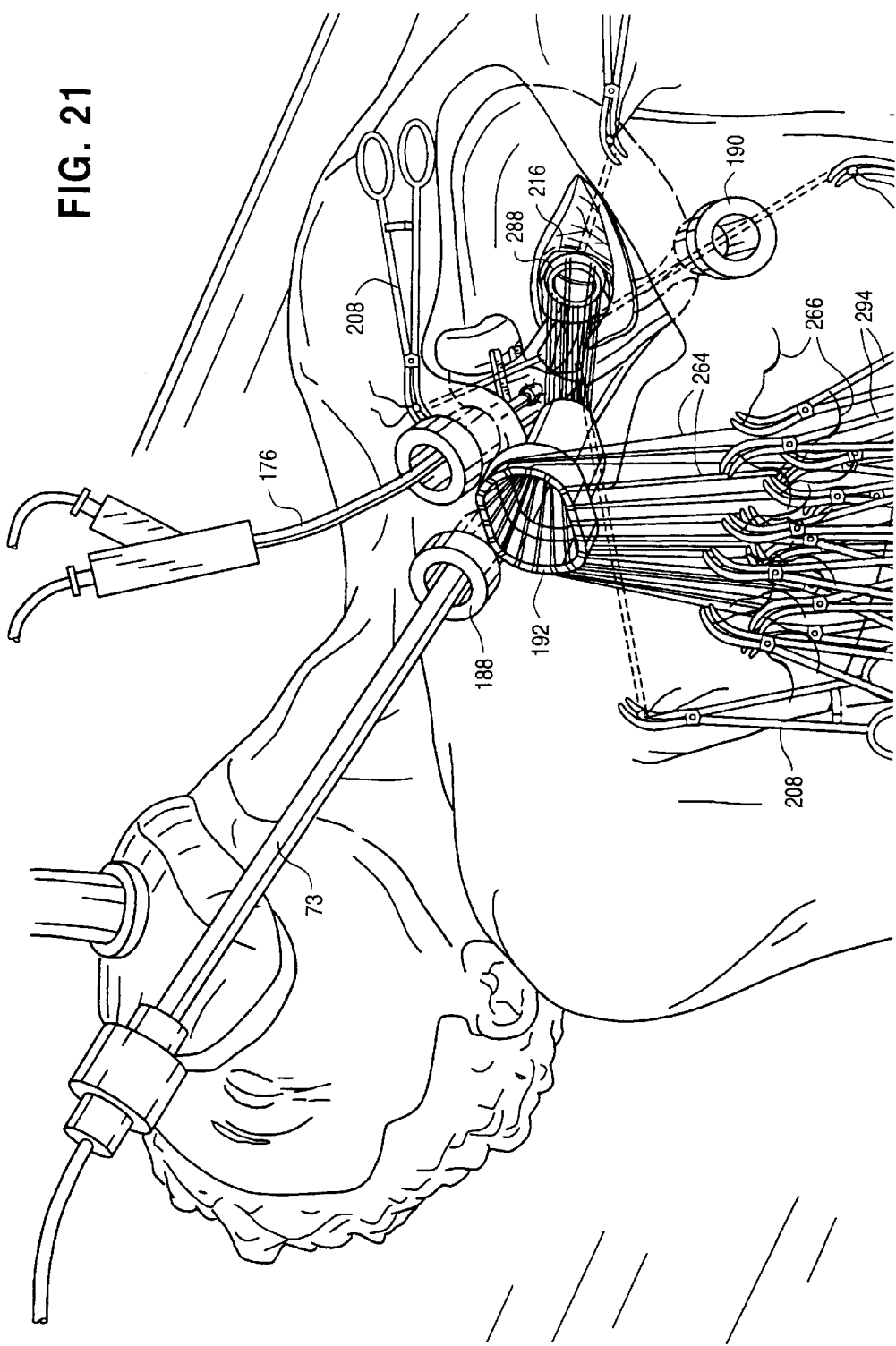
FIG. 21 is a right lateral elevational view of the patient's chest with a portion of the chest cut-away illustrating the placement of the prosthetic valve at the native valve position in the heart.

Prosthetic valve 288 is positioned adjacent to the valve annulus 216 and then released from delivery handle 290, which may then be removed from the chest, as illustrated in FIG. 21. Prosthetic valve 288 is preferably released by cutting a suture (not shown) on holder 292 as frequently provided on conventional prosthetic valve holders. This allows a movable portion of holder 292 to pivot away from sewing ring 286, releasing the prosthetic valve from the holder, as described in greater detail in copending application Ser. No. 08/281,962, which has been incorporated herein by reference.

Figure 22:
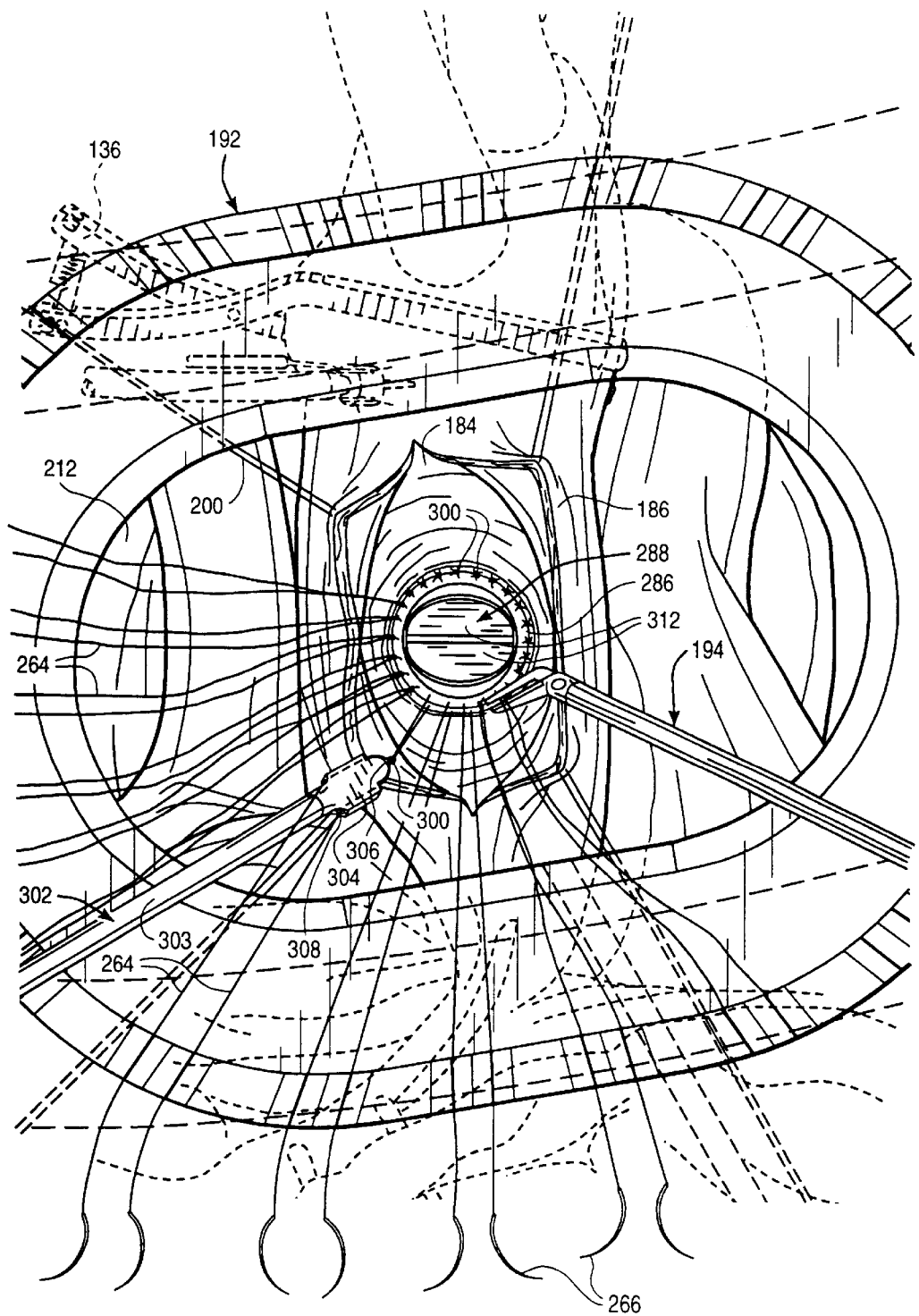
FIG. 22 is a view of the aortotomy and the aortic valve through an oval-shaped access port placed in an intercostal space in the patient's chest, illustrating the tying and trimming of sutures to secure a prosthetic valve in the heart according to the invention.

Referring now to FIG. 22, knots 300 are formed in each of sutures 264 outside of the chest, and a thoracoscopic knot pusher 302 is used to push knots 300 along sutures 264 through lumen 212 of access port 192, through aortotomy 184 and against sewing ring 286 of prosthetic valve 288. Knot pusher 302 preferably has an elongated shaft 303 to which is attached a head 304 with a convex curvature on its distal end 306 and a pair of axial channels 308, 310 along its lateral sides, as described in copending application Ser. No. 08/288,674, filed Aug. 10, 1994, which is hereby incorporated herein by reference. One end of each suture is threaded through channel 308, a knot 300 is formed in the suture distally of head 304, and the other end of the suture is positioned in channel 310. While holding the ends of suture 264 in tension, knot pusher 302 is advanced toward prosthetic valve 288, engaging knot 300 with distal end 306 and sliding the knot along suture 264 until it is against sewing ring 286. Several knots are formed in each suture in this manner. The ends of sutures 264, along with needles 266, are then trimmed off above knots 300, using thoracoscopic angled scissors 194 or other suitable cutting device.

With prosthetic valve 288 successfully secured in the aortic valve position, the movable leaflets 312 may be tested for proper action by inserting a probe (not shown) through an access port and exerting a gentle force against the outer edges of the leaflets. The probe may comprise an elongated shaft with an atraumatic tip of a soft elastomer suitable for contacting the valve leaflets, like that described in copending application Ser. No. 08/485,600, which has been incorporated herein by reference. Alternatively, the probe may include an inner lumen extending to a port at its distal end, the inner lumen being adapted for connection to a source of suction outside the chest, whereby suction may be applied to the valve leaflets to test for proper opening and closing.

Figure 23:
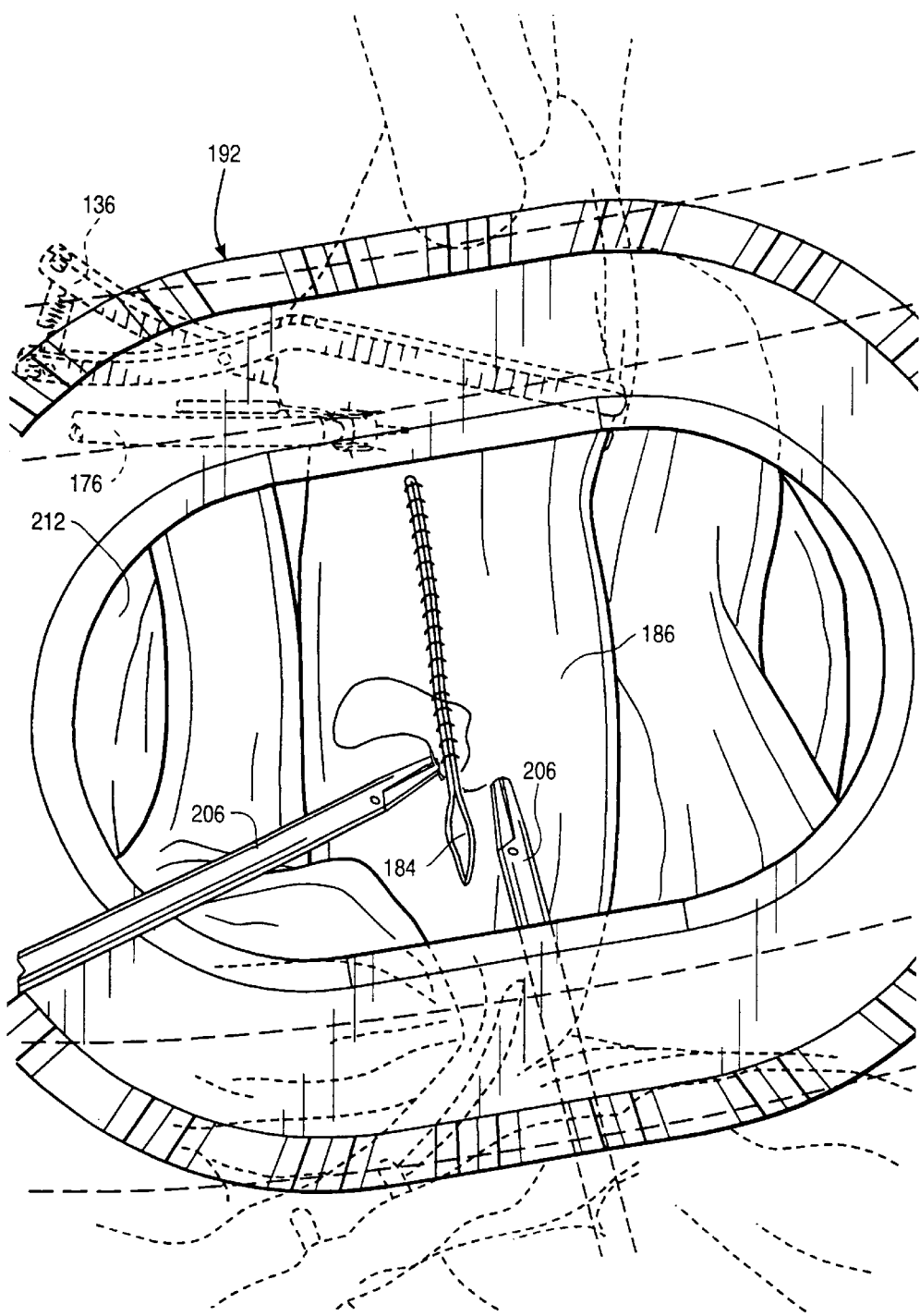
FIG. 23 is a view of the aortotomy and the aortic valve through an oval-shaped access port placed in an intercostal space in the patient's chest, illustrating the closure of the aortotomy according.to the invention.

If leaflets 312 are functioning properly, aortotomy 184 may be closed. This may be accomplished, as illustrated in FIG. 23, by suturing the opposing edges of the aortic incision together using a conventional running stitch applied by means of thoracoscopic needle drivers 206 positioned through access ports 188, 190 or 192. Alternatively, an endoscopic stapler may be used to apply a series of staples across aortotomy 184.

While aortotomy 184 is being closed, it will usually be desirable to remove any air from within the left ventricle and ascending aorta 186 upstream of aortic clamp 136. This is accomplished by first reducing venous drainage of the heart via venous cannula 22 to allow blood to flow from the right side of the heart into the left ventricle, thereby filling the left ventricle with blood. This forces air out of the left ventricle into the ascending aorta. Preferably, the patient will be positioned so that the superior or anterior aspect of the aortic arch is upward so that any air collects at a point where it can be suctioned out through delivery cannula 176. An irrigation fluid such as saline may also be delivered through delivery cannula 176 into the ascending aorta and left ventricle to assist in displacing air to the upper part of the ascending aorta near delivery cannula 176. Additionally, thoracoscopic instruments may be positioned through intercostal access ports to depress and collapse the heart, forcing out any air in the left ventricle. Heart manipulation devices may also be positioned through an access port to lift and/or rotate the heart so that any air tends to flow through the aortic valve into the ascending aorta, where it may be suctioned out. Further, small needles may be used to aspirate air from the left ventricle and/or aorta.

In an alternative technique of keeping air out of the heart during the procedure, the chest cavity may be flooded with a gas such as carbon dioxide at the outset of the procedure to prevent any air from entering the chest through the access ports. A gas delivery tube may be introduced through an intercostal access port, or a gas delivery lumen may be provided in a wall of the one of the access ports themselves through which the gas is delivered. To facilitate maintaining the gas within the chest, the access ports may be provided with gaseous seals such as those commonly used in laparoscopic trocar sleeves which provide a gas-tight seal both when an instrument is introduced through the port, as well as when the instrument is removed. These and other techniques for removing air from the heart and aorta are disclosed in copending application Ser. No. 08/585,871, filed Jan. 12, 1996, entitled "Methods and Apparatus for Preventing Air Embolism When Performing A Procedure On A Patient's Cardiovascular System," which is incorporated herein by reference.

With de-airing complete, cardiac function may be allowed to resume. The patient's head is temporarily tilted head-down to prevent emboli from entering the cerebral circulation. Aortic clamp 136 (or other aortic occlusion device) is removed from ascending aorta 186 to allow oxygenated blood delivered via arterial return cannula 26 to flow into the ascending aorta and into the coronary arteries. To remove clamp 136, clamp applier 140 (FIGS. 7–8) is reintroduced into the chest via access port 192, and proximal extremities 154, 156 are engaged by clamp applier jaws 162 and actuated so as to release locking mechanism 148, allowing jaws 142, 144 to return to an open position. Clamp 136 is then withdrawn from the chest cavity. Oxygenated blood is then permitted to flow through the coronary arteries to perfuse the myocardium, whereupon cardiac contractions will quickly resume. In the event that cardiac function does not return spontaneously, electrical defibrillation may be utilized to restore normal heart beat. Defibrillation electrodes may be placed on the heart via intercostal access ports, or external paddles of conventional construction may be used on the surface of the chest, and an electrical charge may then be delivered to stimulate the heart.

When cardiac contractions have resumed, it may still be desirable to maintain suction through delivery cannula 176 so as to remove any air or other emboli which may be present in the aorta or left ventricle. When it is believed that such emboli are no longer present, delivery cannula 176 is removed from ascending aorta 186 and purse-string suture 182 (FIG. 8) is tightened securely and knotted to close the puncture in the aorta. Thoracoscopic needle drivers 206 may be used for this purpose. Thoracoscopic scissors are then used to trim the ends of purse-string suture 182.

The patient is then weaned from cardiopulmonary bypass in the conventional manner, and venous cannula 22, arterial return cannula 24, coronary sinus catheter 52, any other catheters utilized in the procedure, and access port 188, 190, 192, are removed from the patient. Chest drainage tubes may be placed temporarily through incisions used for access, or through additional incisions. All other thoracic and vascular punctures and incisions are closed, and the patient is recovered from anesthesia.

While the invention has been described in the context of aortic valve replacement, various other procedures may be performed using the methods of the invention, including repair or replacement of the mitral, pulmonary or tricuspid valves; repair of atrial and ventricular septal defects and patent ductus arteriosus by means of stapling, suturing or patch-applying instrument positioned into the heart; transmyocardial revascularization by means of a laser introduced into the heart; electrophysiological mapping and ablation by means of a mapping and ablation catheter positioned into the heart; performance of a Cox maze procedure by means of a cutting or ablation device positioned in the heart for transecting the atrial wall to correct atrial fibrillation; and pulmonary embolectomy by positioning a embolus-removal device into the pulmonary artery. Advantageously, in each such procedure, all instruments may be introduced into the heart either through intercostal access ports or via blood vessels with the surgeon's hands outside the chest, eliminating the need for a median sternotomy or other form of gross thoracotomy.

Figure 24:
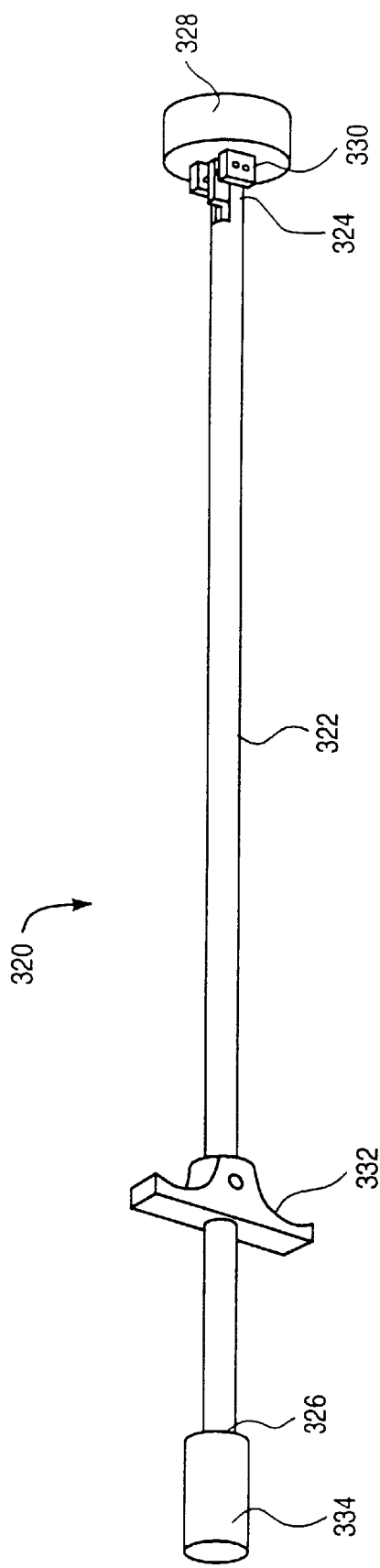
FIG. 24 is a perspective view of an alternative embodiment of a delivery handle according to the invention holding an element schematically representing a valve sizing disk or prosthetic valve.
Figure 25:
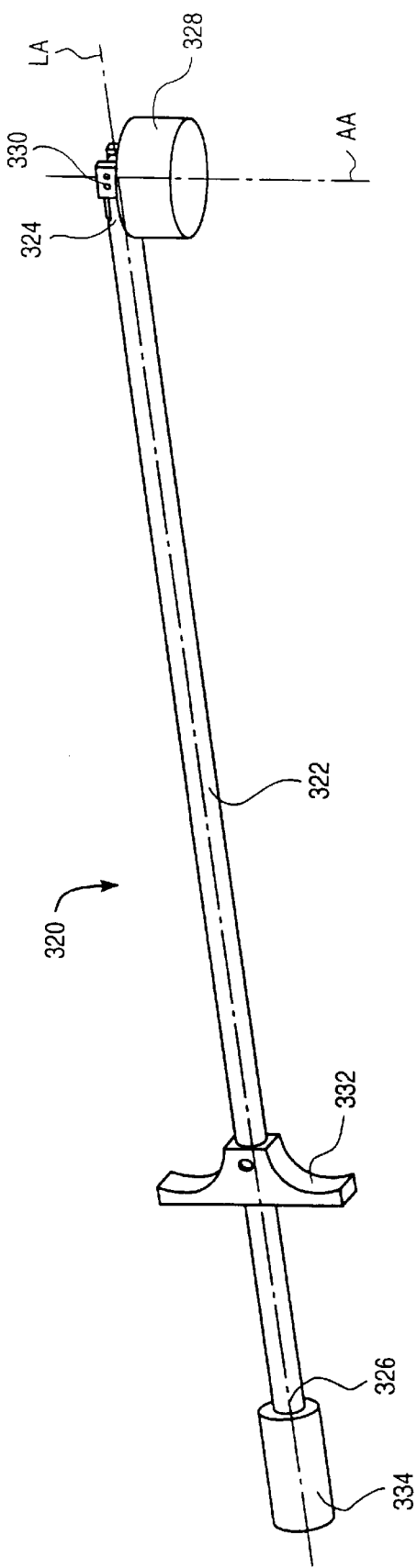
FIG. 25 is a perspective view of the delivery handle of FIG. 24 illustrating the element pivoted into an orientation suitable for positioning through an intercostal access port.
Figure 26:
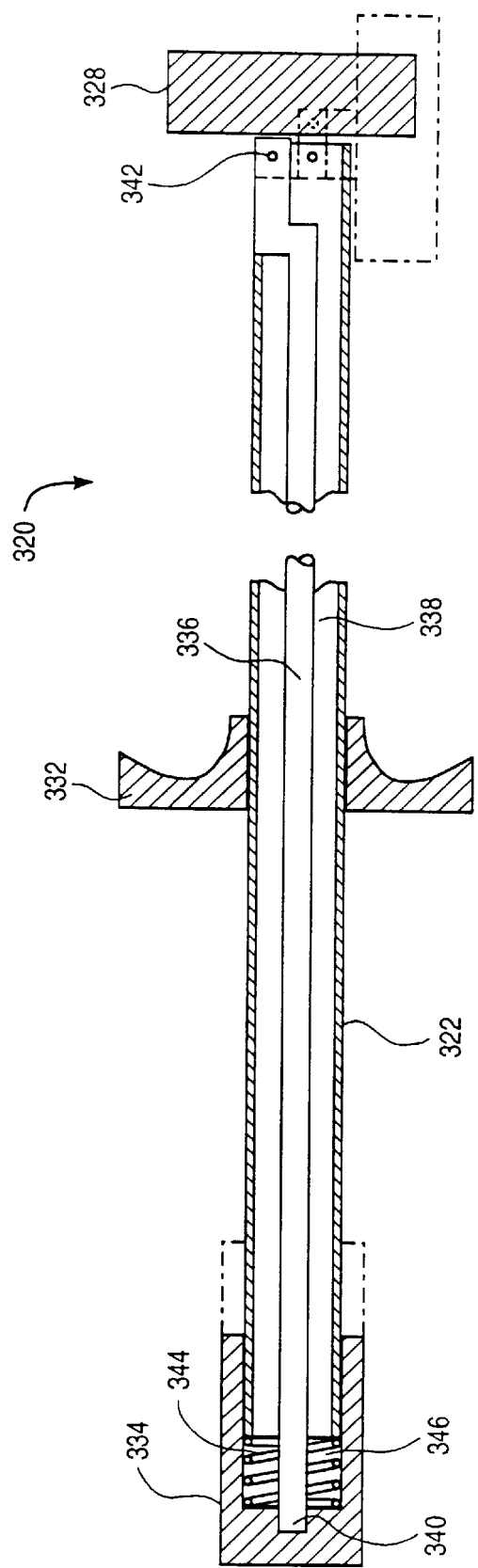
FIG. 26 is a side cross-sectional view of the delivery handle of FIGS. 24 and 25.

Another exemplary embodiment of a delivery handle for positioning either a sizing disk or a replacement valve through an intercostal access port and into the native valve position is illustrated in FIGS. 24–26. In this embodiment, delivery handle 320 comprises a shaft 322 having a distal end 324 and a proximal end 326. A sizing disk or a holder for releasably holding a replacement valve, represented schematically by cylindrical element 328, is pivotably mounted to distal end 324 by a transverse pin 330. A pair of finger grips 332 are fixed to shaft 322 near proximal end 326, and an end cap 334 is slidably received over proximal end 326.

As shown in FIG. 26, a rod 336 extends through an inner lumen 338 in shaft 322. Rod 336 has a proximal end 340 fixed to end cap 334, and a distal end 342 rotatably pinned to element 328 at a point laterally offset from transverse pin 330. A spring 344 is disposed within a bore 346 within end cap 334 and engages the proximal end of shaft 322 to bias end cap 334 and rod 336 in the proximal direction. In this way, element 328 may be pivoted relative to shaft 322 by pushing end cap 334 distally with the thumb while the fingers are placed against finger grips 332. Element 328 is usually rotatable through an angle of at least about 45°, and preferably at least about 90°, relative to shaft 322. In a preferred embodiment, delivery handle 320 is configured to position element 328 in an orientation suitable for introduction through an intercostal access port without removing, cutting, or significantly retracting the ribs. As illustrated in FIG. 25, element 328 is preferably movable into an orientation in which the central axis AA extending axially through cylindrical element 328 is generally perpendicular +/−20° relative to the longitudinal axis LA of shaft 322. In this way, the profile of delivery handle 320 together with element 328 as seen from the distal end of the device is minimized. Element 328—whether a sizing disk or replacement valve—may be introduced through an intercostal access port (such as access port 192 of FIGS. 7–24) in the orientation of FIG. 25 by maintaining pressure against end cap 334. Once inside the chest, end cap 334 may be released, allowing element 328 to return to the orientation of FIG. 24, wherein the element is in a suitable orientation for alignment with the native valve annulus for either sizing the annulus or implanting the replacement valve. Usually, element 328 will be oriented such that central axis AA is at an angle of between −45° and 45°, and preferably about 0° +/−20°, relative to the longitudinal axis LA of shaft 322.

Figure 27:
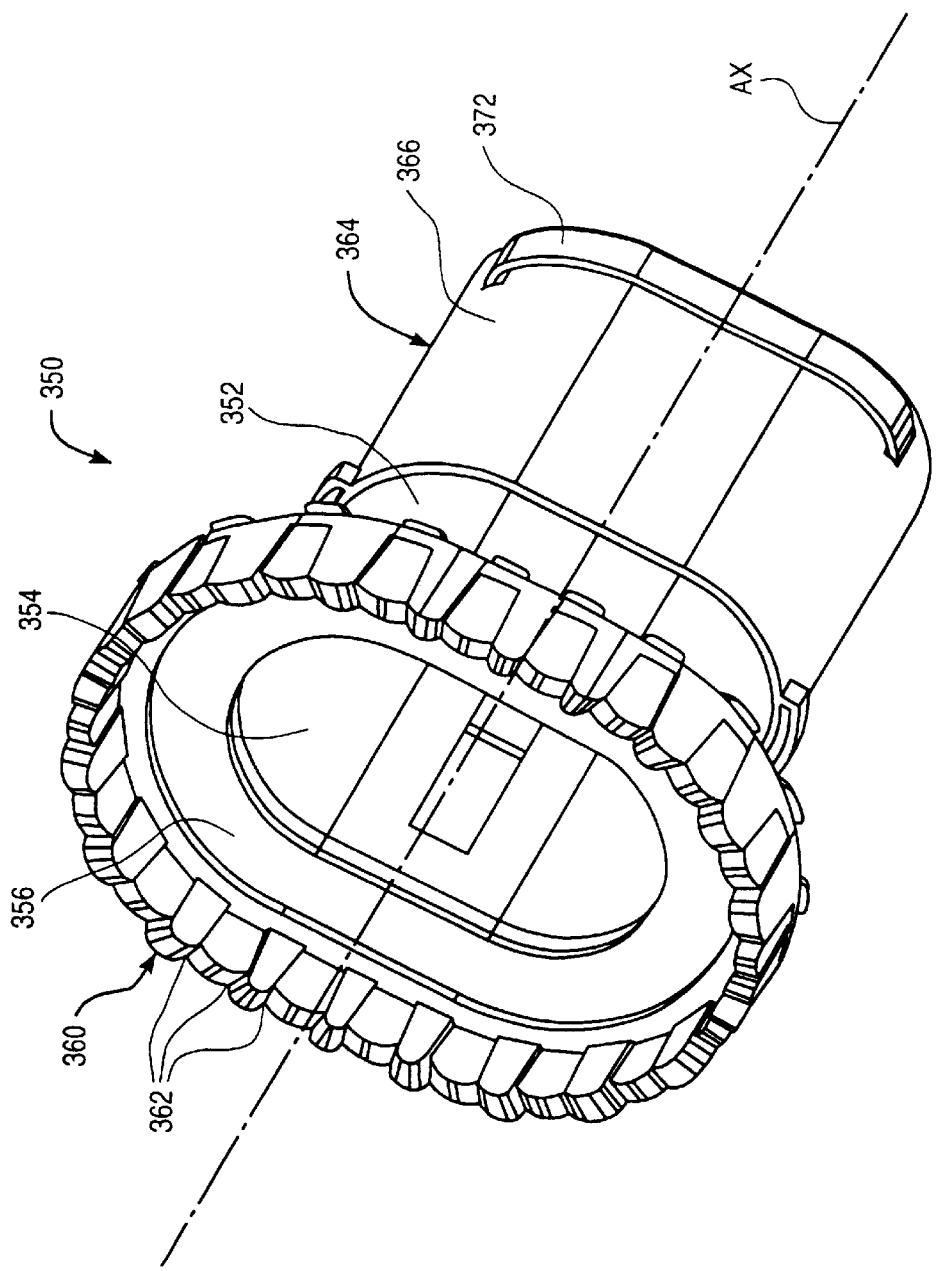
FIG. 27 is a perspective view of an additional embodiment of an access port through which a prosthetic valve may be positioned into the chest according to the invention.
Figure 28:
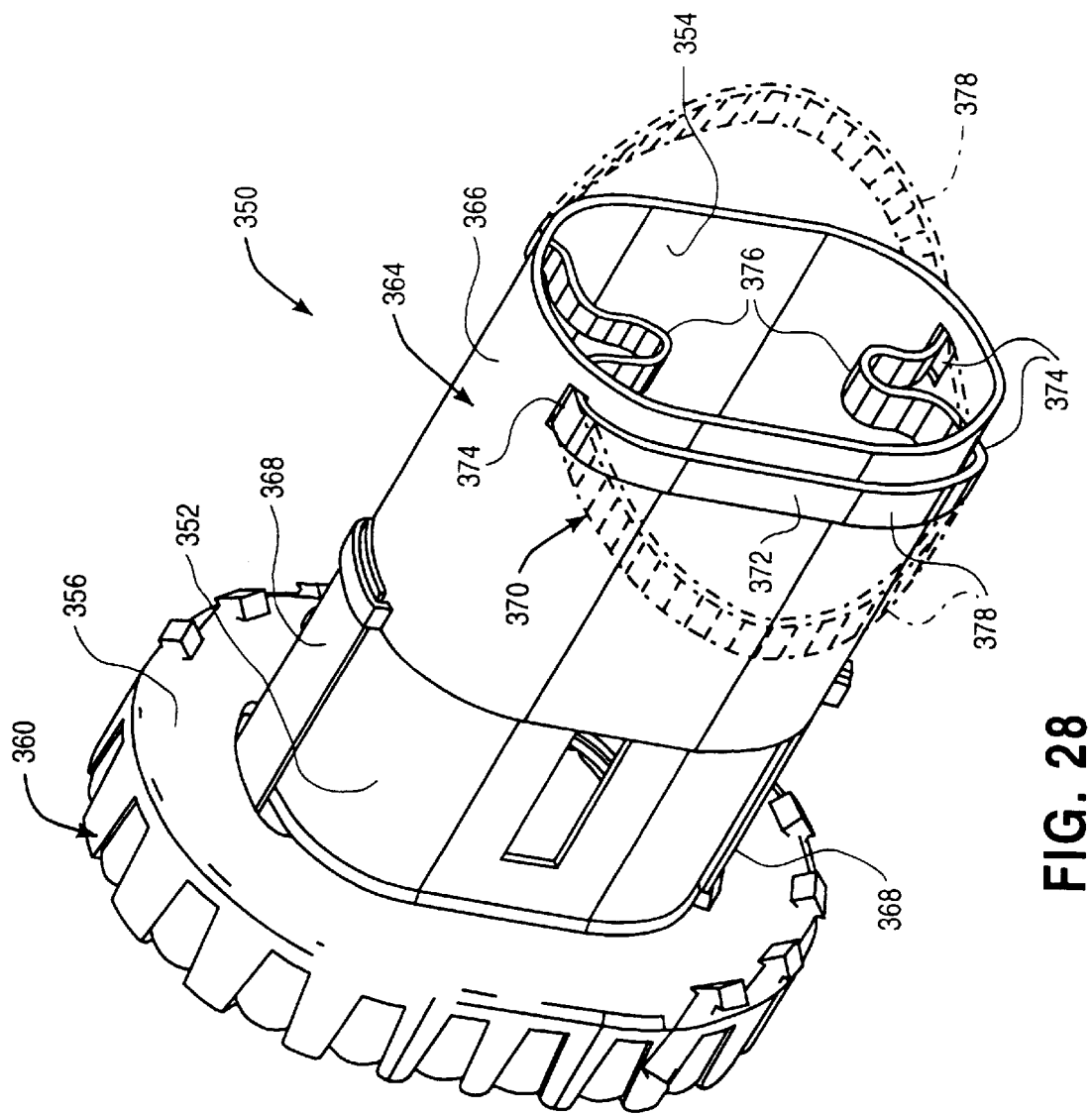
FIG. 28 is a perspective view of the access port of FIG. 27 showing deployment of a retention element for retaining the access port in the chest wall.
Figure 29:
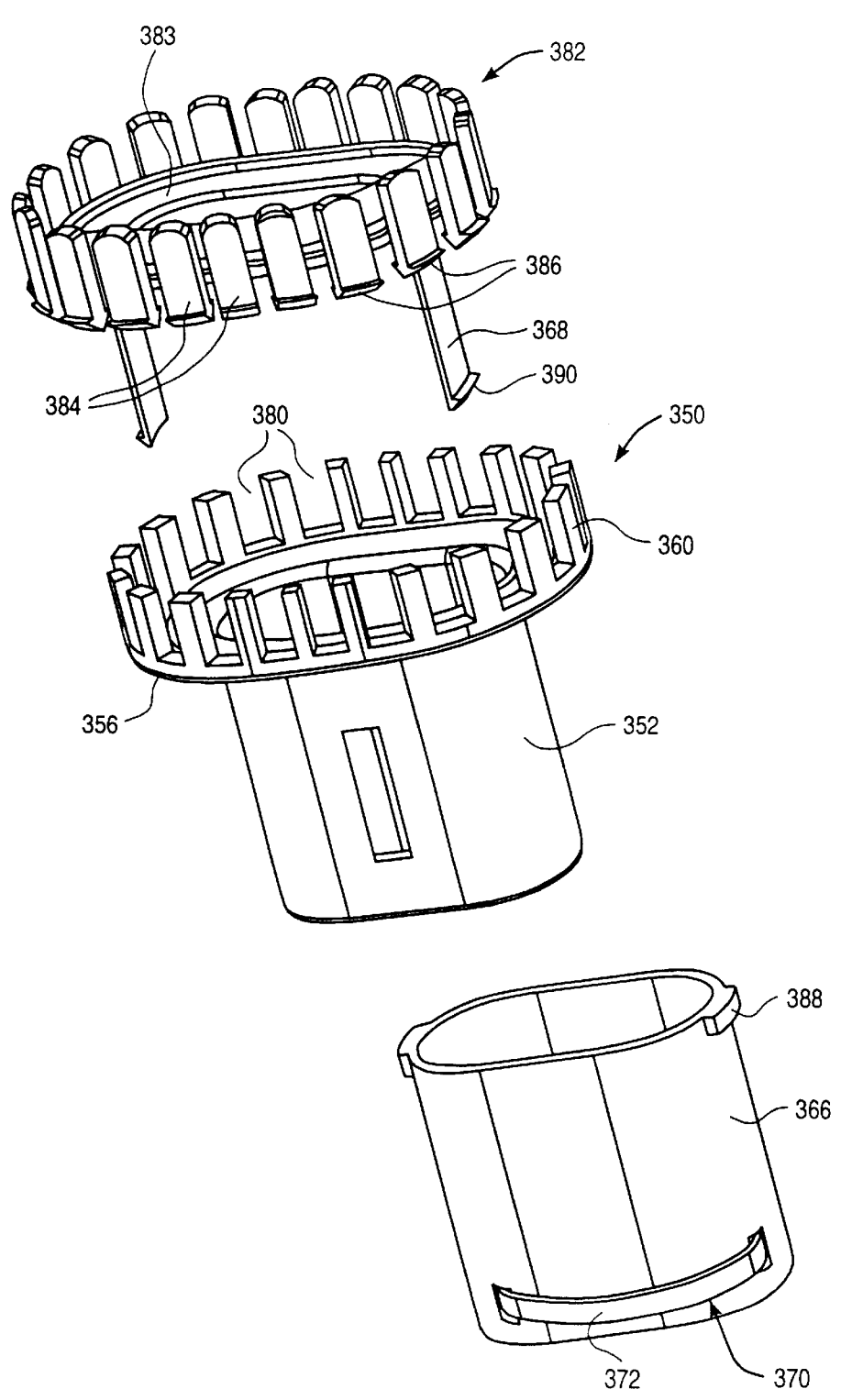
FIG. 29 is a perspective assembly view of the access port of FIGS. 27–28.

FIGS. 27–29 illustrate an additional embodiment of an access port for retraction of tissue within an intercostal space so as to provide an open passageway through which a replacement valve may be positioned into the chest. Access port 350 comprises a tubular body 352 having an axial passage 354 configured to allow a replacement valve to be positioned through it without contacting the inner walls of the axial passage. Tubular body 352 is a metal or biocompatible polymer with sufficient rigidity to retract intercostal tissue and to retain a shape suitable for positioning a replacement valve through the axial passage into the chest. Axial passage 354 preferably has a cross-sectional shape suitable for introducing a replacement valve or sizing disk through it in the edge-first orientation illustrated in FIG. 25, such as oval, elliptical, racetrack, rectangular, trapezoidal, or other suitable shape. Axial passage 354 will have a cross-sectional width orthogonal to a central axis AX of less than about 30 mm, usually about 10 mm–25 mm, and preferably about 15 mm–20 mm. The cross-sectional length of axial passage 354 orthogonal to central axis AX will be larger than the outer diameter of the replacement valve utilized, and usually substantially larger than the cross-sectional width of the axial passage, usually being about 15 mm–50 mm, and preferably being about 25 mm–40 mm. Tubular body 352 has an exterior shape and dimensions suitable for positioning access port 350 in an intercostal space without cutting or removing the ribs, and preferably without significant retraction of the ribs from their natural, undeflected positions (e.g. less than about 10 mm of retraction). In an exemplary configuration, the outer surface of tubular body 352 has a shape corresponding to that of axial passage 354 with a wall thickness therebetween of about 0.25–2 mm, preferably 0.75–1.25 mm. Of course, the exact size and shape of tubular body 352 will be determined by the size and shape of the replacement valve to be utilized in the procedure.

Access port 350 may further include a flange 356 on its proximal end which engages the outer surface of the patient's chest. A suture organizer 358 is preferably mounted to flange 356, and includes an annular wall 360 with a plurality of radial slits 362 in spaced-apart locations around its circumference. Each slit 362 is configured to receive a suture thread and frictionally retain it as described above in connection with FIGS. 18–19.

Access port 350 additionally includes a retention mechanism 364 mounted to a distal extremity of tubular body 352 for retaining the access port in the chest wall. As illustrated in FIG. 28, retention mechanism 364 comprises a sleeve 366 slidably mounted on tubular body 352 and coupled to flange 356 by a pair of tension springs 368, which may be elastomeric bands or cords. A retention element 370 is mounted near the distal end of sleeve 366 and is collapsible for introduction through an intercostal space in the chest wall, and then expandable into a configuration in which the retention element engages the inner wall of the chest. In the exemplary configuration illustrated in the figures, retention element 370 comprises a continuous flexible band 372 which extends through two pairs of slots 374 on opposing sidewalls of sleeve 366 forming two inner loops 376 in the interior of sleeve 366 and two outer loops 378 exterior to sleeve 366. Band 372 is preferably a resilient, flexible metal, plastic or elastomer which is biased into a fully expanded oval or circular ring shape. By compressing outer loops 378 radially inward toward sleeve 366, a portion of band 372 slides through slots 374, enlarging inner loops 376 and collapsing outer loops 378 into the configuration illustrated in FIG. 28. To expand outer loops 378, inner loops are pushed outwardly against sleeve 366.

An assembly view of access port 350 is illustrated in FIG. 29. Annular wall 360 has a plurality of openings 380 formed around its circumference. An insert assembly 382 has a support ring 383 with a plurality of elastomeric inserts 384 attached thereto and configured to fit into openings 380. A lower end of each insert 384 is configured to be received in one of a plurality of slots (not shown) in flange 356 aligned with each opening 380. Each insert 384 has an enlarged lower end 386 which engages the lower surface of flange 356 to retain the insert within opening 380. In this way, the adjacent surfaces of inserts 384 and wall 360 within openings 380 form radial slits 362 (FIG. 27). Inserts 384 will preferably have sufficient compliance to deflect slightly as a suture thread is drawn into slit 362, and sufficient resilience to maintain pressure against the thread to retain it in the slit.

Also attached to support ring 383 are tension springs 368, which may comprise resilient elastomeric bands or cords, extending distally through a pair of appropriately aligned slots (not shown) in flange 383. Sleeve 366 has a pair of ears 388 at its proximal end with axial passages through which tension springs 368 may extend. Each tension spring 368 has a flange or ledge 390 at its distal end which retains the tension spring in ear 388.

Figure 30:
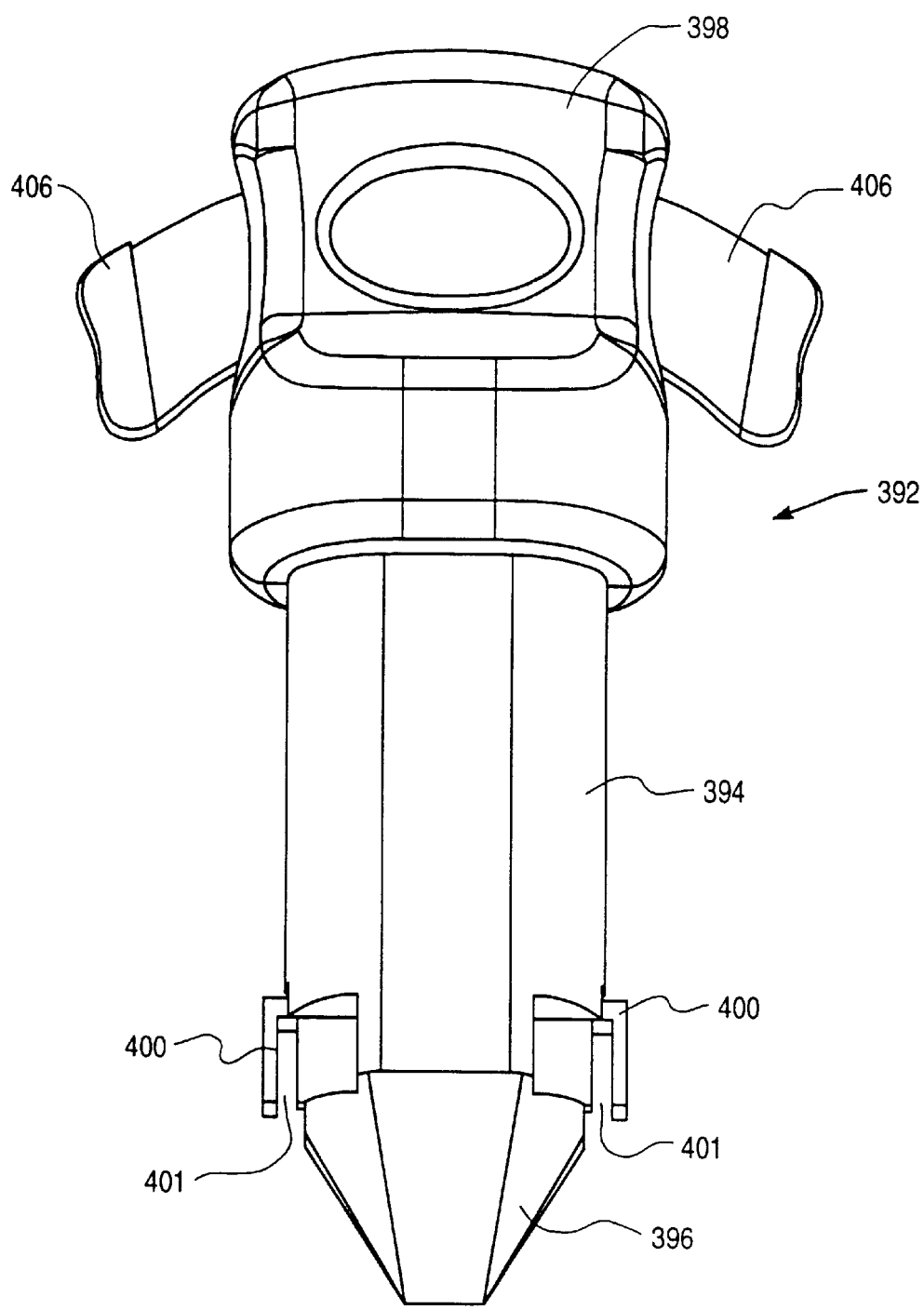
FIG. 30 is a perspective view of an obturator for use in conjunction with the access port of FIGS. 27–29.
Figure 31B:
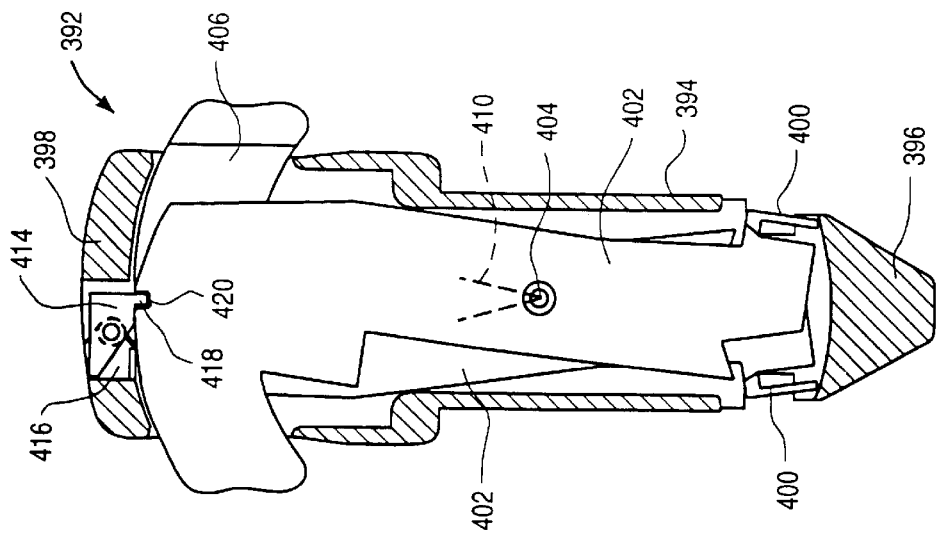
FIGS. 31A–31B are side cross-sectional views of the obturator of FIG. 30 illustrating the actuation a means for retracting the retention means of the access port of FIGS. 27–29.
Figure 31A:
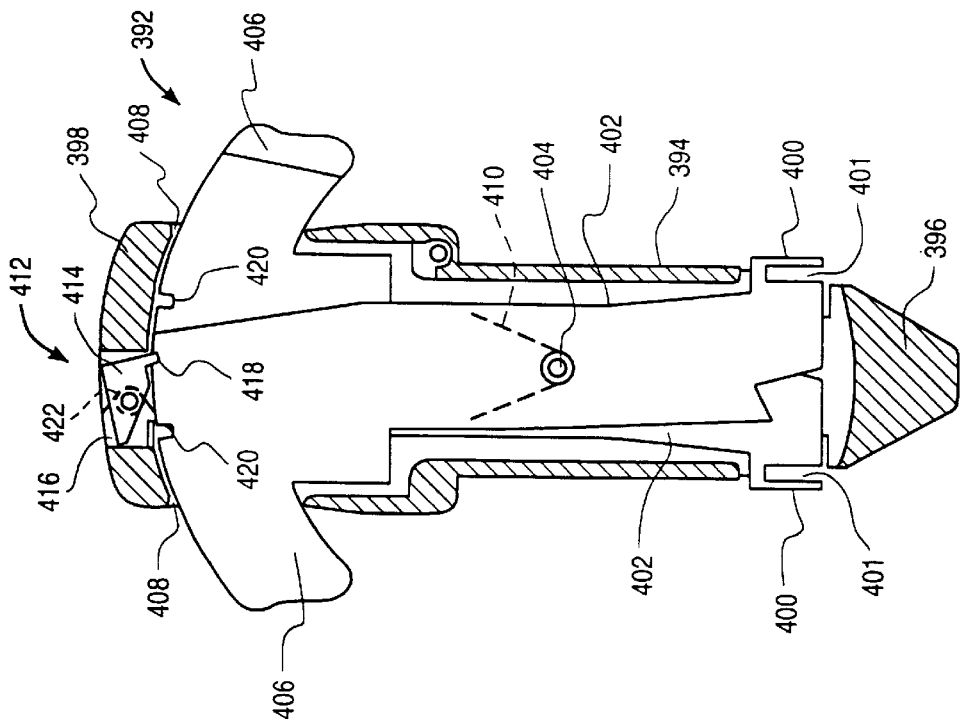

To facilitate expanding and collapsing retention element 370, the invention provides a specialized obturator for use with access port 350, illustrated in FIGS. 30–31. Obturator 392 has a shaft 394 shaped to occlude axial passage 354 of access port 350. A distal end 396 of shaft 394 is tapered to facilitate introduction through a puncture or incision in the chest wall. A handle 398 is fixed to the proximal end of shaft 394. A pair of hooks 400 are movably coupled to shaft 394 near distal end 396 and form a distally-open U-shaped channel 401 configured to receive inner loops 376 of band 372. As illustrated in FIGS. 31A–31B, hooks 400 are mounted to a pair of actuators 402 pivotably mounted to handle 398 by a pin 404 such that actuators 402 move in a scissors-like manner. Actuators 402 each have an outwardly extending button 406 which extends through an aperture 408 in handle 398. Actuators 402 are biased outwardly by a torsion or U-shaped spring 410. In this way, pressing buttons 406 inwardly moves hooks 400 from the outward position illustrated in FIG. 31 A to the inward position illustrated in FIG. 31B.

Obturator 392 further includes a locking mechanism 412 comprising a pivotable locking button 414 mounted within an opening 416 in handle 398. Locking button 414 has a foot 418 extending from a distal surface thereof. Each of actuators 402 has a notch 420 on a proximal surface thereof which is configured to receive foot 418. A torsion spring 422 biases locking button 414 in a clockwise direction. When actuators 402 are pivoted inwardly, foot 418 slides along the proximal surfaces of actuators 402 until notches 420 are aligned. This allows foot 418 to slide into notches 420, locking actuators 402 in the inward position, as shown in FIG. 31B. The locking mechanism is released by pushing on the proximal surface of locking button 414 on the side opposite that of foot 418, pivoting locking button 414 counterclockwise to remove foot 418 from notches 420.

In use, obturator 392 is positioned in axial passage 354 of access port 350 such that hooks 400 extend around inner loops 376 of band 372 to position the band in channels 401. Buttons 406 are then pressed inwardly, drawing inner loops 376 inwardly and collapsing outer loops 378 against the outer surface of sleeve 366. Access port 350 may then be positioned through an incision or puncture through the chest wall between two ribs. When band 372 is inside the chest cavity, locking button 414 is released, allowing actuators 402 and hooks 400 to return to the outward position. Outer loops 378 are thereby deployed into their expanded configuration, and obturator 392 may be removed from axial passage 354. Tension springs 368 pull sleeve 366 toward flange 356 on tubular body 352, compressing the chest wall between band 372 and flange 356. Access port 350 is thus firmly held in position during the procedure. To remove the access port from the chest, obturator 392 is re-inserted into axial passage 354 such that hooks 400 engage inner loops 376, buttons 406 are pressed inwardly to collapse outer loops 378, and access port 350 is withdrawn from the intercostal incision.

Figure 32:
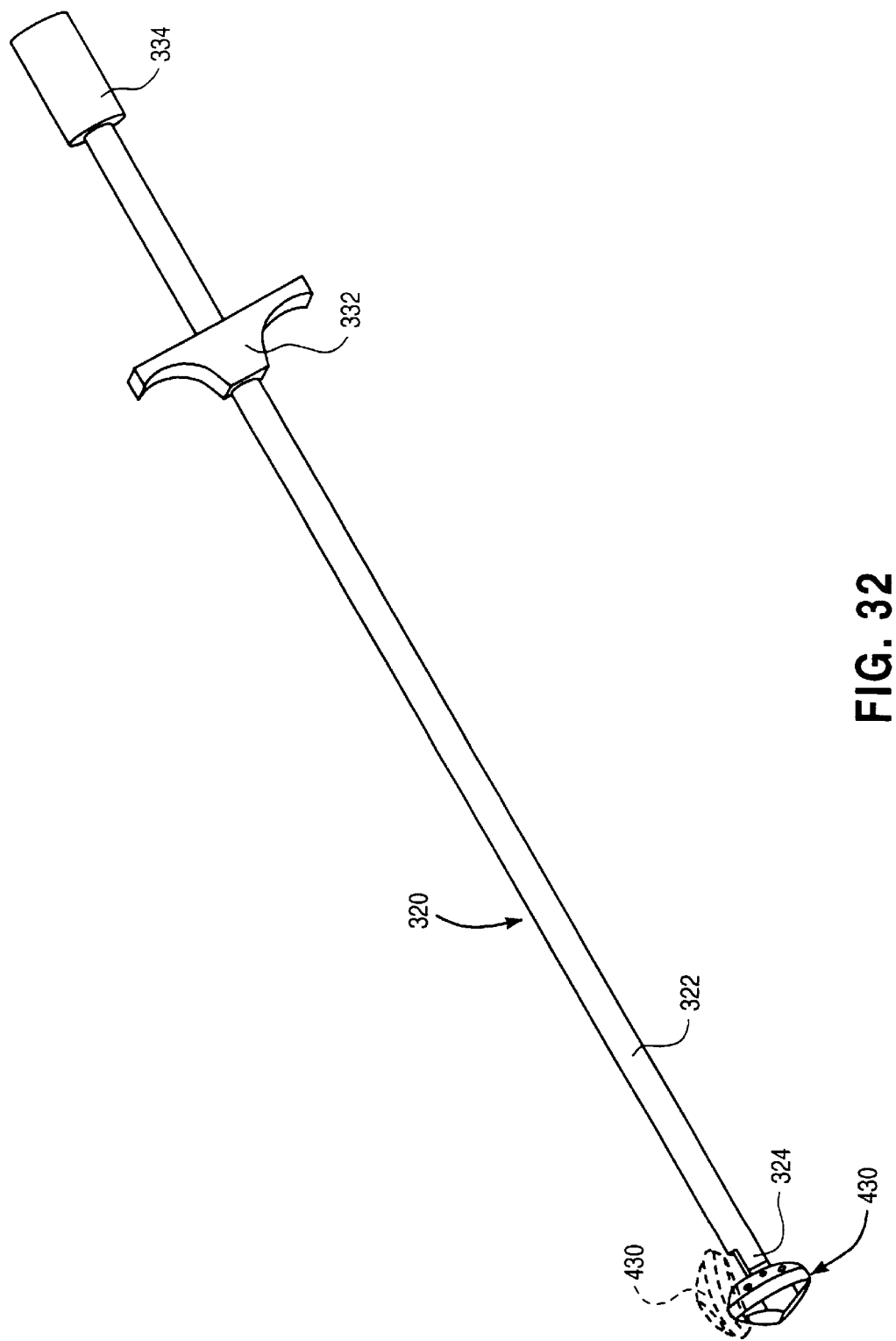
FIG. 32 is a perspective view of the delivery handle of FIGS. 24–26 including an alternative embodiment of a valve holder according to the invention.

Referring now to FIGS. 32–33, a preferred embodiment of a holder for an aortic valve prosthesis according to the invention will be described. As shown in FIG. 32, holder 430 is attached to the distal end of delivery handle 320 in place of element 328, described above in connection with FIGS. 24–26. Holder 430 is pivotable relative to shaft 322 from a first orientation of minimum profile suitable for introduction through an intercostal space, to a second orientation suitable for aligning the prosthetic valve with the native valve annulus so that it may be secured thereto. Preferably, as described above, in the first orientation, holder 430 is positioned such that the central axis of the prosthetic valve sewing ring is generally perpendicular to the longitudinal axis of shaft 322, as shown in phantom in FIG. 32. In the second orientation, holder 430 is preferably positioned so that the central axis of the prosthetic valve sewing ring is generally parallel to the longitudinal axis of shaft 322.

A configuration of holder 430 will be described which is appropriate for use with a mechanical bileaflet aortic valve prosthesis such as the St. Jude Medical Mechanical Aortic Valve. However, it will be understood to those of ordinary skill in the art that holder 430 may be configured to accommodate a wide variety of prosthetic valves without departing from the scope of the invention. As shown in FIGS. 33A–33B, holder 430 is configured to hold prosthetic valve 432 from its downstream side with movable valve leaflets 434 in their closed position. In this position, valve leaflets 434 form a V-shaped space within the interior of the valve surrounded by annular valve body 436 and sewing ring 438. Holder 430 therefore has a peaked or wedge-shaped distal surface 440 with angled faces 441A, 441B forming an angle α of between about 90° and 150°, which fits within the V-shaped space adjacent valve leaflets 434. An annular rim or flange 442 is configured to abut annular sewing ring 438 of prosthetic valve 432. A handle coupling 444 is attached to the proximal surface 446 of holder 430 and is configured to be attached to delivery handle 320. Handle coupling 444 has a transverse channel 448 as shown in FIG. 33B configured to receive the distal end of shaft 322. A pair of holes 450, 452 extend through handle coupling 444 across channel 448 and may be aligned with holes 454, 456 in delivery handle 320 so that pins may be inserted therethrough. In this way, by sliding rod 336, holder 430 pivots relative to shaft 320.

Prosthetic valve 432 may be removably attached to holder 430 in various ways. In a preferred embodiment, sutures are placed through sewing ring 438 and through holder 430 and tied in order to secure the prosthetic valve to the holder. For this purpose, holder 430 may include holes, loops, eyelets or the like proximal to rim 442 through which sutures may be placed. Alternatively, holder 430 may be made of a soft elastomeric material through which a suture needle may be driven to secure the suture to the holder. When it is desired to remove the prosthetic valve from holder 430, the sutures are cut with scissors or a knife.

Certain prosthetic valves are designed to allow the valve body and valve leaflets to be rotated relative to the sewing ring of the prosthesis after the sewing ring has been secured to the heart. Advantageously, once holder 430 has been removed from prosthetic valve 432 and the prosthetic valve secured in the heart, holder 430 may be used to rotate valve body 436 along with leaflets 434 by repositioning holder 430 within the V-shaped space formed by leaflets 434 and rotating handle 320 about its longitudinal axis. A flat 458 is provided along the two sides of holder 430 which are positioned adjacent to side supports 459 of prosthetic valve 432, allowing torque to be transmitted to valve body 436 rather than to the fragile valve leaflets 434.

Figure 35:
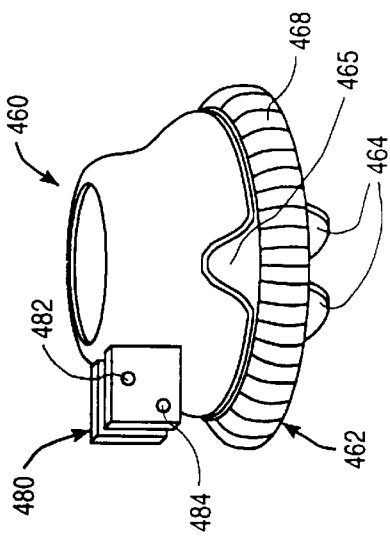
FIG. 35 is a perspective view of a further embodiment of a valve holder according to the invention holding the bileaflet mechanical heart valve of FIG. 34.
Figure 36A:
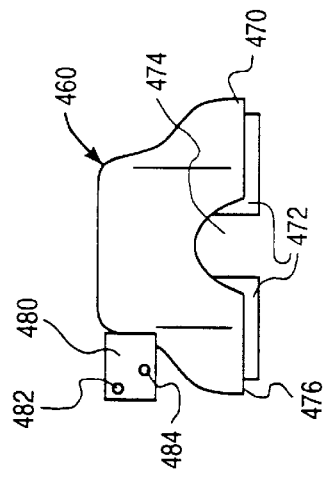
FIGS. 36A–36C are side, bottom, and proximal end views, respectively of the valve holder of FIG. 35.
Figure 36B:
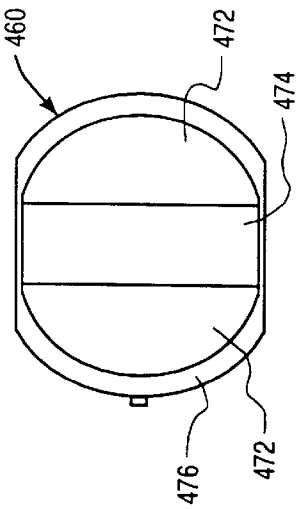
Figure 36C:
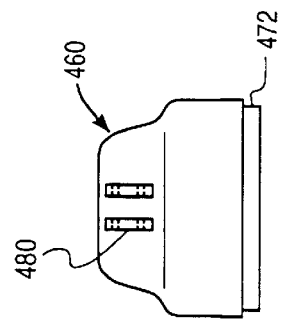
Figure 34:
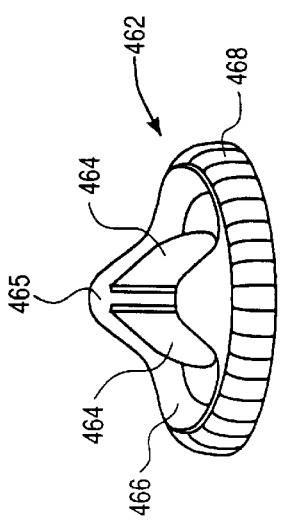
FIG. 34 is a perspective view of a bileaflet mechanical heart valve useful in conjunction with the devices and methods of the invention.

FIGS. 34–36 illustrate an alternative embodiment of a holder according to the invention. In this embodiment, holder 460 is configured to hold a bi-leaflet mechanical valve from its upstream side for replacement of a diseased cardiac valve from the upstream side of the native valve, e.g., for replacement of the mitral valve via an incision in the left atrium as described in copending application Ser. No. 08/281,962 and Ser. No. 08/485,600, which have been incorporated herein by reference. As shown in FIG. 34, mechanical bileaflet valve 462 has a pair of leaflets 464 movably attached to a pair of upwardly extending side supports 465 on an annular valve body 466. A sewing ring 468 is attached to valve body 466. Leaflets 464 are pivotable between an open position wherein the leaflets are nearly parallel, to a closed position wherein the inner edges of leaflets 464 abut one another and the curved outer edges of the leaflets abut the inner surface of annular valve body 466. As shown in FIGS. 35–36, holder 460 is configured to be positioned on the upstream side of valve 462 with leaflets 464 in the open position. Holder 460 has a distal end 470 having a pair of crescent-shaped feet 472 for positioning between the outer (upstream) surface of each leaflet 464 and the inner surface of valve body 466. An arcuate channel 474 extends across distal end 470 between feet 472 which accommodates side supports 465 and the inner ends of leaflets 464. A rim 476 extends around the perimeter of distal end 470 which abuts sewing ring 468 and/or valve body 466. Holder 460 is adapted for attachment to delivery handle 320 by a handle coupling 480 extending laterally from a proximal end of the holder. Handle coupling 480 has a pair of holes 482, 484 which may be attached to delivery handle 320 as described above in connection with FIGS. 33A–33B.

Prosthetic valve 462 may be releasably attached to holder 460 in various ways. In a preferred technique, holder 460 is constructed of a soft elastomer which allows a suture needle to be driven through it. In this way, one or more sutures may be placed through sewing ring 468 and through holder 460 and tied to secure the valve to the holder. Alternatively, holder 460 may be a more rigid material and holes, eyelets, or loops may be mounted to the holder to which sutures may be secured. When valve 462 is to be released, the sutures are simply cut.

An additional embodiment of an access port according to the invention is illustrated in FIGS. 37–40. In this embodiment, access port 490 comprises a tubular cannula 492 having a distal end 494, a proximal end 496, and a lumen 498 through which any of the replacement valves, valve holders and valve delivery devices described above may be positioned without interference. As described above in connection with FIGS. 27–29, lumen 498 is preferably oval-shaped, but the lumen may be any of a variety of shapes suitable for introducing a prosthetic valve into the chest with minimal retraction of the ribs. Cannula 492 has a wall 500 constructed of a material having sufficient rigidity to retract intercostal tissue so as to provide an opening into the chest through which a replacement valve may be positioned. A rim 501 is provided at proximal end 496 which is adapted to engage the outer surface of the chest. An obturator (not shown) removably positionable within lumen 498 may also be provided to facilitate introduction through the chest wall.

As best seen in FIGS. 38–39, a channel 502 extends axially through wall 500 between proximal end 496 and distal end 494. A plurality of axially-extending optical fibers 504 are distributed around channel 502 so as to surround lumen 498 and are potted, bonded or other wise fixed within channel 502 such that distal ends 506 of the optical fibers are disposed near distal end 494 of the cannula and are pointing generally in the distal direction. Optical fibers 504 extend proximally through channel 502, through an annular space 508 within rim 501, and into a flexible cable 510 attached to rim 501 that has a protective, opaque jacket 511 surrounding the optical fibers. An optical coupling 512 is fixed to the free end of cable 510 and is configured to be coupled to a conventional fiber optic light source of the type used for fiber optic lighting in endoscopes and the like, allowing light to be transmitted from the light source through optical fibers 504 and emitted from their distal ends 506.

In use, cannula 492 is positioned within a small incision between two ribs such that distal end 494 is within the chest cavity. Coupling 512 is connected to a light source so that light is emitted from optical fibers 504 so as to illuminate the chest cavity. Various surgical procedures may then be performed within the chest using instruments positioned through lumen 498 or through other access ports under the illumination provided by optical fibers 504. For example, the various steps of an aortic valve replacement procedure as described above may be performed under illumination provided by access port 490. Advantageously, access port 490 may be positioned in alignment with the aortic valve to provide the optimum angle of illumination, while at the same time providing the optimum angle of approach to the valve for introduction of instruments, valve sizers, and the prosthetic valve itself through lumen 498. The provision of optical fibers 504 on access port 490 may thereby eliminate the need for a separate light source within the body cavity for much of the procedure, reducing the number of access ports that are required.

Figure 41:
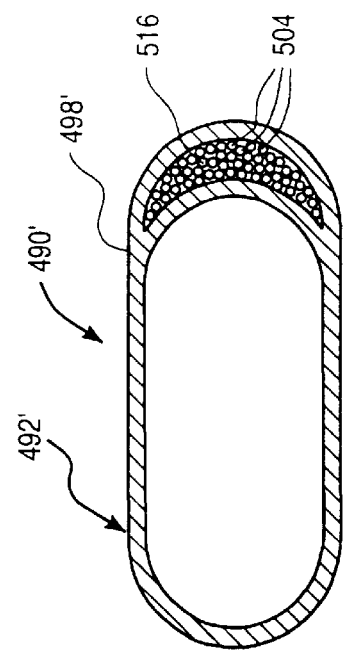
FIG. 41 is a transverse cross-section of an alternative embodiment of an access port and illumination device according to the invention.
Figure 42A:
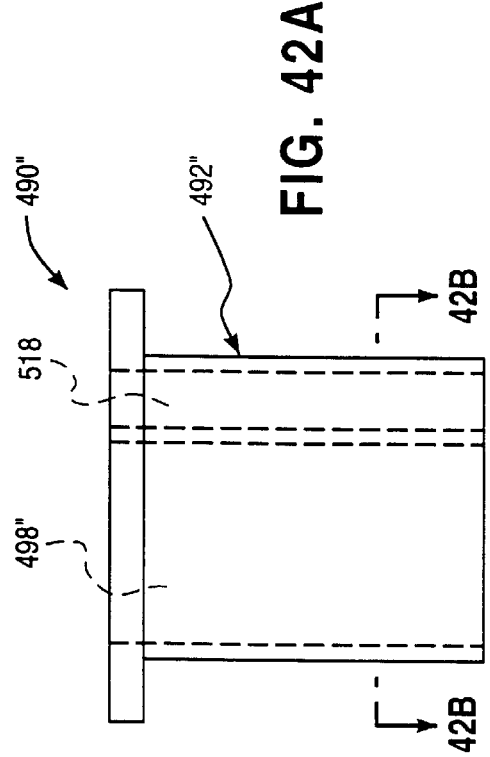
FIG. 42A is a front view of an alternative embodiment of an access port having a channel through which an illumination or visualization device may be inserted.
Figure 42B:
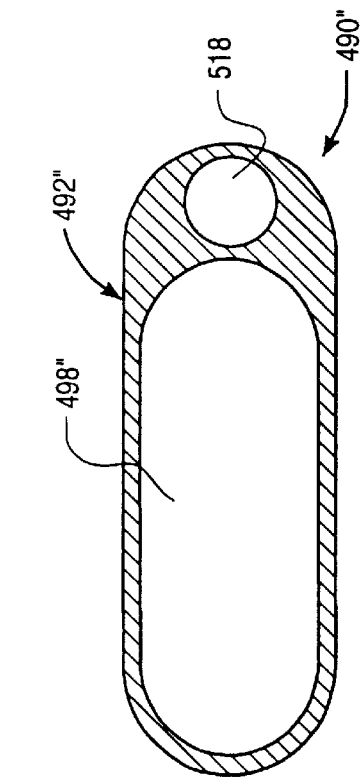
FIG. 42B is a transverse cross-section taken along line 42B—42B of FIG. 42A.

Optical fiber 504 may be mounted to access port 490 in various ways. In addition to the annular arrangement of FIGS. 37–40, optical fibers 504' may also be mounted along one side of lumen 498' in a crescent-shaped channel 516 extending through cannula 492' as shown in FIG. 41. Multiple channels (not shown) may extend along two or more sides of lumen 498 among which optical fibers 504 may be distributed. Alternatively, as shown in FIGS. 42A–42B, instead of mounting optical fibers to the access port, an open axial channel 518 may extend through cannula 492" through which an endoscopic light wand or thoracoscope (not shown) having a light source mounted to it may be slidably inserted into the body cavity alongside lumen 498".

The access ports of FIGS. 37–42 may also include any of the features of the access ports described above in connection with FIGS. 27–29, including having a suture organizer mounted to the proximal end of the access port for retaining sutures in an organized manner around lumen 498, or having a selectively deployable retention device mounted near the distal end of the access port for engaging the inner wall of the chest (or other body cavity) to maintain the access port in position.

While the above is a complete description of the preferred embodiments of the invention, various alternatives, substitutions, modifications and improvements are possible without departing from the scope hereof, which is defined by the following claims.

What is claimed is:

1. A method of accessing an internal chamber of the heat through a vessel having a lumen in fluid communication with the chamber, the heart and the vessel being within a patient's chest defined by a plurality of ribs connected to a sternum, the method comprising:

forming at least one percutaneous access port between at least one pair of adjacent ribs and positioning an instrument through a first access port of the at least one percutaneous access port and into an inner lumen of the vessel through a penetration in a wall thereof, a proximal end of the instrument extending out of the patient's chest; and manipulating the proximal end of the instrument to advance a distal end of the instrument through the vessel and into the internal chamber of the heart;

wherein all manipulations of the instrument are performed outside of the patient's chest.

2. The method of claim 1, wherein the vessel comprises an aorta and the internal chamber comprises a left ventricle, the step of manipulating comprising passing the distal end of the instrument to a position near an aortic valve position.

3. The method of claim 2, comprising attaching a valve prosthesis to the instrument prior to positioning the valve prosthesis near the aortic valve position.

4. The method of claim 3, comprising providing a suturing instrument; positioning the suturing instrument through one of the at least one percutaneous access port; and applying sutures to an annulus of the aortic valve using the suturing instrument.

5. The method of claim 4 wherein the step of applying sutures comprises positioning the suturing instrument through a second access port of the at least one percutaneous access port.

6. The method of claim 3 wherein the instrument includes a delivery handle removably coupled to the valve prosthesis.

7. The method of claim 3 comprising providing a means for orienting the valve prosthesis from a first orientation to at least a second orientation, and wherein the valve prosthesis is passed through the first percutaneous access port in a first orientation and oriented to a second orientation when the valve prosthesis is positioned within the patient's chest.

8. The method of claim 7 wherein the instrument includes an actuator and the step of orienting the valve prosthesis to a second orientation comprises actuating the actuator from outside of the patient's chest.

9. The method of claim 7 wherein the second orientation is approximately perpendicular to the first orientation.

10. The method of claim 1 wherein all steps are performed without cutting or removing the ribs or sternum.

11. The method of claim 1 comprising visualizing the vessel through a visualization device positioned in a second of the at least one percutaneous access port.

12. The method of claim 1 comprising providing a cutting tool having a blade at a distal end; passing the blade of the cutting tool through the first access port; and forming an incision in the vessel with the blade by manipulating the cutting tool from outside of the patient's chest.

13. The method of claim 12 comprising retracting the incision before positioning the instrument in the vessel lumen.

14. The method of claim 2 wherein the one of the at least one percutaneous access port is positioned in an intercostal space selected from the first, second, third, or fourth intercostal space on an anterior side of the patient's chest.

15. The method of claim 1 wherein the first percutaneous access port comprises a cannula having a proximal end outside of the patient's chest, a distal end within the patient's chest exterior to the vessel, and a passage therebetween through which the instrument is positioned.

* * * * *

UNITED STATES PATENT AND TRADEMARK OFFICE
CERTIFICATE OF CORRECTION

PATENT NO. : 6,651,671 B1  
DATED : November 25, 2003  
INVENTOR(S) : Donlon et al.

It is certified that error appears in the above-identified patent and that said Letters Patent is hereby corrected as shown below:

<u>Column 31,</u>
Line 50, please delete "heat" and insert -- heart --.

Signed and Sealed this

Twenty-seventh Day of April, 2004

JON W. DUDAS
*Acting Director of the United States Patent and Trademark Office*